United States Patent
Kangawa et al.

(10) Patent No.: US 10,071,099 B2
(45) Date of Patent: Sep. 11, 2018

(54) MEDICAMENT FOR SUPPRESSING MALIGNANT TUMOR METASTASIS

(71) Applicant: NATIONAL CEREBRAL AND CARDIOVASCULAR CENTER, Suita-shi, Osaka (JP)

(72) Inventors: Kenji Kangawa, Suita (JP); Hiroshi Hosoda, Suita (JP); Takashi Nojiri, Suita (JP)

(73) Assignee: NATIONAL CEREBRAL AND CARDIOVASCULAR CENTER, Suita-Shi (JP)

( * ) Notice: Subject to any disclaimer, the term of this patent is extended or adjusted under 35 U.S.C. 154(b) by 0 days.

(21) Appl. No.: 15/301,438

(22) PCT Filed: Apr. 3, 2015

(86) PCT No.: PCT/JP2015/060582
§ 371 (c)(1),
(2) Date: Oct. 3, 2016

(87) PCT Pub. No.: WO2015/152393
PCT Pub. Date: Oct. 8, 2015

(65) Prior Publication Data
US 2017/0014419 A1 Jan. 19, 2017

(30) Foreign Application Priority Data

Apr. 3, 2014 (JP) .................. 2014-077111

(51) Int. Cl.
A61K 31/18 (2006.01)
A01N 41/06 (2006.01)
(Continued)

(52) U.S. Cl.
CPC ........ *A61K 31/5375* (2013.01); *A61K 9/0053* (2013.01); *A61K 31/18* (2013.01); *A61K 31/192* (2013.01); *A61K 31/197* (2013.01); *A61K 31/216* (2013.01); *A61K 31/27* (2013.01); *A61K 31/277* (2013.01); *A61K 31/341* (2013.01); *A61K 31/357* (2013.01); *A61K 31/36* (2013.01); *A61K 31/381* (2013.01); *A61K 31/40* (2013.01); *A61K 31/403* (2013.01); *A61K 31/404* (2013.01); *A61K 31/4035* (2013.01); *A61K 31/41* (2013.01); *A61K 31/415* (2013.01); *A61K 31/4164* (2013.01); *A61K 31/4184* (2013.01); *A61K 31/4192* (2013.01); *A61K 31/42* (2013.01); *A61K 31/421* (2013.01); *A61K 31/423* (2013.01); *A61K 31/426* (2013.01); *A61K 31/428* (2013.01); *A61K 31/438* (2013.01); *A61K 31/44* (2013.01); *A61K 31/4402* (2013.01); *A61K 31/445* (2013.01); *A61K 31/4406* (2013.01);
(Continued)

(58) Field of Classification Search
CPC .... A61K 31/18; A61K 31/192; A61K 31/197; A61K 31/216; A61K 31/27; A61K 31/277; A61K 31/341; A61K 31/357; A61K 31/36; A61K 31/381; A61K 31/40; A61K 31/403; A61K 31/4035; A61K 31/404; A61K 31/41; A61K 31/415; A61K 31/4164; A61K 31/4184; A61K 31/4192; A61K 31/42; A61K 31/421; A61K 31/423; A61K 31/426; A61K 31/428; A61K 31/438; A61K 31/44; A61K 31/4402; A61K 31/4406; A61K 31/4409; A61K 31/4439; A61K 31/445; A61K 31/4465; A61K 31/454; A61K 31/47; A61K 31/472; A61K 31/495; A61K 31/496; A61K 31/4965; A61K 31/505; A61K 31/517; A61K 31/519; A61K 31/5375; A61K 31/554; A61K 45/06; A61K 9/0053
USPC ............... 514/601, 602, 605; 564/80, 84, 95
See application file for complete search history.

(56) References Cited

U.S. PATENT DOCUMENTS 8,461,209 B2 * 6/2013 Yoshida ................ C07C 311/51
514/601
9,486,503 B2 * 11/2016 Kangawa ........... A61K 31/4184
(Continued)

FOREIGN PATENT DOCUMENTS

IN 178290 B 3/1997
JP 2004-533457 A 11/2004
(Continued)

OTHER PUBLICATIONS

Wagenaar et al., "Agonists of MAS oncogene and angiotensin II type 2 receptors attenuate cardiopulmonary disease in rats with neonatal hyperoxia-induced lung injury", 2013, Am. J. Physiol. Lung Cell. Mol. Physiol., vol. 305, No. 5, pp. L341-L351.*
(Continued)

Primary Examiner — My-Chau T. Tran
(74) Attorney, Agent, or Firm — Birch, Stewart, Kolasch & Birch, LLP

(57) ABSTRACT

Provided are a novel medicament for suppressing or preventing the metastasis of a malignant tumor such as carcinoma, a novel treatment or prevention method for suppressing or preventing the metastasis of a malignant tumor, etc. The medicament comprises a non-peptidic angiotensin type 2 receptor agonist as an active ingredient. In the medicament, the non-peptidic angiotensin type 2 receptor agonist may be, for example, a sulfonyl malonamide compound. The medicament may be a medicament for use in combination with an anticancer agent and/or an antitumor agent.

23 Claims, 7 Drawing Sheets
Specification includes a Sequence Listing.

(51) Int. Cl.

| | |
|---|---|
| C07C 311/28 | (2006.01) |
| C07C 311/29 | (2006.01) |
| A61K 31/5375 | (2006.01) |
| A61K 9/00 | (2006.01) |
| A61K 31/197 | (2006.01) |
| A61K 31/216 | (2006.01) |
| A61K 31/277 | (2006.01) |
| A61K 31/341 | (2006.01) |
| A61K 31/357 | (2006.01) |
| A61K 31/381 | (2006.01) |
| A61K 31/4035 | (2006.01) |
| A61K 31/404 | (2006.01) |
| A61K 31/41 | (2006.01) |
| A61K 31/415 | (2006.01) |
| A61K 31/4164 | (2006.01) |
| A61K 31/4184 | (2006.01) |
| A61K 31/4192 | (2006.01) |
| A61K 31/42 | (2006.01) |
| A61K 31/421 | (2006.01) |
| A61K 31/423 | (2006.01) |
| A61K 31/426 | (2006.01) |
| A61K 31/4402 | (2006.01) |
| A61K 31/4406 | (2006.01) |
| A61K 31/4409 | (2006.01) |
| A61K 31/445 | (2006.01) |
| A61K 31/4465 | (2006.01) |
| A61K 31/454 | (2006.01) |
| A61K 31/47 | (2006.01) |
| A61K 31/495 | (2006.01) |
| A61K 31/496 | (2006.01) |
| A61K 31/4965 | (2006.01) |
| A61K 31/505 | (2006.01) |
| A61K 31/517 | (2006.01) |
| A61K 31/519 | (2006.01) |
| A61K 45/06 | (2006.01) |
| A61K 31/192 | (2006.01) |
| A61K 31/27 | (2006.01) |
| A61K 31/36 | (2006.01) |
| A61K 31/40 | (2006.01) |
| A61K 31/403 | (2006.01) |
| A61K 31/428 | (2006.01) |
| A61K 31/438 | (2006.01) |
| A61K 31/44 | (2006.01) |
| A61K 31/4439 | (2006.01) |
| A61K 31/472 | (2006.01) |
| A61K 31/554 | (2006.01) |

(52) U.S. Cl.
CPC ...... *A61K 31/4409* (2013.01); *A61K 31/4439* (2013.01); *A61K 31/4465* (2013.01); *A61K 31/454* (2013.01); *A61K 31/47* (2013.01); *A61K 31/472* (2013.01); *A61K 31/495* (2013.01); *A61K 31/496* (2013.01); *A61K 31/4965* (2013.01); *A61K 31/505* (2013.01); *A61K 31/517* (2013.01); *A61K 31/519* (2013.01); *A61K 31/554* (2013.01); *A61K 45/06* (2013.01)

(56) References Cited

U.S. PATENT DOCUMENTS

| | | |
|---|---|---|
| 2004/0167176 A1 | 8/2004 | Alterman et al. |
| 2010/0228026 A1 | 9/2010 | Yoshida et al. |
| 2014/0072557 A1* | 3/2014 | Kangawa ........... A61K 39/3955 424/134.1 |
| 2015/0258176 A1 | 9/2015 | Kangawa et al. |
| 2017/0035855 A1* | 2/2017 | Kangawa ........... A61K 31/4184 |

FOREIGN PATENT DOCUMENTS

| | | |
|---|---|---|
| WO | WO 02/096883 A1 | 12/2002 |
| WO | WO 03/064414 A1 | 8/2003 |
| WO | WO 2004/046128 A1 | 6/2004 |
| WO | WO 2004/046137 A1 | 6/2004 |
| WO | WO 2004/046141 A1 | 6/2004 |
| WO | WO 2004/085420 A1 | 10/2004 |
| WO | WO 2006/109056 A1 | 10/2006 |
| WO | WO 2006/109058 A1 | 10/2006 |
| WO | WO 2008/156142 A1 | 12/2008 |
| WO | WO 2012/118042 A1 | 9/2012 |
| WO | WO 2014/054798 A1 | 4/2014 |

OTHER PUBLICATIONS

Yang et al., "Tumor Necrosis Factor-(alpha) Inhibits Angiotensin II Receptor Type 1 Expression in Dorsal Root Ganglion Neurons via (beta)-Catenin Signaling", 2013, Neuroscience, vol. 248, pp. 383-391.*
Matavelli et al., "AT2 Receptor Activities and Pathophysiological Implications", Mar. 2015, Journal of Cardiovascular Pharmacology, vol. 65, No. 3, pp. 226-232.*
National Center for Biotechnology Information. PubChem Compound Database; CID=123794, https://pubchem.ncbi.nlm.nih.gov/compound/123794 (accessed Sep. 29, 2017).*
Ager et al., "Targeting the angiotensin II type 2 receptor (AT2R) in colorectal liver metastases", Cancer Cell International, 2010, vol. 10, No. 19, pp. 1-12.
De Gasparo et al., "International Union of Pharmacology. XXIII. The Angiotensin II Receptors", Pharmacol. Rev., 2000, vol. 52, No. 3, pp. 415-472.
International Search Report for PCT/JP2015/060582 dated Jun. 16, 2015.
McDonald et al., "Systemic inflammation increases cancer cell adhesion to hepatic sinusoids by neutrophil mediated mechanisms", Int. J. Cancer: 125, 2009, pp. 1298-1305.
Ten Kate et al., "Influence of Proinflammatory Cytokines on the Adhesion of Human Colon Carcinoma Cells to Lung Microvascular Endothelium", Int. J. Cancer: 112, 2004, pp. 943-950.
Wan et al., "Design, Synthesis, and Biological Evaluation of the First Selective Nonpeptide $AT_2$ Receptor Agonist", J. Med. Chem., 2004, vol. 47, No. 24, pp. 5995-6008.
Wu et al., "Selective Angiotensin II $AT_2$ Receptor Agonists: Arylbenzylimidazole Structure-Activity Relationships", J. Med. Chem., 2006, vol. 49, No. 24, pp. 7160-7168.
Yu et al., "Systemic and peritoneal inflammatory response after laparoscopic-assisted gastrectomy and the effect of inflammatory cytokines on adhesion of gastric cancer cells to peritoneal mesothelial cells", Surg Endosc, 2010, 24, pp. 2860-2870.
Zhou et al., "Role of Two Types of Angiotensin II Receptors in Colorectal Carcinoma Progression", Pathobiology, Aug. 2014, vol. 81, pp. 169-175.
Sugenoya, Y., "Effects of Systemic Chemotherapy and Splenectomy on Liver Metastasis from Colon-26 Cells Injected into the Spleen of Mice," Journal of Japan Society of Coloproctology, 1992, vol. 45, pp. 132-137.

\* cited by examiner

SEQUENCE LISTING

```
<160> NUMBER OF SEQ ID NOS: 14

<210> SEQ ID NO 1
<211> LENGTH: 28
<212> TYPE: PRT
<213> ORGANISM: Homo sapiens
<220> FEATURE:
<221> NAME/KEY: PEPTIDE
<223> OTHER INFORMATION: Amino acid sequence for human ghrelin

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<221> NAME/KEY: PEPTIDE
<223> OTHER INFORMATION: Amino acid sequence for human ghrelin

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus norvegicus
<220> FEATURE:
<221> NAME/KEY: PEPTIDE
<223> OTHER INFORMATION: Amino acid sequence for rat ghrelin

<400> SEQUENCE: 3

Gly Ser Ser Phe Leu Ser Pro Glu His Gln Lys Ala Gln Gln Arg Lys
```

```
1               5                   10                  15
Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: PEPTIDE
<223> OTHER INFORMATION: Amiino acid sequence for rat ghrelin

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28
<212> TYPE: PRT
<213> ORGANISM: Mus musculus
<220> FEATURE:
<221> NAME/KEY: PEPTIDE
<223> OTHER INFORMATION: Amino acid sequence for mouse ghrelin

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa
<220> FEATURE:
<221> NAME/KEY: PEPTIDE
<223> OTHER INFORMATION: Amino acid sequence for porcine ghrelin

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus
<220> FEATURE:
<221> NAME/KEY: PEPTIDE
<223> OTHER INFORMATION: Amino acid sequence for bovine ghrelin

<400> SEQUENCE: 7

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
```

```
<221> NAME/KEY: PEPTIDE
<223> OTHER INFORMATION: Amino acid sequence for ovine ghrelin

<400> SEQUENCE: 8

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<221> NAME/KEY: PEPTIDE
<223> OTHER INFORMATION: Amino acid sequence for dog ghrelin

<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Equus caballus
<220> FEATURE:
<221> NAME/KEY: PEPTIDE
<223> OTHER INFORMATION: Amino acid sequence for equine ghrelin

<400> SEQUENCE: 10

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 11
<211> LENGTH: 1457
<212> TYPE: DNA
<213> ORGANISM: Homo sapiens
<220> FEATURE:
<221> NAME/KEY: CDS
<222> LOCATION: (165)..(722)

<400> SEQUENCE: 11
ggcacgagct ggatagaaca gctcaagcct tgccacttcg ggcttctcac tgcagctggg      60
cttggacttc ggagttttgc cattgccagt gggacgtctg agactttctc cttcaagtac     120
ttggcagatc actctcttag cagggtctgc gcttcgcagc cggg atg aag ctg gtt     176
                                                Met Lys Leu Val
                                                1 tcc gtc gcc ctg atg tac ctg ggt tcg ctc gcc ttc cta ggc gct gac       224
Ser Val Ala Leu Met Tyr Leu Gly Ser Leu Ala Phe Leu Gly Ala Asp
5               10                  15                  20 acc gct cgg ttg gat gtc gcg tcg gag ttt cga aag aag tgg aat aag       272
Thr Ala Arg Leu Asp Val Ala Ser Glu Phe Arg Lys Lys Trp Asn Lys
            25                  30                  35 tgg gct ctg agt cgt ggg aag agg gaa ctg cgg atg tcc agc agc tac       320
Trp Ala Leu Ser Arg Gly Lys Arg Glu Leu Arg Met Ser Ser Ser Tyr
        40                  45                  50 ccc acc ggg ctc gct gac gtg aag gcc ggg cct gcc cag acc ctt att       368
Pro Thr Gly Leu Ala Asp Val Lys Ala Gly Pro Ala Gln Thr Leu Ile
    55                  60                  65
```

```
cgg ccc cag gac atg aag ggt gcc tct cga agc ccc gaa gac agc agt    416
Arg Pro Gln Asp Met Lys Gly Ala Ser Arg Ser Pro Glu Asp Ser Ser
    70                  75                  80 ccg gat gcc gcc cgc atc cga gtc aag cgc tac cgc cag agc atg aac    464
Pro Asp Ala Ala Arg Ile Arg Val Lys Arg Tyr Arg Gln Ser Met Asn
85                  90                  95                 100 aac ttc cag ggc ctc cgg agc ttt ggc tgc cgc ttc ggg acg tgc acg    512
Asn Phe Gln Gly Leu Arg Ser Phe Gly Cys Arg Phe Gly Thr Cys Thr
                105                 110                 115 gtg cag aag ctg gca cac cag atc tac cag ttc aca gat aag gac aag    560
Val Gln Lys Leu Ala His Gln Ile Tyr Gln Phe Thr Asp Lys Asp Lys
            120                 125                 130 gac aac gtc gcc ccc agg agc aag atc agc ccc cag ggc tac ggc cgc    608
Asp Asn Val Ala Pro Arg Ser Lys Ile Ser Pro Gln Gly Tyr Gly Arg
        135                 140                 145 cgg cgc cgg cgc tcc ctg ccc gag gcc ggc ccg ggt cgg act ctg gtg    656
Arg Arg Arg Arg Ser Leu Pro Glu Ala Gly Pro Gly Arg Thr Leu Val
    150                 155                 160 tct tct aag cca caa gca cac ggg gct cca gcc ccc ccg agt gga agt    704
Ser Ser Lys Pro Gln Ala His Gly Ala Pro Ala Pro Pro Ser Gly Ser
165                 170                 175                 180 gct ccc cac ttt ctt tag gatttaggcg cccatggtac aaggaatagt           752
Ala Pro His Phe Leu
                185 cgcgcaagca tcccgctggt gcctcccggg acgaaggact tcccgagcgg tgtgggacc   812 gggctctgac agccctgcgg agaccctgag tccgggaggc accgtccggc ggcgagctct   872 ggctttgcaa gggcccctcc ttctgggggc ttcgcttcct tagccttgct caggtgcaag    932 tgccccaggg ggcggggtgc agaagaatcc gagtgtttgc caggcttaag gagaggagaa   992 actgagaaat gaatgctgag accccggag cagggggtctg agccacagcc gtgctcgccc  1052 acaaactgat ttctcacggc gtgtcacccc accaggggcgc aagcctcact attacttgaa 1112 ctttccaaaa cctaaagagg aaaagtgcaa tgcgtgttgt acatacagag gtaactatca  1172 atatttaagt ttgttgctgt caagatttttt tttgtaactt caaatataga gatattttg   1232 tacgttatat attgtattaa gggcatttta aaagcaatta tattgtcctc ccctatttta   1292 agacgtgaat gtctcagcga ggtgtaaagt tgttcgccgc gtggaatgtg agtgtgtttg   1352 tgtgcatgaa agagaaagac tgattacctc ctgtgtggaa gaaggaaaca ccgagtctct   1412 gtataatcta tttacataaa atgggtgata tgcgaacagc aaacc                   1457

<210> SEQ ID NO 12
<211> LENGTH: 185
<212> TYPE: PRT
<213> ORGANISM: Homo sapiens

<400> SEQUENCE: 12

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80
```

```
Glu Asp Ser Ser Pro Asp Ala Ala Arg Ile Arg Val Lys Arg Tyr Arg
                85                  90                  95
Gln Ser Met Asn Asn Phe Gln Gly Leu Arg Ser Phe Gly Cys Arg Phe
            100                 105                 110
Gly Thr Cys Thr Val Gln Lys Leu Ala His Gln Ile Tyr Gln Phe Thr
        115                 120                 125
Asp Lys Asp Lys Asp Asn Val Ala Pro Arg Ser Lys Ile Ser Pro Gln
    130                 135                 140
Gly Tyr Gly Arg Arg Arg Arg Ser Leu Pro Glu Ala Gly Pro Gly
145                 150                 155                 160
Arg Thr Leu Val Ser Ser Lys Pro Gln Ala His Gly Ala Pro Ala Pro
                165                 170                 175
Pro Ser Gly Ser Ala Pro His Phe Leu
                180                 185

<210> SEQ ID NO 13
<211> LENGTH: 52
<212> TYPE: PRT
<213> ORGANISM: Homo sapiens

<400> SEQUENCE: 13

Tyr Arg Gln Ser Met Asn Asn Phe Gln Gly Leu Arg Ser Phe Gly Cys
1               5                   10                  15
Arg Phe Gly Thr Cys Thr Val Gln Lys Leu Ala His Gln Ile Tyr Gln
                20                  25                  30
Phe Thr Asp Lys Asp Lys Asp Asn Val Ala Pro Arg Ser Lys Ile Ser
            35                  40                  45
Pro Gln Gly Tyr
    50

<210> SEQ ID NO 14
<211> LENGTH: 20
<212> TYPE: PRT
<213> ORGANISM: Homo sapiens

<400> SEQUENCE: 14

Ala Arg Leu Asp Val Ala Ser Glu Phe Arg Lys Lys Trp Asn Lys Trp
1               5                   10                  15
Ala Leu Ser Arg
            20
```

MEDICAMENT FOR SUPPRESSING MALIGNANT TUMOR METASTASIS

TECHNICAL FIELD

The present invention relates to a novel medicament for suppressing or preventing the metastasis of a malignant tumor, such as carcinoma, the medicament comprising, as an active ingredient, a non-peptidic angiotensin type 2 receptor agonist. The present invention also relates to a vasoprotective agent comprising a non-peptidic angiotensin type 2 receptor agonist, and to a novel medicament for suppressing or preventing the metastasis of a malignant tumor, such as carcinoma, the medicament comprising, as an active ingredient, the vasoprotective agent. The present invention also relates to a novel treatment or prevention method etc. for suppressing or preventing the metastasis of a malignant tumor. The present invention further relates to a medicament for suppressing or preventing malignant tumor cells from colonizing or invading vascular endothelium, and also relates to a method for suppressing or preventing malignant tumor cells from colonizing or invading vascular endothelium.

BACKGROUND ART

Malignant tumors represented by carcinoma are diseases caused by abnormal growth of cells, and the most distinctive characteristic of malignant tumors is invasion into the surrounding tissue and metastasis to other organs. It has been long known that the leading cause of death for malignant tumor patients is not the growth of the primary lesion but multiple organ failure resulting from distant metastasis of the tumor cells. However, control of malignant tumor metastasis has not yet been achieved so far and is one of the most crucial issues in the whole area of cancer treatment.

Metastasis of an epithelial malignant tumor (carcinoma) is considered to be caused by various physiological phenomena of cancer cells, such as the acquisition of motility and migrating ability typified by epithelial to mesenchymal transition (hereinafter, abbreviated to "EMT"), invasion into the surrounding tissue, migration and invasion into blood vessels and lymphatic vessels, colonization in vascular endothelium of distant tissue, metastatic lesion formation, etc.

Also in a non-epithelial malignant tumor (sarcoma etc.), tumor cells that have become malignant and acquired motility and migrating ability invade blood vessels etc., colonize vascular endothelium of distant tissue, invade the tissue, and then form a metastatic lesion.

In this process, interaction between endothelial selectins of blood vessels, in particular capillary vessels, and selectin ligands expressed on tumor cells is involved in the colonization of circulating tumor cells in vascular endothelium (Non Patent Literature 1). It is also known that inflammatory cytokines (IL-1β, TNF-α) promote the adhesion of tumor cells to vascular endothelium cells (Non Patent Literature 2 and 3). For example, inflammatory cytokines caused by surgery or a surgery-induced infection systemically and locally promote the adhesion of tumor cells to vascular endothelium cells and facilitate the metastasis of the tumor cells to distant tissue and tumor recurrence at the primary site (Non Patent Literature 1 to 3).

In the prevailing pharmacological treatment for cancer, an anticancer agent and/or an antitumor agent is administered to a tumor-bearing patient usually for the purpose of reducing the size of the primary focus, and the effect of the anticancer agent and/or the antitumor agent is judged by the reduction percentage. However, an anticancer/antitumor agent is often harmful to normal tissue, and so-called "adverse effects" that cause various organ disorders appear at a high rate. Therefore, chronic dosing of an anticancer agent and/or an antitumor agent causes problems of such serious side effects. For this reason, in actual cancer treatment, the administration of an anticancer agent and/or an antitumor agent has often to be restricted in terms of the amount and duration, leading to shortened life expectancy.

Meanwhile, in the living body, angiotensinogen is converted, via renin, into angiotensin I, which is further converted by converting enzymes, such as angiotensin converting enzyme (ACE), into angiotensin II (AngII), which has various strong physiological functions.

As a receptor to which the aforementioned AngII binds, angiotensin receptors type 1 (hereinafter referred to as AT1 receptors) and AT2 receptors have been identified. The hitherto known effects of AngII, such as pressor effect, vasoconstriction effect, etc. have been understood to be mainly mediated by classical AT1 receptors. Meanwhile, the functions of AT2 receptors have been rapidly revealed in recent years. AT2 receptors antagonize AT1 receptors in many cells and tissues, and act in the direction of inhibiting the onset and progress of diseases, in particular, in the direction of pressure lowering, cell growth inhibition, hypertrophy inhibition, apoptosis promotion, and extracellular matrix production inhibition. AT2 receptors are widely and highly expressed in a fetal period, but the expression level rapidly decreases after birth. However, it has become known that, under certain diseases, such as vascular disorders, and cardiovascular remodeling after myocardial infarction, re-expression of AT2 receptors occurs in a tissue-specific manner, and the importance of AT2 receptors in the inhibition of the onset and progress of various diseases attracts attention.

General pharmacological effects that can be predicted to be exerted as a result of activating AT2 receptors are also reported in a paper by de Gasparo and others (Non Patent Literature 4), and AT2 receptor agonists are expected to exert therapeutic or preventive effects on various diseases in the medical use. Target diseases include many groups of diseases in which the renin-angiotensin-aldosterone system (hereafter referred to as RAAS) is involved, for example, metabolic diseases and circulatory diseases. Specific examples thereof include cerebral infarction, renal disease, heart disease, hypertension, diabetes mellitus, metabolic syndrome, etc.

As a non-peptidic AT2 receptor agonist, so far disclosed are 3-phenyl-2-thiophenesulfonamide and a biphenyl sulfonamide compound (Non Patent Literature 5 and 6, Patent Literature 1 to 9).

Also, it is described that CGP44112A, which is a peptidic AT2 receptor agonist, inhibits the growth of cancer cells and promotes apoptosis, and thereby inhibits the metastasis of colorectal cancer to the liver (Non Patent Literature 7).

Meanwhile, sulfonyl malonamide derivatives are known as an AT2 receptor agonist, but it is not disclosed that the derivatives suppress cancer metastasis (Patent Literature 10). In addition, sulfonyl malonamide derivatives are known as an herbicide (Patent Literature 11).

However, it has been unknown that non-peptidic AT2 receptor ligands, in particular, non-peptidic AT2 receptor agonists, suppress the metastasis of a malignant tumor (it has especially been unknown that they suppress the metastasis of a malignant tumor without targeting the malignant tumor itself).

Patent Literature 12 discloses medicines for suppressing or preventing the metastasis of a malignant tumor, the medicines comprising, as an active ingredient, vascular endothelial intracellular cGMP enhancers, such as a natriuretic peptide receptor GC-A agonist, but does not disclose the effects of a non-peptidic AT2 receptor ligand, in particular, a non-peptidic AT2 receptor agonist, on the metastasis of a malignant tumor.

CITATION LIST

Patent Literature

PTL 1: WO 02/096883
PTL 2: WO 06/109058
PTL 3: WO 03/064414
PTL 4: WO 04/046128
PTL 5: WO 04/046137
PTL 6: WO 04/085420
PTL 7: WO 06/109056
PTL 8: WO 06/109058
PTL 9: WO 04/046141
PTL 10: WO 2008/156142
PTL 11: IN Patent No. 178290
PTL 12: WO 2012/118042

Non Patent Literature

NPL 1: Braedon McDonald et al., Int. J. Cancer 125, 1298-1305 (2009)
NPL 2: Miranda Ten Kate et al., Int. J. Cancer 112, 943-950 (2004)
NPL 3: Ge Yu et al., Surg Endosc, 24, 2860-2870 (2010)
NPL 4: Pharmacol. Rev., 52, 415-472 (2000)
NPL 5: J. Med. Chem., 47, 5995-6008 (2004)
NPL 6: J. Med. Chem., 49, 7160-7168 (2006)
NPL 7: Cancer Cell International, 10; 19 (2010)

SUMMARY OF INVENTION

Technical Problem

A major objective of the present invention is to provide a novel medicament etc. for suppressing or preventing the metastasis of a malignant tumor, such as carcinoma. Another objective of the present invention is to provide a novel treatment or prevention method for suppressing or preventing the metastasis of a malignant tumor. Another objective of the present invention is to provide a medicament for suppressing or preventing malignant tumor cells from colonizing or invading vascular endothelium, and also a method for suppressing or preventing malignant tumor cells from colonizing or invading vascular endothelium. The other objectives of the present invention will become clear from the following descriptions.

Solution to Problem

The present inventors conducted extensive research to achieve the above-mentioned objectives. As a result, the inventors found that treatment using an anticancer agent and/or an antitumor agent can cause exacerbation or augmentation of distant metastasis of a malignant tumor such as carcinoma, that a non-peptidic angiotensin type 2 receptor ligand, in particular a non-peptidic angiotensin type 2 receptor agonist can effectively suppress such exacerbation or augmentation of the metastasis of a malignant tumor, and that such a non-peptidic angiotensin type 2 receptor agonist can suppress or prevent the metastasis of a malignant tumor (as well as the exacerbation and/or augmentation of a malignant tumor caused by an anticancer agent and/or an antitumor agent) by vascular protection in the host, i.e., by a mechanism completely different from that of direct effect on cancer cells as described in Non Patent Literature 7. Based on the findings, the present inventors completed the present invention.

That is, the non-peptidic angiotensin type 2 receptor ligand of the present invention, in particular the non-peptidic angiotensin type 2 receptor agonist, acts protectively on vascular endothelium and thereby effectively inhibits the colonization (adhesion) and invasion of malignant tumor cells to vascular endothelium during the process of metastasis. The adhesion and invasion of malignant tumor cells to vascular endothelium are processes common to the metastasis of tumor cells. Therefore, by inhibiting malignant tumor cells from colonizing or invading vascular endothelium, the metastasis of any and all malignant tumors can be suppressed or prevented effectively. Such a metastasis suppressing effect based on a vasoprotective effect is different from the effect that is exerted on a malignant tumor itself and suppresses the growth and the metastasis of the tumor by inhibiting angiogenesis or by suppressing DNA synthesis in the malignant tumor.

In the present invention, the metastasis of a malignant tumor (cells) includes distant metastasis of a malignant tumor (cells) and recurrence of a malignant tumor (recurrence at the site of the primary lesion (primary tumor)). The "suppressing or preventing the metastasis of a malignant tumor" means suppressing or preventing distant metastasis of a malignant tumor and/or suppressing or preventing recurrence of a malignant tumor (recurrence at the site of the primary lesion).

That is, the medicament (or also called medicinal composition, hereinafter the same holds true) of the present invention comprises, as an active ingredient, a non-peptidic angiotensin type 2 receptor agonist (hereinafter, may be referred to as AT2 receptor agonist). Such a medicament of the present invention is useful for suppressing or preventing the metastasis of a malignant tumor.

The medicament of the present invention is also useful for suppressing or preventing the metastasis (exacerbation and/or augmentation of the metastasis) of a malignant tumor caused by an anticancer agent and/or an antitumor agent.

The medicament of the present invention is also useful for suppressing or preventing the exacerbation and/or augmentation of the metastasis of a malignant tumor associated with vascular inflammation. The medicament of the present invention is also useful for suppressing or preventing the exacerbation and/or augmentation of the metastasis of a malignant tumor associated with vascular inflammation caused by surgery.

A non-peptidic angiotensin type 2 receptor agonist has a vasoprotective effect (vasoprotective function) and thereby can suppress or prevent the colonization or invasion of malignant tumor cells to vascular endothelium, and as a result, can effectively suppress or prevent the metastasis of a malignant tumor (as well as the exacerbation and/or augmentation of the metastasis of a malignant tumor caused by an anticancer agent and/or an antitumor agent). Therefore, the present invention includes a vasoprotective agent comprising a non-peptidic angiotensin type 2 receptor agonist. Such a vasoprotective agent is required to comprise at least a non-peptidic angiotensin type 2 receptor agonist, and may further comprise another vasoprotective ingredient (for example, another metastasis-suppressing agent described later, or the like).

As described above, a non-peptidic angiotensin type 2 receptor agonist (or the medicament or the vasoprotective agent) has various kinds of functions, and provides novel applications based on the functions. Therefore, the present invention also includes the following (i) to (v).

(i) A non-peptidic angiotensin type 2 receptor agonist (or the vasoprotective agent) for use in the suppression or prevention of the metastasis of a malignant tumor.

(ii) A non-peptidic angiotensin type 2 receptor agonist (or the vasoprotective agent) for use in the suppression or prevention of the exacerbation and/or augmentation of the metastasis of a malignant tumor caused by an anticancer and/or antitumor agent.

(iii) A medicament (or the vasoprotective agent) for suppressing or preventing the colonization or invasion of malignant tumor cells to vascular endothelium, the medicament (or the vasoprotective agent) comprising, as an active ingredient, a non-peptidic angiotensin type 2 receptor agonist.

(iv) A method for suppressing or preventing the colonization or invasion of malignant tumor cells to vascular endothelium, the method comprising administering, to a patient, a non-peptidic angiotensin type 2 receptor agonist or the vasoprotective agent (or an effective amount thereof).

(v) A non-peptidic angiotensin type 2 receptor agonist (or the vasoprotective agent) for use in the suppression or prevention of the colonization or invasion of malignant tumor cells to vascular endothelium.

In the present invention, the non-peptidic angiotensin type 2 receptor agonist of the present invention may be, for example, a compound represented by the following general formula (I) or a pharmacologically acceptable salt thereof.

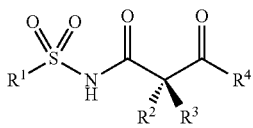

[In the formula, $R^1$ represents 2-naphthyl, trans-β-styryl, phenethyl, 3-phenoxypropyl, or 4-phenylbutyl;
one of $R^2$ and $R^3$ represents a hydrogen atom, and the other represents isopropyl, isobutyl, neopentyl, allyl, —CH$_2$—R$^5$ {wherein R$^5$ represents optionally substituted C$_{3-10}$ cycloalkyl, optionally substituted heterocycle, or —CO—NR$^6$R$^7$ (wherein R$^6$ and R$^7$ may be the same or different, and each represent a hydrogen atom, C$_{1-6}$ alkyl, optionally substituted aryl, or optionally substituted heteroaryl, or R$^5$ and R$^6$ together with the nitrogen atom to which they are bonded may form optionally substituted cyclic amino)}, —(CH$_2$)$_2$—R$^{5'}$ (wherein R$^{5'}$ represents cyano or C$_{1-6}$ alkoxy), or —(CH$_2$)$_n$—Ar (wherein n represents an integer of 1 to 3, and Ar represents optionally substituted phenyl or optionally substituted heteroaryl) or R$^2$ and R$^3$ together with the carbon atom to which they are bonded may form the moiety of the following formula:

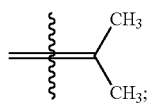

and
$R^4$ represents di(C$_{1-6}$ alkyl)amino or the moiety of the following formula:

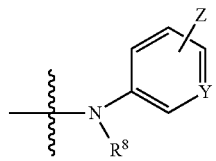

(wherein Z represents a hydrogen atom, a halogen atom, or trifluoromethyl, Y represents a nitrogen atom or CH, and $R^8$ represents ethyl, isopropyl, or 3-pentyl with the proviso that when Y is a nitrogen atom, Z represents a hydrogen atom).]

In particular, the non-peptidic angiotensin type 2 receptor agonist may be at least one kind of compound selected from
N,N-diethyl-2-{4-[(2,6-difluorobenzoyl)amino]benzyl}-N'-(2-naphthylsulfonyl)malonamide,
(2S)-2-[4-(benzoylamino)benzyl]-N,N-diethyl-N'-(2-naphthylsulfonyl)malonamide,
(2S)—N,N-diethyl-2-{4-[(2-fluorobenzoyl)amino]benzyl}-N'-(2-naphthylsulfonyl)malonamide,
(2S)—N,N-diethyl-2-{4-[(3-fluorobenzoyl)amino]benzyl}-N'-(2-naphthylsulfonyl)malonamide,
(2S)—N,N-diethyl-2-{4-[(2,4-difluorobenzoyl)amino]benzyl}-N'-(2-naphthylsulfonyl)malonamide,
(2S)—N,N-diethyl-2-{4-[(4-methylbenzoyl)amino]benzyl}-N'-(2-naphthylsulfonyl)malonamide,
(2S)—N,N-diethyl-N'-(2-naphthylsulfonyl)-2-{4-[(2-thienoyl)amino]benzyl}malonamide,
(2S)—N,N-diethyl-2-{4-[(2-furoyl)amino]benzyl}-N'-(naphthylsulfonyl)malonamide,
(2S)-2-{4-[(2-amino-5-fluorobenzoyl)amino]benzyl}-N,N-diethyl-N'-(2-naphthylsulfonyl)malonamide,
(2S)-2-{4-[(2-amino-6-fluorobenzoyl)amino]benzyl}-N,N-diethyl-N'-(2-naphthylsulfonyl)malonamide,
(2S)—N,N-diethyl-N'-(2-naphthylsulfonyl)-2-{4-[(2-pyridylcarbonyl)amino]benzyl}malonamide,
(2S)-2-{4-[(2-amino-4-chlorobenzoyl)amino]benzyl}-N,N-diethyl-N'-(2-naphthylsulfonyl)malonamide,
(2S)-2-{4-[(2-aminobenzoyl)amino]benzyl}-N,N-diethyl-N'-(2-naphthylsulfonyl)malonamide,
(2S)-2-{4-[(2-amino-5-chlorobenzoyl)amino]benzyl}-N,N-diethyl-N'-(2-naphthylsulfonyl)malonamide,
(2S)-2-{4-[(2-amino-4,5-difluorobenzoyl)amino]benzyl}-N,N-diethyl-N'-(2-naphthylsulfonyl)malonamide,
(2S)-2-{4-[(2-amino-4-fluorobenzoyl)amino]benzyl}-N,N-diethyl-N'-(2-naphthylsulfonyl)malonamide,
(2S)-2-{4-[(2-amino-5-methylbenzoyl)amino]benzyl}-N,N-diethyl-N'-(2-naphthylsulfonyl)malonamide,
2-(4-fluorobenzyl)-N-isopropyl-N-(3-pyridyl)-N'-((E)-styrylsulfonyl)malonamide,
2-allyl-N-(4-fluorophenyl)-N-isopropyl-N'-((E)-styrylsulfonyl)malonamide,
N-(4-fluorophenyl)-2-isobutyl-N-isopropyl-N'-((E)-styrylsulfonyl)malonamide,
N-(4-fluorophenyl)-2-isobutyl-N-isopropyl-N'-phenethylsulfonylmalonamide,
N-(4-fluorophenyl)-2-isobutyl-N-isopropyl-N'-(2-naphthylsulfonyl)malonamide,
(2S or 2R)-2-cyclopropylmethyl-N-(4-fluorophenyl)-N-isopropyl-N'-((E)-2-styrylsulfonyl)malonamide,
2-cyclopropylmethyl-N-(4-fluorophenyl)-N-isopropyl-N'-phenethylsulfonylmalonamide, and 2-cyclopropylmethyl-N-(4-fluorophenyl)-N-isopropyl-N'-(2-naphthylsulfonyl)malonamide,
or a pharmacologically acceptable salt thereof.

In the present invention, the metastasis of a malignant tumor may be, for example, metastasis to at least one kind selected from the lung, the bone, the liver, and the brain (for example, metastasis to at least one kind selected from the lung and the liver). Also, in the present invention, the malignant tumor may be, for example, at least one kind selected from epithelial malignant tumor, non-epithelial malignant tumor, and melanoma (the malignant tumor may be, for example, melanoma).

In the present invention, the patient as a subject of administration may be a patient who is to undergo or who has undergone resection of a malignant tumor. Also, the patient as a subject of administration may be a patient who is receiving or who has received administration of an anticancer agent and/or an antitumor agent.

The non-peptidic angiotensin type 2 receptor agonist may be used together with an anticancer agent and/or an antitumor agent. Therefore, the medicament of the present invention (the non-peptidic angiotensin type 2 receptor agonist or the vasoprotective agent) may be for use together with an anticancer agent and/or an antitumor agent (for example, a platinum-based antitumor agent).

As described above, the non-peptidic angiotensin type 2 receptor agonist is useful for suppressing or preventing exacerbation and/or augmentation of the metastasis caused by an anticancer agent and/or an antitumor agent, but for effective expression of such a suppressive or preventive function, it is preferable to administer the non-peptidic angiotensin type 2 receptor agonist from before the administration of the anticancer agent and/or the antitumor agent to the patient (for example, from one or more days before the start of the administration of the anticancer agent and/or the antitumor agent).

Peptidic agonists such as those in Non Patent Literature 7 decompose in the living body, and therefore, are not suitable for oral administration. In contrast, the angiotensin type 2 receptor agonist of the present invention is non-peptidic and therefore suitable for oral administration, and the orally administered agonist effectively exhibits the above-mentioned functions.

Therefore, the medicament (the non-peptidic angiotensin type 2 receptor agonist or the vasoprotective agent) of the present invention may be specifically used for oral administration (i.e., as a medicament for oral administration, or an oral preparation).

Many of treatment agents against malignant tumor metastasis that are currently used or under development suppress the metastasis through a mechanism of controlling the malignant tumor itself. However, the target tissue of the present invention is blood vessels and perivascular tissue (preferably vascular endothelium but not limited to vascular endothelial cells), and the malignant tumor metastasis suppressing effect is exerted by controlling the host's physiology. The treatment method has a completely different mechanism from the conventional one and is a novel technology applicable to any and all malignant tumors regardless of the kind or the nature of the malignant tumor. For example, the present invention suppresses or prevents the colonization and invasion of malignant tumor cells to vascular endothelium, and owing to such a vasoprotective effect, effectively suppresses or prevents the metastasis of a malignant tumor.

Advantageous Effects of Invention

The medicament, the treatment or prevention method, etc. of the present invention have an excellent effect of effectively suppressing or preventing the metastasis of a malignant tumor. In particular, the medicament, the treatment or prevention method, etc. of the present invention can effectively suppress or prevent the metastasis of a malignant tumor through a vasoprotective effect. For example, the medicament, the treatment or prevention method, etc. of the present invention suppresses or prevents the colonization and invasion of malignant tumor cells to vascular endothelium in the process of the metastasis of a malignant tumor. Thus, the medicament, the treatment or prevention method, etc. of the present invention exerts an excellent metastasis suppressing/preventing effect.

The inventors found that administration of an anticancer agent and/or an antitumor agent (for example, a platinum-based antitumor agent, such as cisplatin (CDDP)) causes vascular endothelial disorder, which promotes the adhesion and invasion of malignant tumor cells to the vascular endothelium and thus facilitates the metastasis of a malignant tumor. The medicament or the like of the present invention, through its vasoprotective effect, suppresses the adhesion of malignant tumor cells to the vascular endothelium induced by administration of an anticancer agent and/or an antitumor agent, and thus exerts an excellent tumor metastasis suppressing effect (suppressing effect on tumor metastasis (distant tumor metastasis) and/or suppressing effect on tumor recurrence). Therefore, the use of the medicament or the like of the present invention effectively suppresses or prevents exacerbation and/or augmentation of the metastasis of a malignant tumor caused by an anticancer agent and/or an antitumor agent.

Further, the medicament or the like of the present invention, through its vasoprotective effect, suppresses surgery-induced or promoted adhesion of malignant tumor cells to vascular endothelial cells in the whole body or part of the body, and thus has an excellent tumor metastasis suppressing effect. Further, the medicament or the like of the present invention, due to its vasoprotective effect, has an effect of efficiently suppressing the metastasis (as well as exacerbation and/or augmentation of the metastasis) of a malignant tumor associated with vascular inflammation (for example, vascular inflammation caused by surgery).

With such excellent effects, the present invention can prevents or suppresses the metastasis of a malignant tumor, prevents the recurrence after therapeutic resection of a tumor, and also effectively suppresses or prevents the metastasis of a malignant tumor that is hard to resect. As a result, an extended survival period can be obtained.

DESCRIPTION OF EMBODIMENTS

Figure 1:
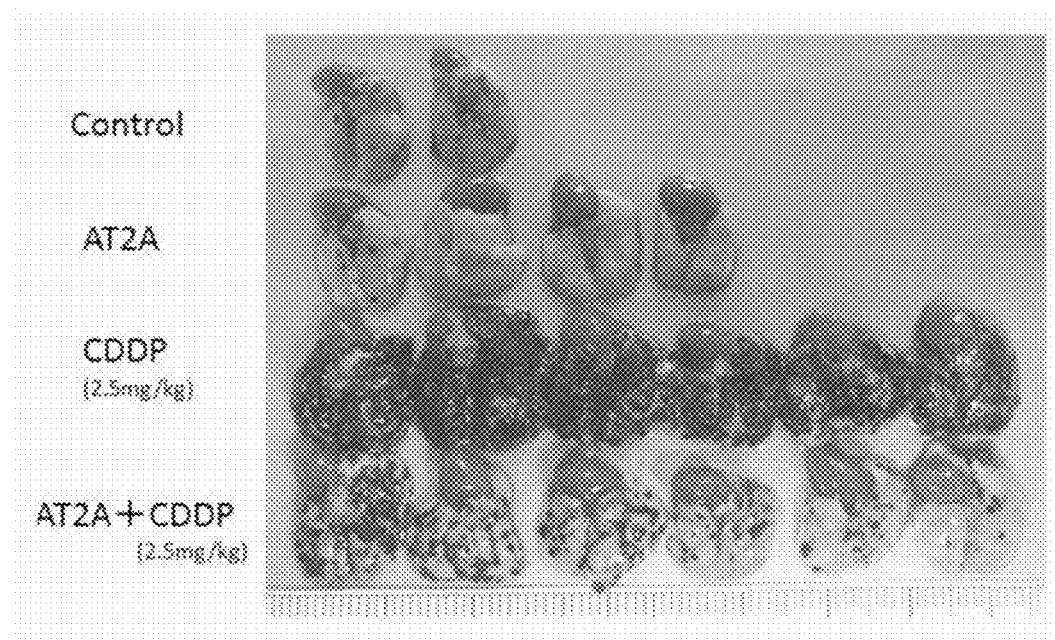
FIG. 1 shows micrographs of lungs at 2 weeks after the injection of mouse melanoma B16-F10 tumor cells into the tail vein of mice in a tail vein injection metastasis test where injection of CDDP and/or oral administration of Compound A were performed.

In the present invention, among angiotensin type 2 receptor agonists, non-peptidic agonists are used. The molecular weight of such an agonist is, for example, 1000 or less, preferably 800 or less, and an AT2 receptor agonist having a molecular weight of 300 to 700 is particularly preferred.

The non-peptidic angiotensin type 2 receptor agonist of the present invention is not particularly limited, and examples thereof include sulfonamide compounds [for example, a 3-phenyl-2-thiophene sulfonamide compound, a biphenyl sulfonamide compound, and a sulfonyl malonamide compound], etc. Specific examples of the AT2 receptor agonist include the compounds described in WO 2008/156142, WO 2002/096883, etc.

Among them, preferred as the non-peptidic angiotensin type 2 receptor agonist are sulfonyl malonamide compounds. In particular, the compound (I) shown below described in WO 2008/156142 or a pharmacologically acceptable salt thereof is preferred.

General Formula I

General Formula I

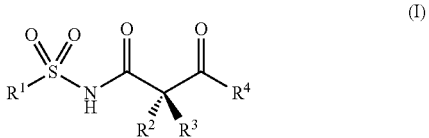

[In the formula, $R^1$ represents 2-naphthyl, trans-β-styryl, phenethyl, 3-phenoxypropyl, or 4-phenylbutyl;
one of $R^2$ and $R^3$ represents a hydrogen atom, and the other represents isopropyl, isobutyl, neopentyl, allyl, —$CH_2$—$R^5$ {wherein $R^5$ represents optionally substituted $C_{3-10}$ cycloalkyl, optionally substituted heterocycle, or —CO—$NR^6R^7$ (wherein $R^6$ and $R^7$ may be the same or different, and each represent a hydrogen atom, $C_{1-6}$ alkyl, optionally substituted aryl, or optionally substituted heteroaryl, or $R^5$ and $R^6$ together with the nitrogen atom to which they are bonded may form optionally substituted cyclic amino)}, —$(CH_2)_2$—$R^{5'}$ (wherein $R^{5'}$ represents cyano or $C_{1-6}$ alkoxy), or —$(CH_2)_n$—Ar (wherein n represents an integer of 1 to 3, and Ar represents optionally substituted phenyl or optionally substituted heteroaryl) or $R^2$ and $R^3$ together with the carbon atom to which they are bonded may form the moiety of the following formula:

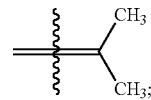

and
$R^4$ represents di($C_{1-6}$ alkyl)amino or the moiety of the following formula:

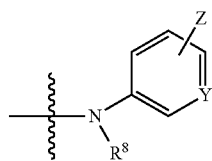

(wherein Z represents a hydrogen atom, a halogen atom, or trifluoromethyl, Y represents a nitrogen atom or CH, and $R^8$ represents ethyl, isopropyl, or 3-pentyl with the proviso that when Y is a nitrogen atom, Z represents a hydrogen atom).]

Hereinafter, each substituent in the above general formula (I) will be described in detail.

The $C_{1-6}$ alkyl means a linear or branched hydrocarbon group having 1 to 6 carbon atoms, and examples thereof include methyl, ethyl, propyl, isopropyl, butyl, isobutyl, sec-butyl, tert-butyl, pentyl, isopentyl, neopentyl, hexyl, isohexyl, etc.

The $C_{2-6}$ alkenyl described later means a linear or branched unsaturated hydrocarbon group having 2 to 6 carbon atoms and one or more carbon-carbon double bonds, and examples thereof include vinyl, allyl, 1-propenyl, isopropenyl, 2-butenyl, 1,3-butadienyl, 2-methyl-2-propenyl, prenyl, isopentenyl, 2-hexenyl, etc.

The $C_{2-6}$ alkynyl described later means a linear or branched unsaturated hydrocarbon group having 2 to 6 carbon atoms and one or more carbon-carbon triple bonds, and examples thereof include ethynyl, 2-propynyl, 2-butynyl, 3-butynyl, 3-pentynyl, 5-hexynyl, etc.

The $C_{1-6}$ alkoxy means the same as the above "$C_{1-6}$ alkyl", and examples thereof include methoxy, ethoxy, propoxy, isopropoxy, butoxy, pentyloxy, hexyloxy, etc.

The $C_{3-10}$ cycloalkyl means a saturated cyclic hydrocarbon group having 3 to 10 carbon atoms, and examples thereof include cyclopropyl, cyclobutyl, cyclopentyl, cyclohexyl, cycloheptyl, etc. The cycloalkyl may be condensed with a benzene ring to form an indane (for example, indan-1-yl, indan-2-yl, etc.), a tetrahydronaphthalene (for example, tetrahydronaphthalene-5-yl, tetrahydronaphthalene-6-yl, etc.), etc.

The $C_{3-10}$ cycloalkyl $C_{1-6}$ alkyl described later means the above "$C_{1-6}$ alkyl" substituted by the above "$C_{3-10}$ cycloalkyl". The "$C_{1-6}$ alkyl" is preferably an alkyl having 1 to 3 carbon atoms, and examples of the $C_{3-10}$ cycloalkyl $C_{1-6}$ alkyl include cyclopropylmethyl, 2-cyclobutylethyl, 3-cyclopentylpropyl, cyclohexylmethyl, 2-cyclohexylethyl, cycloheptylmethyl, etc.

The aryl means an aromatic hydrocarbon group preferably having 6 to 14 carbon atoms, and examples thereof include phenyl, naphthyl, etc. The group includes an ortho-fused bicyclic group which has 8 to 10 ring atoms and of which at least one ring is an aromatic ring (for example, indenyl etc.) etc.

The aryl $C_{1-6}$ alkyl described later means the above "$C_{1-6}$ alkyl" substituted by the above "aryl", and examples of the aryl $C_{1-6}$ alkyl include benzyl, benzhydryl, phenethyl, 1-phenylethyl, 3-phenylpropyl, 4-phenylbutyl, 5-phenylpentyl, 6-phenylhexyl, 1-naphthylmethyl, 2-naphthylmethyl, 2-(1-naphthyl)ethyl, 2-(2-naphthyl)ethyl, 3-(2-naphthyl)propyl, 4-(2-naphthyl)butyl, etc.

The aryl $C_{2-6}$ alkenyl described later means the above "$C_{2-6}$ alkenyl" substituted by the above "aryl". The "$C_{2-6}$ alkenyl" is preferably an alkenyl having 2 to 4 carbon atoms, and examples of the aryl $C_{2-6}$ alkenyl include trans-β-styryl, cinnamyl, 3-(1-naphthyl)-2-propenyl, 3-(2-naphthyl)-2-propenyl, etc.

The heteroaryl means an aromatic group having, in addition to carbon atoms, one or more (preferably 1 to 4) hetero atoms selected from an oxygen atom, a sulfur atom, and a nitrogen atom. The group includes a 5- or 6-membered monocyclic group or an ortho-fused bicyclic group which has 8 to 10 ring atoms and which is derived from the monocyclic group (in particular, a benzo derivative), a group obtainable by fusing propenylene, trimethylene, or tetramethylene to said group, a stable N-oxide of said group, etc. Examples of the heteroaryl include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl (2-pyridyl, 3-pyridyl, 4-pyridyl), pyrazinyl, pyrimidinyl, pyridazinyl, 1,2,4-triazinyl, 1,2,3-triazinyl, 1,3,5-triazinyl, benzoxazolyl, benzoisoxazolyl, benzothiazolyl, benzoisothiazolyl, benzoimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indazolyl, isoquinolyl, quinolyl, phthalazinyl, quinoxalinyl, quinazolinyl, cinnolinyl, 2,1,3-benzoxadiazolyl, benzoxazinyl, pteridinyl, etc.

The heteroaryl $C_{1-6}$ alkyl described later means the above "$C_{1-6}$ alkyl" substituted by the above "heteroaryl". The "$C_{1-6}$ alkyl" is preferably an alkyl having 1 to 5 carbon atoms, and examples of the heteroaryl $C_{1-6}$ alkyl include 2-pyridylmethyl, 3-pyridylmethyl, 4-pyridylmethyl, 2-(2-pyridyl)ethyl, 2-(3-pyridyl)ethyl, 2-(4-pyridyl)ethyl, 3-(2-pyridyl)propyl, 3-(3-pyridyl)propyl, 3-(4-pyridyl)propyl, 2-thienylmethyl, 3-thienylmethyl, 2-(2-thienyl)ethyl, 3-(2-thienyl)propyl, 4-pyrazolylmethyl, 2-(4-pyrazolyl)ethyl, 3-(4-pyrazolyl)propyl, 2-thiazolylmethyl, 4-thiazolylmethyl, 5-thiazolylmethyl, 2-(2-thiazolyl)ethyl, 3-(2-thiazolyl)propyl, 2-(4-thiazolyl)ethyl, 3-(4-thiazolyl)propyl, 2-(5-thiazolyl)ethyl, 3-(5-thiazolyl)propyl, 2-oxazolylmethyl, 4-oxazolylmethyl, 5-oxazolylmethyl, 2-(2-oxazolyl)ethyl, 3-(2-oxazolyl)propyl, 2-(4-oxazolyl)ethyl, 3-(4-oxazolyl)propyl, 2-(5-oxazolyl)ethyl, 3-(5-oxazolyl)propyl, 4-(1,2,3-triazolyl)methyl, 5-tetrazolylmethyl, 2-(5-tetrazolyl)ethyl, 1-imidazolylmethyl, 2-(1-imidazolyl)ethyl, 6-benzoxazolylmethyl, 1-benzoimidazolylmethyl, etc.

The heterocycle means a cyclic hydrocarbon group having 1 to 3 hetero atoms selected from a nitrogen atom, an oxygen atom, a sulfur atom, etc. The group is non-aromatic and may be saturated or partially unsaturated. The group includes not only a monocycle but also a spiro ring, and preferred is a 4- to 7-membered monocycle or a 10- or 11-membered spiro ring. Examples of the heterocycle include azetidinyl, pyrrolidinyl, piperidinyl, piperazinyl, morpholino, 1,4-diazepanyl, 1,2,5,6-tetrahydropyridyl, tetrahydropyranyl, cyclopentanespiro-4'-piperidinyl, etc.

Further, the heterocycle may have an aromatic ring condensed therewith. Examples of the condensed ring include indolinyl, isoindolinyl, 1,2,3,4-tetrahydroquinolyl, 1,2,3,4-tetrahydroisoquinolyl, spiro[indan-1,4'-piperidin]-1'-yl, etc.

The cyclic amino means a cyclic hydrocarbon group containing at least one nitrogen atom, the nitrogen atom serving as the site of bonding of the group. This ring may contain, in addition to the nitrogen atom, 1 to 3 hetero atoms of the same kind or different kinds selected from, for example, a nitrogen atom, an oxygen atom, and a sulfur atom. The group is non-aromatic and may be saturated or partially unsaturated. The group includes not only a monocycle but also a spiro ring, and preferred is a 4- to 7-membered monocycle or a 10- or 11-membered spiro ring. Examples of the cyclic amino include azetidino, pyrrolidino, piperidino, piperazino, morpholino, 1,4-diazepan-1-yl, 1,2,5,6-tetrahydropyridino, tetrahydroimidazolino, cyclopentanespiro-4'-piperidino, etc.

Further, the cyclic amino may have an aromatic ring condensed therewith. Examples of the condensed ring include indolino, isoindolino, 1,2,3,4-tetrahydroquinolino, 1,2,3,4-tetrahydroisoquinolino, spiro[indan-1,4'-piperidin]-1'-yl, etc.

Examples of the halogen atom include a chlorine atom, a bromine atom, a fluorine atom, and an iodine atom.

Examples of the substituent(s) in the "optionally substituted $C_{3-10}$ cycloalkyl", the "optionally substituted heterocycle", the "optionally substituted aryl", the "optionally substituted phenyl", the "optionally substituted heteroaryl", and the "optionally substituted cyclic amino" include one to three substituents selected from the following substituent group A.

Substituent group A: a halogen atom (as defined above), hydroxyl, nitro, cyano, trifluoromethyl, trifluoromethoxy, $C_{1-6}$ alkyl (as defined above), $C_{2-6}$ alkenyl (as defined above), $C_{2-6}$ alkynyl (as defined above), $C_{1-6}$ alkoxy, $C_{1-6}$ alkyl thio, $C_{1-6}$ alkyl sulfinyl, $C_{3-10}$ cycloalkyl (as defined above), $C_{3-10}$ cycloalkyl $C_{1-6}$ alkyl (as defined above), aryl (as defined above), aryloxy, aryl $C_{1-6}$ alkyl (as defined above), aryl $C_{2-6}$ alkenyl (as defined above), aryl $C_{2-6}$ alkynyl, heteroaryl (as defined above), heteroaryloxy, heteroaryl $C_{1-6}$alkyl (as defined above), heterocycle (as defined above), oxo, —COOR$^a$, —CH$_2$COOR$^a$, —OCH$_2$COOR$^a$, —CONR$^b$R$^c$, —CH$_2$CONR$^b$R$^c$, —OCH$_2$CONR$^b$R$^c$, —COO(CH$_2$)$_2$NR$^e$R$^f$, —CONR$^d$SO$_2$T$^1$, —NR$^e$R$^f$, —NR$^g$CHO, —NR$^g$COT$^2$, —NR$^g$COOT$^2$, —NR$^g$CONR$^i$R$^j$, —NR$^h$SO$_2$T$^3$, —NHC(=NH)NH$_2$, —COT$^2$, —SO$_2$T, methylenedioxy, and ethyleneoxy.

The above substituent(s) may further have one to three substituents selected from the substituent group B at a substitutable position(s).

Substituent group B: a halogen atom (as defined above), hydroxyl, nitro, cyano, trifluoromethyl, trifluoromethoxy, C$_{1-6}$ alkyl (as defined above), C$_{2-6}$ alkenyl (as defined above), C$_{2-6}$ alkynyl (as defined above), C$_{1-6}$ alkoxy, C$_{1-6}$ alkyl thio, C$_{1-6}$ alkyl sulfinyl, C$_{3-10}$ cycloalkyl (as defined above), C$_{3-10}$ cycloalkyl C$_{1-6}$ alkyl (as defined above), aryl (as defined above), aryloxy, aryl C$_{1-6}$ alkyl (as defined above), aryl C$_{2-6}$ alkenyl (as defined above), aryl C$_{2-6}$ alkynyl, heteroaryl (as defined above), heteroaryloxy, heteroaryl C$_{1-6}$alkyl (as defined above), heterocycle (as defined above), oxo, —COOR$^a$, —CH$_2$COOR$^a$, —OCH$_2$COOR$^a$, —CONR$^b$R$^c$, —CH$_2$CONR$^b$R$^c$, —OCH$_2$CONR$^b$R$^c$, —COO(CH$_2$)$_2$NR$^e$R$^f$, —CONR$^d$SO$_2$T$^1$, —NR$^e$R$^f$, —NR$^g$CHO, —NR$^g$COT$^2$, —NR$^g$COOT$^2$, —NR$^g$CONR$^i$R$^j$, —NR$^h$SO$_2$T$^3$, —NHC(=NH) NH$_2$, —COT$^2$, —SO$_2$T$^3$, methylenedioxy, and ethyleneoxy.

The "C$_{1-6}$ alkyl" moiety of the "C$_{1-6}$ alkoxy" means the same as the above "C$_{1-6}$ alkyl", and examples of the C$_{1-6}$ alkyl include methoxy, ethoxy, propoxy, isopropoxy, butoxy, pentyloxy, hexyloxy, etc.

The "C$_{1-6}$ alkyl" moiety of the "C$_{1-6}$ alkyl thio" means the same as the above "C$_{1-6}$ alkyl", and examples of the C$_{1-6}$ alkyl thio include methylthio, ethylthio, propylthio, isopropylthio, butylthio, pentylthio, hexylthio, etc.

The "C$_{1-6}$ alkyl" moiety of the "C$_{1-6}$ alkyl sulfinyl" means the same as the above "C$_{1-6}$ alkyl", and examples of the C$_{1-6}$ alkyl sulfinyl include methylsulfinyl, ethylsulfinyl, propylsulfinyl, isopropylsulfinyl, butylsulfinyl, pentylsulfinyl, hexylsulfinyl, etc.

The aryl moiety of the aryloxy means the same as the above "aryl", and examples of the aryloxy include phenoxy, 1-naphthoxy, 2-naphthoxy, etc.

The aryl C$_{2-6}$ alkynyl means the above "C$_{2-6}$ alkynyl" substituted by the above "aryl". The "C$_{2-6}$ alkynyl" is preferably an alkynyl having 2 to 4 carbon atoms, and examples thereof include phenylethynyl etc.

The "heteroaryl" moiety of the heteroaryloxy means the same as the above "heteroaryl", and examples of the heteroaryloxy include 2-pyridyloxy, 2-benzothiazolyloxy, etc.

Also, R$^a$ to R$^j$ each represent a hydrogen atom, C$_{1-6}$ alkyl (as defined above), aryl (as defined above), aryl C$_{1-6}$ alkyl (as defined above), heteroaryl (as defined above), or heteroaryl C$_{1-6}$ alkyl (as defined above), and these groups may further have one to three substituents selected from the substituent group A at a substitutable position(s).

The R$^b$ and R$^c$, R$^e$ and R$^f$, and R$^i$ and R$^j$ in the —NR$^b$R$^c$, —NR$^e$R$^f$, and —NR$^i$R$^j$ may form a cyclic amino (as defined above) together with the nitrogen atom to which they are bonded; the cyclic amino may further have one to three substituents selected from the substituent group A at a substitutable position (s). The cyclic amino that —NR$^e$R$^f$ may form includes oxo-containing cyclic amino groups (for example, 2-pyrrolidinon-1-yl, 1-oxoisoindolin-2-yl, succinimide, oxazolidin-2-one-3-yl, 2-benzoxazolinon-3-yl, phthalimide, 4-quinazolinon-3-yl, etc.).

T$^1$ to T$^3$ each represent C$_{1-6}$ alkyl (as defined above), C$_{2-6}$ alkenyl (as defined above), C$_{2-6}$ alkynyl (as defined above), C$_{3-10}$ cycloalkyl (as defined above), C$_{3-10}$ cycloalkyl C$_{1-6}$ alkyl (as defined above), aryl (as defined above), aryl C$_{1-6}$ alkyl (as defined above), heteroaryl (as defined above), heteroaryl C$_{1-6}$ alkyl (as defined above), a cyclic amino (as defined above), or a heterocycle (as defined above), and these groups may have one to three substituents selected from the substituent group A at a substitutable position(s). Examples of the aryl or heteroaryl having one to three substituents selected from the substituent group A include 2-aminophenyl, 2-amino-5-fluorophenyl, 2-amino-6-fluorophenyl, 2-fluorophenyl, 4-methoxypheny, 5-chloro-2-pyridyl, etc.

More specific examples of the non-peptidic angiotensin type 2 receptor agonist of the present invention include the following compounds of Examples 1 to 588 described in WO 2008/156142.

TABLE 1

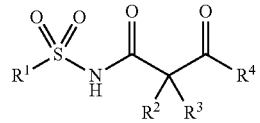

| Example | R$^1$ | R$^2$ | R$^3$ | R$^4$ |
|---|---|---|---|---|
| 1 | naphthalen-2-yl | benzyl | H | N,N-diethylaminomethyl |
| 2 | ↑ | ↑ | ↑ | —N(CH$_2$CO$_2$Et)(Et) |
| 3 | ↑ | ↑ | ↑ | —N(CH$_2$CO$_2$H)(Et) |

TABLE 1-continued
[Structure: R¹SO₂-NH-C(=O)-C(R²)(R³)-C(=O)-R⁴]
| Example | R¹ | R² | R³ | R⁴ |
|---|---|---|---|---|
| 4 | ↑ | ↑ | ↑ | -N(CH₂CO₂H)(CH₂Ph) |
| 5 | ↑ | ↑ | ↑ | piperazinyl-SO₂-(2-naphthyl) |
| 6 | ↑ | 4-O₂N-C₆H₄-CH₂- | ↑ | -N(Et)₂ |
| 7 | ↑ | 4-H₂N-C₆H₄-CH₂- | ↑ | ↑ |
| 8 | ↑ | 4-(H₂N-C(=NH)-NH)-C₆H₄-CH₂- · TFA | ↑ | ↑ |
↑: same substituent as above
TABLE 2
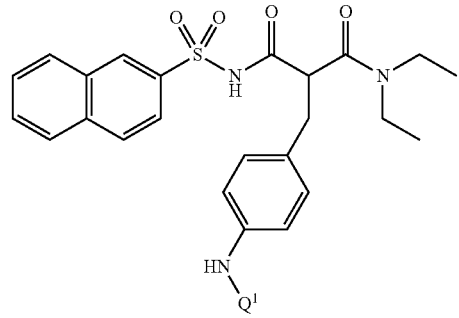
| Example | Q¹ |
|---|---|
| 9 | PhCO |
| 10 | Ac |
| 11 | iPr-C(=O)- |
TABLE 2-continued
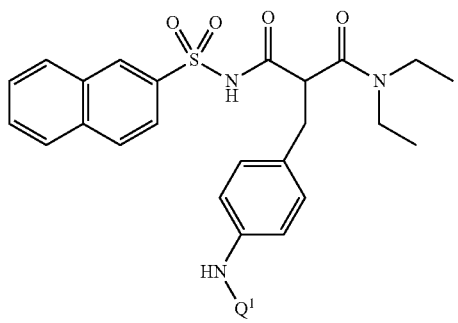
| Example | Q¹ |
|---|---|
| 12 | tBu-C(=O)- |

TABLE 2-continued

| Example | Q¹ |
|---------|-----|
| 13 | ethynyl ketone with gem-dimethyl (HC≡C-C(=O)-C(CH₃)₂-) |
| 14 | propynyl ketone with gem-dimethyl (CH₃-C≡C-C(=O)-C(CH₃)₂-) |
| 15 | cyclopropyl ketone with gem-dimethyl |
| 16 | 1-methylcyclopropyl ketone with gem-dimethyl |
| 17 | N-Boc-piperidin-4-yl ketone with gem-dimethyl |
| 18 | piperidin-4-yl ketone with gem-dimethyl (TFA salt) |
| 19 | 2-fluorophenyl ketone with gem-dimethyl |
| 20 | 4-fluorophenyl ketone with gem-dimethyl |
| 21 | 3-fluorophenyl ketone with gem-dimethyl |
| 22 | 2,6-difluorophenyl ketone with gem-dimethyl |
| 23 | 2,4-difluorophenyl ketone with gem-dimethyl |
| 24 | 2-fluoro-4-methylphenyl ketone with gem-dimethyl |
| 25 | 2-methoxyphenyl ketone with gem-dimethyl |
| 26 | 4-methoxyphenyl ketone with gem-dimethyl |
| 27 | 3-methoxyphenyl ketone with gem-dimethyl |

TABLE 2-continued

[Structure: naphthalene-SO2-NH-C(=O)-CH(CH2-C6H4-NH-Q1)-C(=O)-N(Et)2]

| Example | Q¹ |
|---------|-----|
| 28 | 2,6-dimethoxybenzoyl |
| 29 | 2-hydroxybenzoyl |
| 30 | 2-hydroxy-3-methylbenzoyl |
| 31 | 2-methylbenzoyl |
| 32 | 4-methylbenzoyl |
| 33 | 3-methylbenzoyl |
| 34 | 2,6-dimethylbenzoyl |
| 35 | 4-chlorobenzoyl |
| 36 | 2-chlorobenzoyl |
| 37 | 3-chlorobenzoyl |
| 38 | 3,4-dichlorobenzoyl |
| 39 | 5-fluoro-2-methoxybenzoyl |
| 40 | 2-(trifluoromethyl)benzoyl |
| 41 | 3-cyanobenzoyl |

TABLE 2-continued

| Example | Q¹ |
|---|---|
| 42 | 2-nitrophenyl-C(O)-C(CH₃)₂- |
| 43 | 2-aminophenyl-C(O)-C(CH₃)₂- |
| 44 | 4-aminophenyl-C(O)-C(CH₃)₂- |
| 45 | 3-aminophenyl-C(O)-C(CH₃)₂- |
| 46 | 2-amino-3-methylphenyl-C(O)-C(CH₃)₂- |
| 47 | 2-amino-5-chlorophenyl-C(O)-C(CH₃)₂- |
| 48 | 2-amino-5-fluorophenyl-C(O)-C(CH₃)₂- |
| 49 | 2-amino-3-chlorophenyl-C(O)-C(CH₃)₂- |
| 50 | 2-amino-5-methylphenyl-C(O)-C(CH₃)₂- |
| 51 | 2-amino-4-chlorophenyl-C(O)-C(CH₃)₂- |
| 52 | 2-amino-4-fluorophenyl-C(O)-C(CH₃)₂- |
| 53 | 2-amino-3,5-dichlorophenyl-C(O)-C(CH₃)₂- |
| 54 | 5-amino-2,4-difluorophenyl-C(O)-C(CH₃)₂- |
| 55 | 2-amino-6-fluorophenyl-C(O)-C(CH₃)₂- |

TABLE 2-continued
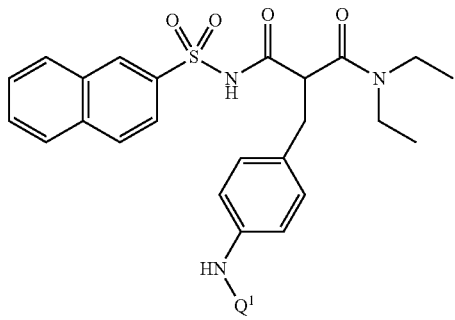
| Example | Q¹ |
|---|---|
| 56 | 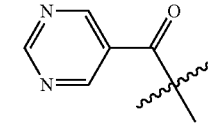 [SMILES: *C(=O)c1cncnc1] |
| 57 | 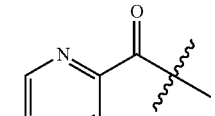 |
| 58 | 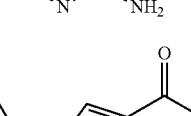 |
| 59 | 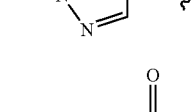 |
| 60 | 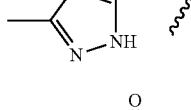 |
| 61 | 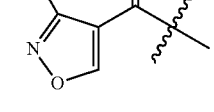 |
| 62 | 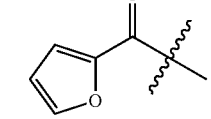 |
| 63 | 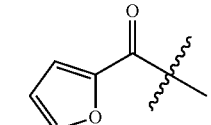 |
TABLE 2-continued
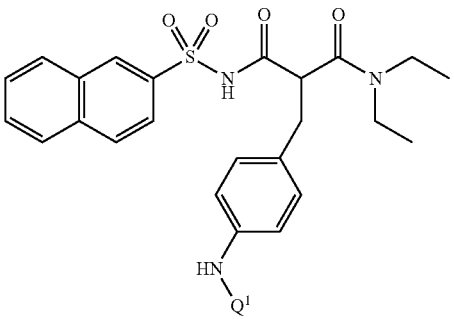
| Example | Q¹ |
|---|---|
| 64 | |
| 65 | |
| 66 | |
| 67 | |
| 68 | |
| 69 | |
| 70 | |
| 71 | |

TABLE 2-continued

| Example | Q¹ |
|---------|-----|
| 72 | 5-nitrofuran-2-yl-C(=O)-C(CH₃)₂- |
| 73 | 5-bromofuran-2-yl-C(=O)-C(CH₃)₂- |
| 74 | 4,5-dimethylfuran-2-yl-C(=O)-C(CH₃)₂- |
| 75 | thiophen-2-yl-C(=O)-C(CH₃)₂- |
| 76 | 5-methylthiophen-2-yl-C(=O)-C(CH₃)₂- |
| 77 | 5-chlorothiophen-2-yl-C(=O)-C(CH₃)₂- |
| 78 | 2,4-dimethyloxazol-5-yl-C(=O)-C(CH₃)₂- |
| 79 | 2,4-dimethylthiazol-5-yl-C(=O)-C(CH₃)₂- |
| 80 | naphthalen-1-yl-C(=O)-C(CH₃)₂- |
| 81 | quinolin-8-yl-C(=O)-C(CH₃)₂- |
| 82 | 2-methyl-1H-benzimidazol-5-yl-C(=O)-C(CH₃)₂- |
| 83 | 1H-benzimidazol-2-yl-C(=O)-C(CH₃)₂- |
| 84 | methylsulfonyl-C(CH₃)₂- |
| 85 | phenylsulfonyl-C(CH₃)₂- |

TABLE 2-continued

[Structure: Naphthalene-SO2-NH-CH(CH2-C6H4-NHQ1)-C(=O)-N(Et)2 with adjacent C(=O) group]

| Example | Q¹ |
|---------|-----|
| 86 | [4-methylphenyl-SO2-] |
| 87 | PhOCO |
| 88 | PhNHCO |
| 89 | [indoline-1-carbonyl-] |
| 90 | [Et2N-CO-C(CH3)2-] |

TABLE 3

[Structure: Naphthalene-SO2-NH-CH(S)(CH2-C6H4-Q2)-C(=O)-N(Et)2 with adjacent C(=O) group]

| Example | Q² |
|---------|-----|
| 91 | NO₂ |
| 92 | PhCONH |
| 93 | [2-fluorobenzoyl-NH-] |

TABLE 3-continued

| Example | Q² |
|---------|-----|
| 94 | [3-fluorobenzoyl-NH-] |
| 95 | [2,4-difluorobenzoyl-NH-] |
| 96 | [4-methylbenzoyl-NH-] |
| 97 | [thiophene-2-carbonyl-NH-] |
| 98 | [furan-2-carbonyl-NH-] |
| 99 | [2-amino-5-fluorobenzoyl-NH-] |
| 100 | [2-amino-6-fluorobenzoyl-NH-] |
| 101 | [pyridine-2-carbonyl-NH-] |
| 102 | NH₂ |

TABLE 3-continued
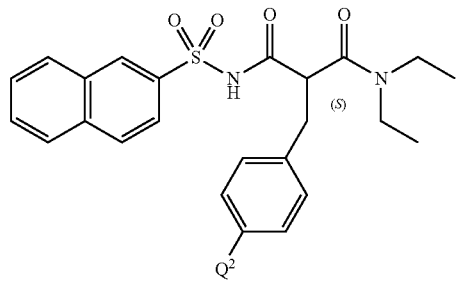 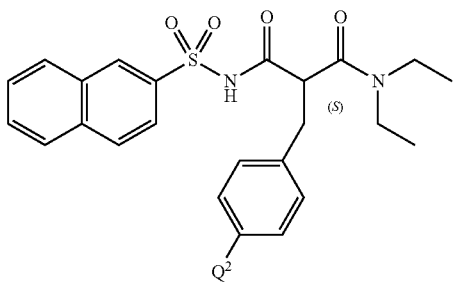
| Example | Q² |
|---|---|
| 103 | 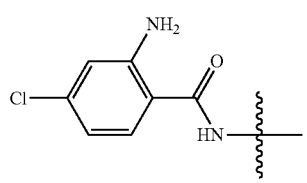 [SMILES: *NC(=O)c1ccc(Cl)cc1N] |
| 104 | 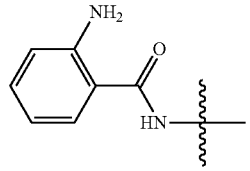 [SMILES: *NC(=O)c1ccccc1N] |
| 105 | 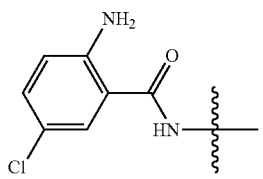 [SMILES: *NC(=O)c1cc(Cl)ccc1N] |
| 106 | 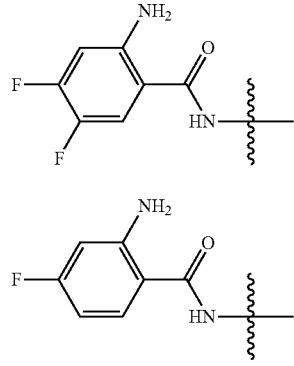 |
| 107 | 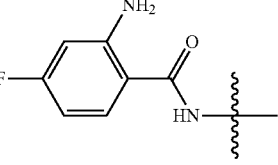 |
| 108 | 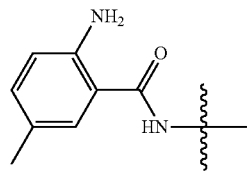 [SMILES: *NC(=O)c1cc(C)ccc1N] |
TABLE 4
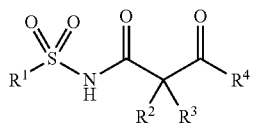
| Example | R¹ | R² | R³ | R⁴ |
|---|---|---|---|---|
| 109 | 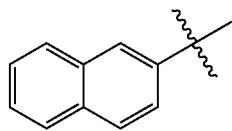 [SMILES: *c1ccc2ccccc2c1] | 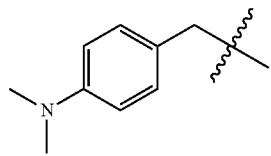 [SMILES: *Cc1ccc(N(C)C)cc1] | H | 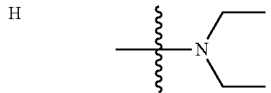 |
| 110 | ↑ | 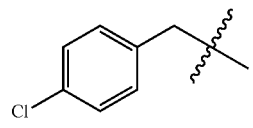 [SMILES: *Cc1ccc(Cl)cc1] | ↑ | ↑ |
| 111 | ↑ | 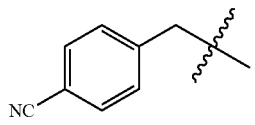 [SMILES: *Cc1ccc(C#N)cc1] | ↑ | ↑ |

US 10,071,099 B2
TABLE 4-continued
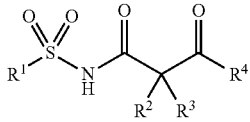
| Example | R¹ | R² | R³ | R⁴ |
|---|---|---|---|---|
| 112 | ↑ | 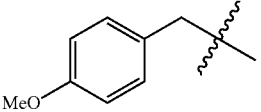 [SMILES: *Cc1ccc(OC)cc1] | ↑ | ↑ |
| 113 | ↑ | 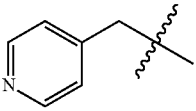 [SMILES: *Cc1ccncc1] | ↑ | ↑ |
| 114 | ↑ | 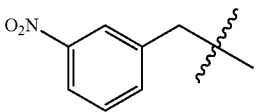 [SMILES: *Cc1cccc([N+](=O)[O-])c1] | ↑ | ↑ |
| 115 | ↑ | 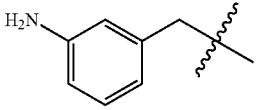 | ↑ | ↑ |
| 116 | ↑ | 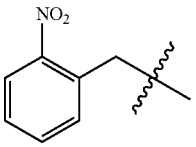 [SMILES: *Cc1ccccc1[N+](=O)[O-]] | ↑ | ↑ |
| 117 | ↑ | 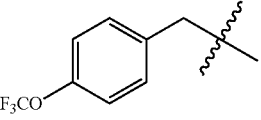 [SMILES: *Cc1ccc(OC(F)(F)F)cc1] | ↑ | ↑ |
| 118 | ↑ | 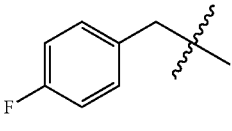 | ↑ | ↑ |
| 119 | ↑ | 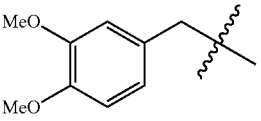 [SMILES: *Cc1ccc(OC)c(OC)c1] | ↑ | ↑ |
| 120 | ↑ | 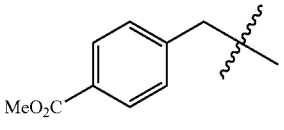 [SMILES: *Cc1ccc(C(=O)OC)cc1] | ↑ | ↑ |
| 121 | ↑ | 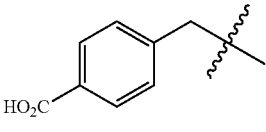 | ↑ | ↑ |
| 122 | ↑ | 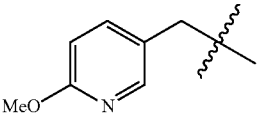 [SMILES: *Cc1ccc(OC)nc1] | ↑ | ↑ |

TABLE 4-continued
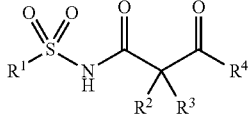
| Example | R¹ | R² | R³ | R⁴ |
|---|---|---|---|---|
| 123 | ↑ | 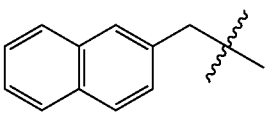 [SMILES: *Cc1ccc2ccccc2c1] | ↑ | ↑ |
| 124 | ↑ | 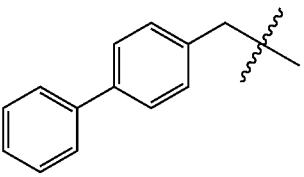 [SMILES: *Cc1ccc(-c2ccccc2)cc1] | ↑ | ↑ |
| 125 | ↑ | 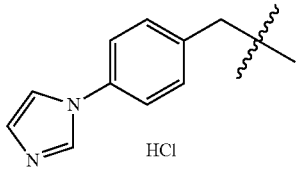 [SMILES: *Cc1ccc(-n2ccnc2)cc1 ; Cl] HCl | ↑ | ↑ |
| 126 | ↑ | 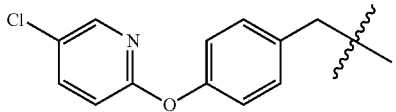 [SMILES: *Cc1ccc(Oc2ccc(Cl)cn2)cc1] | ↑ | ↑ |
| 127 | ↑ | 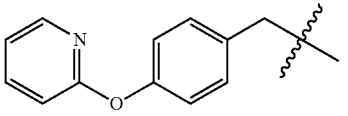 [SMILES: *Cc1ccc(Oc2ccccn2)cc1] | ↑ | ↑ |
| 128 | ↑ | 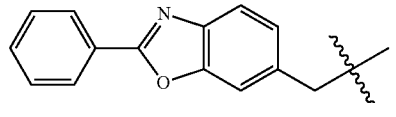 [SMILES: *Cc1ccc2nc(-c3ccccc3)oc2c1] | ↑ | ↑ |
| 129 | ↑ | 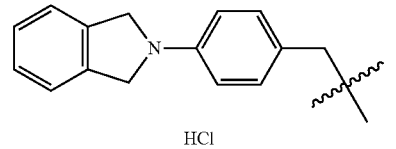 [SMILES: *Cc1ccc(N2Cc3ccccc3C2)cc1 ; Cl] HCl | ↑ | ↑ |
| 130 | ↑ | 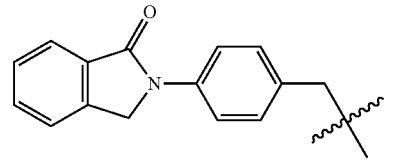 [SMILES: *Cc1ccc(N2Cc3ccccc3C2=O)cc1] | ↑ | ↑ |
| 131 | ↑ | 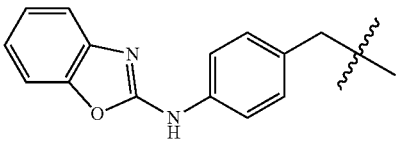 [SMILES: *Cc1ccc(Nc2nc3ccccc3o2)cc1] | ↑ | ↑ |

TABLE 4-continued

| Example | R¹ | R² | R³ | R⁴ |
|---|---|---|---|---|
| 132 | ↑ | (4-(phenylethynyl)phenyl)methyl | ↑ | ↑ |
| 133 | ↑ | (4-styrylphenyl)methyl | ↑ | ↑ |
| 134 | ↑ | (4-phenethylphenyl)methyl | ↑ | ↑ |
| 135 | ↑ | (4-(2,5-dioxo-3-phenylimidazolidin-1-yl)phenyl)methyl | ↑ | ↑ |
| 136 | ↑ | (4-(N-methylbenzamido)phenyl)methyl | ↑ | ↑ |
| 137 | ↑ | (4-benzamido-3,5-dimethylphenyl)methyl | ↑ | ↑ |
| 138 | ↑ | (4-(2-fluorobenzamido)-3,5-dimethylphenyl)methyl | ↑ | ↑ |
| 139 | ↑ | (4-(4-oxoquinazolin-3(4H)-yl)phenyl)methyl | ↑ | ↑ |

TABLE 4-continued
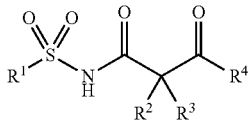
| Example | R¹ | R² | R³ | R⁴ |
|---|---|---|---|---|
| 140 | ↑ | 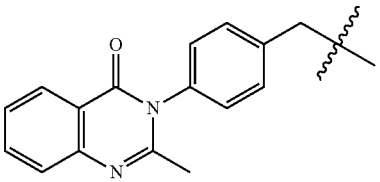 | ↑ | ↑ |
| 141 | ↑ | 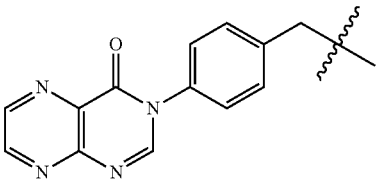 [SMILES: *Cc1ccc(-n2cnc3ccccc3c2=O)cc1] | ↑ | ↑ |
| 142 | ↑ | 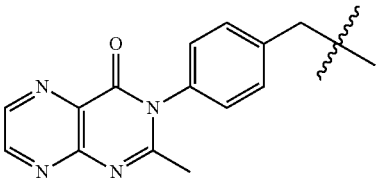 [SMILES: *Cc1ccc(-n2c(C)nc3nccnc3c2=O)cc1] | ↑ | ↑ |
| 143 | ↑ | 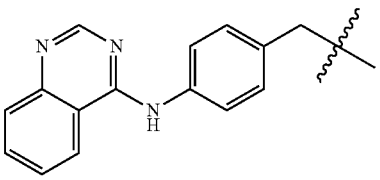 [SMILES: *Cc1ccc(Nc2ncnc3ccccc23)cc1] | ↑ | ↑ |
| 144 | ↑ | 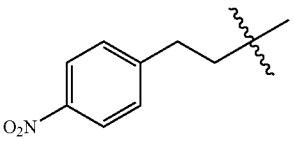 | ↑ | ↑ |
| 145 | ↑ | 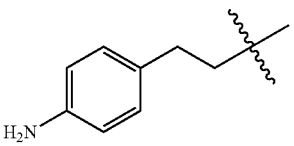 [SMILES: *CCc1ccc(N)cc1] | ↑ | ↑ |
| 146 | ↑ | 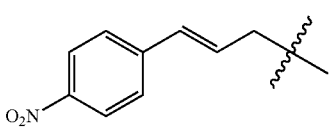 | ↑ | ↑ |
| 147 | ↑ | 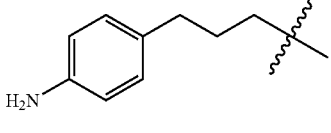 | ↑ | ↑ |

TABLE 4-continued
| Example | R¹ | R² | R³ | R⁴ |
|---|---|---|---|---|
| 148 | ↑ | 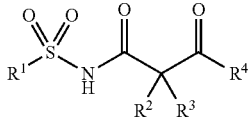 | ↑ | ↑ |
| 149 | ↑ | 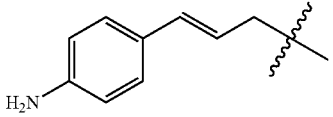 [SMILES: *C/C=C/c1ccc([N+](=O)[O-])cc1] | ↑ | ↑ |
| 150 | ↑ | 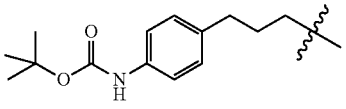 [SMILES: *CCCc1ccc(NC(=O)OC(C)(C)C)cc1] | ↑ | ↑ |
| 151 | ↑ | 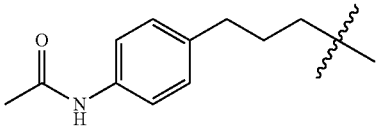 [SMILES: *CCCc1ccc(NC(C)=O)cc1] | ↑ | ↑ |
| 152 | ↑ | 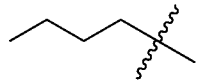 [SMILES: *CCCC] | ↑ | ↑ |
| 153 | ↑ |  | ↑ | ↑ |
| 154 | ↑ | 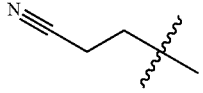 | ↑ | ↑ |
| 155 | ↑ | 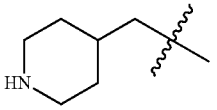 | ↑ | ↑ |
| 156 | ↑ | 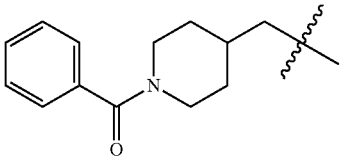 [SMILES: *CC1CCN(C(=O)c2ccccc2)CC1] | ↑ | ↑ |
| 157 | ↑ | 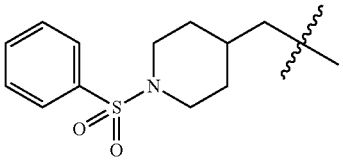 [SMILES: *CC1CCN(S(=O)(=O)c2ccccc2)CC1] | ↑ | ↑ |

TABLE 4-continued
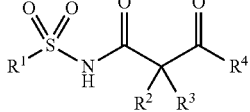
| Example | R¹ | R² | R³ | R⁴ |
|---|---|---|---|---|
| 158 | ↑ | 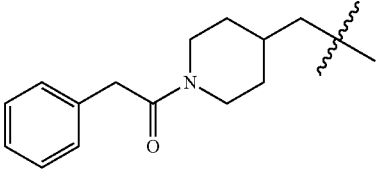 [SMILES: *CC1CCN(C(=O)Cc2ccccc2)CC1] | ↑ | ↑ |
| 159 | ↑ |  | ↑ | ↑ |
| 160 | ↑ |  | ↑ | ↑ |
| 161 | ↑ |  | ↑ | ↑ |
| 162 | ↑ | 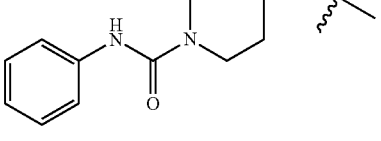 | ↑ | ↑ |
| 163 | ↑ |  | ↑ | ↑ |
| 164 | ↑ |  | ↑ | ↑ |
| 165 | ↑ |  | ↑ | ↑ |

TABLE 4-continued
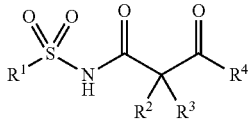
| Example | R¹ | R² | R³ | R⁴ |
|---|---|---|---|---|
| 166 | ↑ | 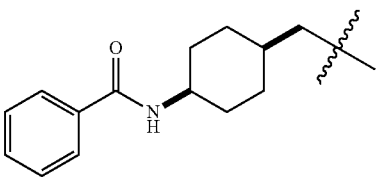 [SMILES: *C[C@H]1CC[C@@H](NC(=O)c2ccccc2)CC1] | ↑ | ↑ |
| 167 | ↑ | 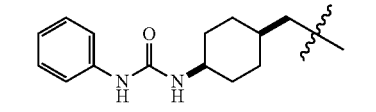 [SMILES: *C[C@H]1CC[C@@H](NC(=O)Nc2ccccc2)CC1] | ↑ | ↑ |
| 168 | ↑ | 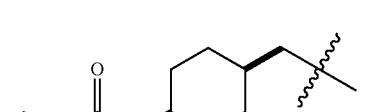 | ↑ | ↑ |
| 169 | ↑ | 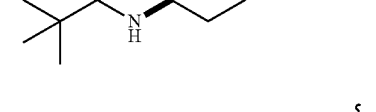 | ↑ | ↑ |
| 170 | ↑ | 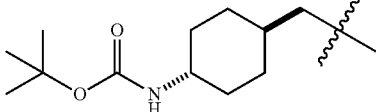<br>TFA | ↑ | ↑ |
| 171 | ↑ | 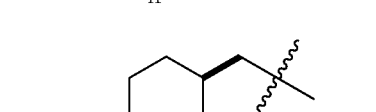 | ↑ | ↑ |
| 172 | ↑ | 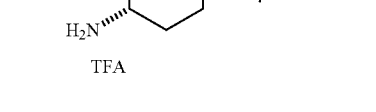 | ↑ | ↑ |
| 173 | ↑ | 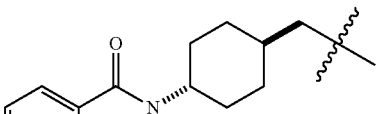 | ↑ | ↑ |

TABLE 4-continued

| Example | R¹ | R² | R³ | R⁴ |
|---|---|---|---|---|
| 174 | ↑ | (N-benzoyl-piperidin-4-yl)ethyl | ↑ | ↑ |
| 175 | ↑ | [N-(phenylcarbamoyl)-piperidin-4-yl]ethyl | ↑ | ↑ |
| 176 | ↑ | [N-(pyridine-3-carbonyl)-piperidin-4-yl]ethyl · HCl | ↑ | ↑ |
| 177 | 4-isobutylphenyl | benzyl | ↑ | ↑ |
| 178 | 4-methylphenyl | 4-nitrobenzyl | ↑ | ↑ |
| 179 | ↑ | 4-aminobenzyl | ↑ | ↑ |
| 180 | 4-chlorophenyl | 4-nitrobenzyl | ↑ | ↑ |
| 181 | ↑ | 4-aminobenzyl | ↑ | ↑ |
| 182 | 4-methoxyphenyl | 4-nitrobenzyl | ↑ | ↑ |

TABLE 4-continued
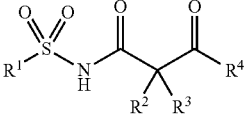
| Example | R¹ | R² | R³ | R⁴ |
|---|---|---|---|---|
| 183 | ↑ | 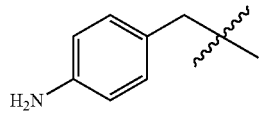 [SMILES: *Cc1ccc(N)cc1] | ↑ | ↑ |
| 184 | 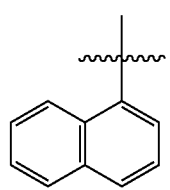 [SMILES: *c1cccc2ccccc12] | 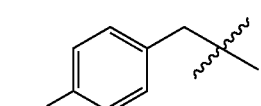 | ↑ | ↑ |
| 185 | ↑ | 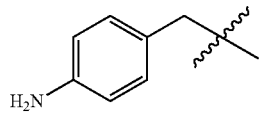 | ↑ | ↑ |
| 186 | 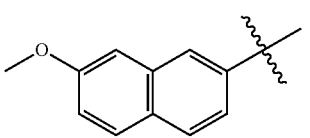 [SMILES: *c1ccc2ccc(OC)cc2c1] | 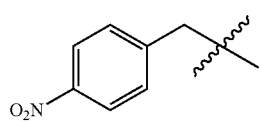 | ↑ | ↑ |
| 187 | ↑ | 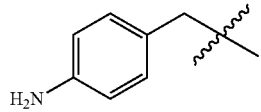 | ↑ | ↑ |
| 188 | 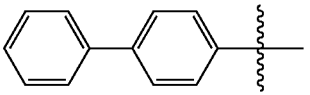 [SMILES: *c1ccc(-c2ccccc2)cc1] | 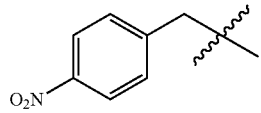 | ↑ | ↑ |
| 189 | ↑ | 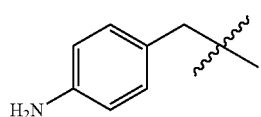 | ↑ | ↑ |
| 190 | 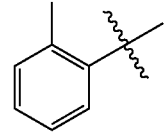 [SMILES: *c1ccccc1C] | 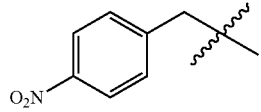 [SMILES: *Cc1ccc([N+](=O)[O-])cc1] | ↑ | ↑ |
| 191 | ↑ | 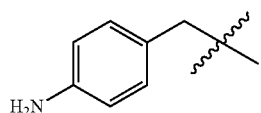 | ↑ | ↑ |
| 192 | 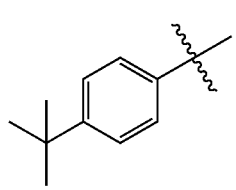 [SMILES: *c1ccc(C(C)(C)C)cc1] | 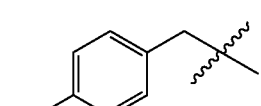 | ↑ | ↑ |

TABLE 4-continued

| Example | R¹ | R² | R³ | R⁴ |
|---|---|---|---|---|
| 193 | ↑ | 4-H₂N-C₆H₄-CH₂- | ↑ | ↑ |
| 194 | 2-thienyl- | 4-O₂N-C₆H₄-CH₂- | ↑ | ↑ |
| 195 | ↑ | 4-H₂N-C₆H₄-CH₂- | ↑ | ↑ |
| 196 | 4-CF₃-C₆H₄- | 4-O₂N-C₆H₄-CH₂- | ↑ | ↑ |
| 197 | ↑ | 4-H₂N-C₆H₄-CH₂- | ↑ | ↑ |
| 198 | 5-(dimethylamino)naphthalen-1-yl | 4-O₂N-C₆H₄-CH₂- | ↑ | ↑ |
| 199 | ↑ | 4-H₂N-C₆H₄-CH₂- | ↑ | ↑ |
| 200 | (E)-styryl- | 4-O₂N-C₆H₄-CH₂- | ↑ | ↑ |
| 201 | ↑ | 4-H₂N-C₆H₄-CH₂- | ↑ | ↑ |

TABLE 4-continued
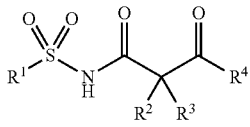
| Example | R¹ | R² | R³ | R⁴ |
| --- | --- | --- | --- | --- |
| 202 | ↑ | 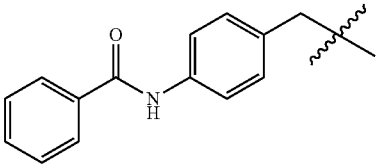 [SMILES: *Cc1ccc(NC(=O)c2ccccc2)cc1] | ↑ | ↑ |
| 203 |  | ↑ | ↑ | ↑ |
| 204 |  | 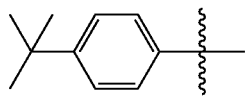 | ↑ | ↑ |
| 205 | ↑ | 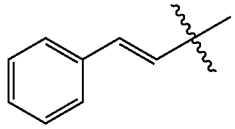 [SMILES: */C=C/c1ccccc1] | ↑ | ↑ |
| 206 | ↑ | 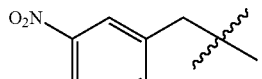 | ↑ | ↑ |
| 207 | ↑ | 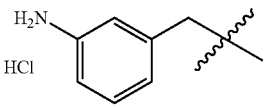 | ↑ | ↑ |
| 208 | ↑ | 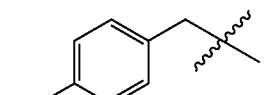 | ↑ | ↑ |
| 209 | ↑ | 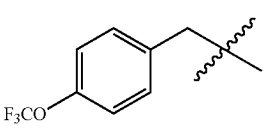 [SMILES: *Cc1ccc(OC(F)(F)F)cc1] | ↑ | ↑ |
| 210 | ↑ | 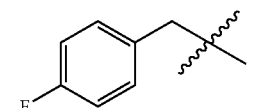 | ↑ | ↑ |
| 211 | ↑ | 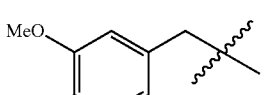 | ↑ | ↑ |

TABLE 4-continued

| Example | R¹ | R² | R³ | R⁴ |
|---|---|---|---|---|
| 212 | ↑ | 6-methoxypyridin-3-ylmethyl | ↑ | ↑ |
| 213 | ↑ | 4-(5-chloropyridin-2-yloxy)phenylmethyl | ↑ | ↑ |
| 214 | ↑ | cyclopropylmethyl | ↑ | ↑ |
| 215 | ↑ | propargyl | ↑ | ↑ |
| 216 | ↑ | 4-methoxybenzyl | ↑ | ↑ |
| 217 | ↑ | 4-nitrophenethyl | ↑ | ↑ |
| 218 | ↑ | 4-aminophenethyl | ↑ | ↑ |
| 219 | phenethyl | 4-aminobenzyl | ↑ | ↑ |
| 220 | ↑ | 4-benzamidophenylmethyl | ↑ | ↑ |
| 221 | ↑ | 4-methoxybenzyl | ↑ | ↑ |
| 222 | ↑ | 4-aminophenethyl | ↑ | ↑ |

TABLE 4-continued

| Example | R¹ | R² | R³ | R⁴ |
|---|---|---|---|---|
| 223 | 4-phenoxyphenyl | 4-nitrobenzyl | ↑ | ↑ |
| 224 | ↑ | 4-aminobenzyl | ↑ | ↑ |
| 225 | 5-isobutylthiophen-2-yl | 4-nitrobenzyl | ↑ | ↑ |
| 226 | ↑ | 4-aminobenzyl | ↑ | ↑ |
| 227 | naphthalen-2-yl | 4-cyanobenzyl | ↑ | cyclohexylamino |
| 228 | ↑ | ↑ | ↑ | 4-(4-nitrophenyl)piperazin-1-yl |
| 229 | ↑ | ↑ | ↑ | N-ethylanilino |
| 230 | ↑ | ↑ | ↑ | 4-(5-cyanopyridin-2-yl)piperazin-1-yl |
| 231 | ↑ | ↑ | ↑ | 4-(pyridin-4-yl)piperazin-1-yl |
| 232 | ↑ | 4-methoxybenzyl | ↑ | N-ethylanilino |

TABLE 4-continued
| Example | R¹ | R² | R³ | R⁴ |
|---|---|---|---|---|
| 233 | ↑ | ↑ | ↑ | 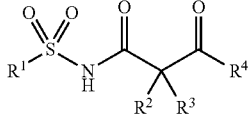 |
| 234 | ↑ | ↑ | ↑ | 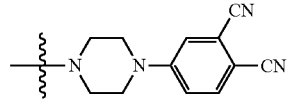 [SMILES: *N1CCN(c2ccc(C#N)c(C#N)c2)CC1] |
| 235 | ↑ | 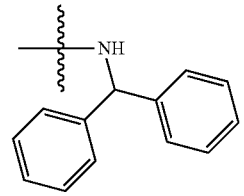 [SMILES: *NC(c1ccccc1)c1ccccc1] | ↑ | 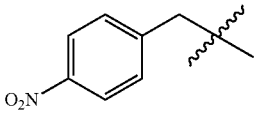 |
| 236 | ↑ | 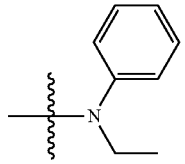 [SMILES: *N(CC)c1ccccc1] | ↑ | ↑ |
| 237 | ↑ | 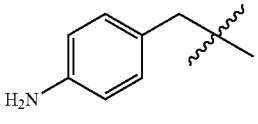 | ↑ | 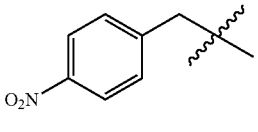 |
| 238 | ↑ | 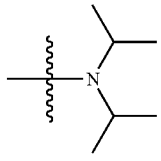 [SMILES: *N(C(C)C)C(C)C] | ↑ | ↑ |
| 239 | ↑ | ↑ | ↑ | 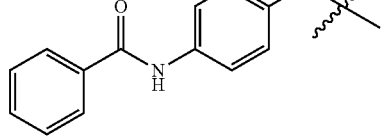 |
| 240 | ↑ | ↑ | ↑ | 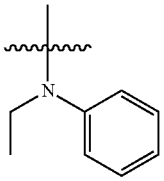 [SMILES: *N(CC)c1ccccc1] |
| 241 | ↑ | ↑ | ↑ | 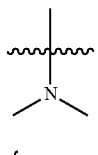 |

TABLE 4-continued

| Example | R¹ | R² | R³ | R⁴ |
|---|---|---|---|---|
| 242 | ↑ | ↑ | ↑ | -N(propyl)₂ |
| 243 | ↑ | ↑ | ↑ | -N(pentyl)₂ |
| 244 | ↑ | ↑ | ↑ | pyrrolidin-1-yl |
| 245 | ↑ | ↑ | ↑ | piperidin-1-yl |
| 246 | ↑ | ↑ | ↑ | morpholin-4-yl |
| 247 | ↑ | ↑ | ↑ | 4-methylpiperazin-1-yl |
| 248 | ↑ | ↑ | ↑ | N-ethyl-N-(4-fluorophenyl)amino |
| 249 | ↑ | ↑ | ↑ | N-isopropyl-N-(4-fluorophenyl)amino |
| 250 | ↑ | ↑ | ↑ | N-isopropyl-N-(3-trifluoromethylphenyl)amino |
| 251 | ↑ | ↑ | ↑ | N-isopropyl-N-(pyridin-3-yl)amino |

TABLE 4-continued

| Example | R¹ | R² | R³ | R⁴ |
|---|---|---|---|---|
| 252 | ↑ | 4-O₂N-C₆H₄-CH₂- | ↑ | morpholin-4-yl |
| 253 | ↑ | 4-H₂N-C₆H₄-CH₂- | ↑ | morpholin-4-yl |
| 254 | ↑ | 4-O₂N-C₆H₄-CH₂- | ↑ | 4-methylpiperazin-1-yl |
| 255 | ↑ | 4-H₂N-C₆H₄-CH₂- | ↑ | 4-methylpiperazin-1-yl |
| 256 | ↑ | 4-O₂N-C₆H₄-CH₂- | ↑ | N-methyl-N-(2-hydroxyethyl)amino |
| 257 | ↑ | 4-H₂N-C₆H₄-CH₂- | ↑ | N-methyl-N-(2-hydroxyethyl)amino |
| 258 | ↑ | 4-O₂N-C₆H₄-CH₂- | ↑ | benzhydrylamino |
| 259 | ↑ | 4-H₂N-C₆H₄-CH₂- | ↑ | benzhydrylamino |
| 260 | ↑ | 4-O₂N-C₆H₄-CH₂- | ↑ | ethylamino |
| 261 | ↑ | 4-H₂N-C₆H₄-CH₂- | ↑ | ethylamino |

TABLE 4-continued

| Example | R¹ | R² | R³ | R⁴ |
|---|---|---|---|---|
| 262 | ↑ | 4-O₂N-C₆H₄-CH₂- | ↑ | spiro[piperidine-4,1'-indan]-3'-one-1-yl |
| 263 | ↑ | 4-H₂N-C₆H₄-CH₂- | ↑ | spiro[piperidine-4,1'-indan]-3'-one-1-yl |
| 264 | ↑ | 4-H₂N-C₆H₄-CH₂- | ↑ | N,N-dipentyl |
| 265 | PhCH=CH-CH₂- | 4-MeO-C₆H₄-CH₂- | ↑ | N-ethyl-N-phenyl |
| 266 | PhCH₂CH₂-CH- | 4-MeO-C₆H₄-CH₂- | ↑ | ↑ |
| 267 | 2-naphthyl | 4-Cl-C₆H₄-CH₂- | ↑ | ↑ |
| 268 | ↑ | 4-pyridyl-CH₂- | ↑ | ↑ |
| 269 | ↑ | 4-F₃CO-C₆H₄-CH₂- | ↑ | ↑ |
| 270 | PhCH=CH-CH₂- | 4-F₃CO-C₆H₄-CH₂- | ↑ | ↑ |

TABLE 4-continued

Structure header: R¹-S(O)₂-NH-C(O)-C(R²)(R³)-C(O)-R⁴

| Example | R¹ | R² | R³ | R⁴ |
|---|---|---|---|---|
| 271 | naphthalen-2-yl | 3,4-dimethoxybenzyl | ↑ | ↑ |
| 272 | (E)-styryl | 3,4-dimethoxybenzyl | ↑ | ↑ |
| 273 | naphthalen-2-yl | benzo[d][1,3]dioxol-5-ylmethyl | ↑ | ↑ |
| 274 | (E)-styryl | benzo[d][1,3]dioxol-5-ylmethyl | ↑ | ↑ |
| 275 | naphthalen-2-yl | 4-(methoxycarbonyl)benzyl | ↑ | ↑ |
| 276 | ↑ | 4-carboxybenzyl | ↑ | ↑ |
| 277 | (E)-styryl | 4-(methoxycarbonyl)benzyl | ↑ | ↑ |
| 278 | ↑ | 4-carboxybenzyl | ↑ | ↑ |
| 279 | naphthalen-2-yl | (6-methoxypyridin-3-yl)methyl | ↑ | ↑ |
| 280 | (E)-styryl | ↑ | ↑ | ↑ |

TABLE 4-continued
| Example | R¹ | R² | R³ | R⁴ |
|---|---|---|---|---|
| 281 | ↑ | 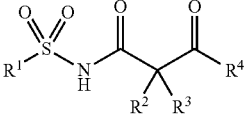 | ↑ | ↑ |
| 282 | ↑ | 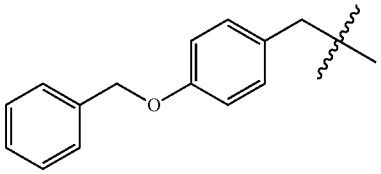 [SMILES: *Cc1ccc(OCc2ccccc2)cc1] | ↑ | ↑ |
| 283 | ↑ | 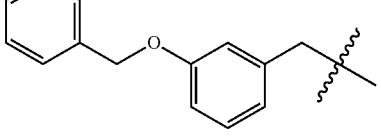 | ↑ | ↑ |
| 284 | 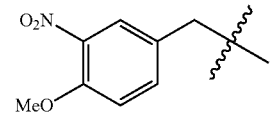 [SMILES: *Cc1ccc(OC)c([N+](=O)[O-])c1] | ↑ | ↑ | ↑ |
| 285 | ↑ | 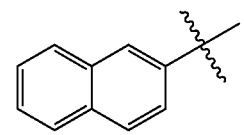 [SMILES: *c1ccc2ccccc2c1] | ↑ | ↑ |
| 286 | 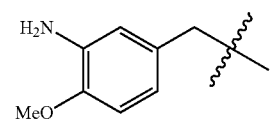 [SMILES: *Cc1ccc(OC)c(N)c1] | 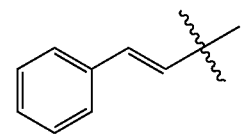 [SMILES: */C=C/c1ccccc1] | ↑ | ↑ |
| 287 | 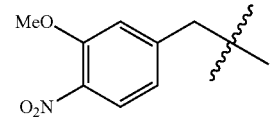 | ↑ | ↑ | ↑ |
| 288 | ↑ | 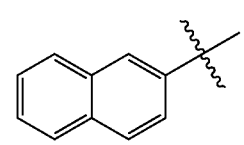 | ↑ | ↑ |
| 289 | 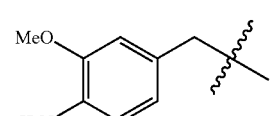 | 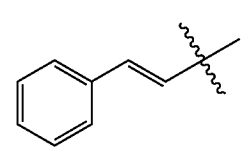 [SMILES: */C=C/c1ccccc1] | ↑ | ↑ |
| 290 | ↑ | 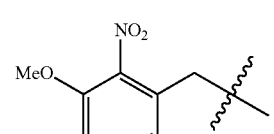 | ↑ | ↑ |

TABLE 4-continued

| Example | R¹ | R² | R³ | R⁴ |
|---|---|---|---|---|
| 291 | ↑ | 3-amino-4-methylbenzyl | ↑ | ↑ |
| 292 | ↑ | 3-(benzoylamino)-4-methylbenzyl | ↑ | ↑ |
| 293 | 2-naphthyl | 3-nitro-4-methylbenzyl | ↑ | ↑ |
| 294 | ↑ | 3-amino-4-methylbenzyl | ↑ | ↑ |
| 295 | ↑ | 3-(benzoylamino)-4-methylbenzyl | ↑ | ↑ |
| 296 | ↑ | 4-fluorobenzyl | ↑ | ↑ |
| 297 | (E)-cinnamyl | ↑ | ↑ | ↑ |
| 298 | ↑ | 3-(4-fluorophenoxy)benzyl | ↑ | ↑ |
| 299 | ↑ | 3-(1H-imidazol-1-ylmethyl)benzyl | ↑ | ↑ |
| 300 | ↑ | 3-((2-methyl-1H-benzimidazol-1-yl)methyl)benzyl | ↑ | ↑ |

TABLE 4-continued
| Example | R¹ | R² | R³ | R⁴ |
|---|---|---|---|---|
| 301 | ↑ | 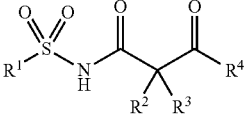 H₂N-C₆H₄-CH₂CH₂- | ↑ | ↑ |
| 303 | 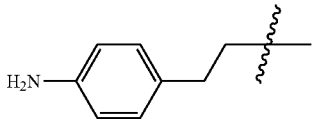 [SMILES: *CCc1ccc(N)cc1] Ph-CH₂CH₂- | 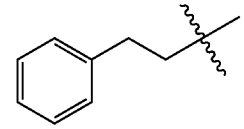 [SMILES: *CCc1ccccc1] H₂N-C₆H₄-CH₂CH₂- | ↑ | ↑ |
| 304 | 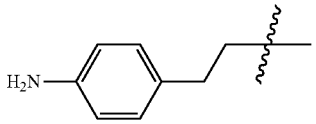 2-naphthyl | 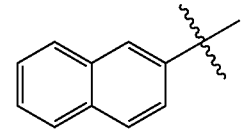 [SMILES: *c1ccc2ccccc2c1] O₂N-C₆H₄-CH₂CH₂- | ↑ | ↑ |
| 305 | ↑ | 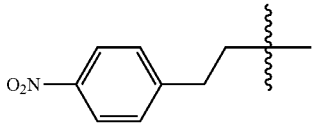 [SMILES: *CCc1ccc([N+](=O)[O-])cc1] H₂N-C₆H₄-CH₂CH₂- | ↑ | ↑ |
| 306 | 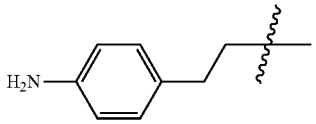 Ph-CH=CH- | 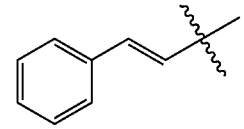 [SMILES: */C=C/c1ccccc1] HC≡C-CH₂- | ↑ | ↑ |
| 307 | 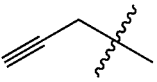 [SMILES: *CC#C] 2-naphthyl | ↑ | ↑ | ↑ |
| 308 | 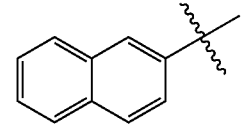 [SMILES: *c1ccc2ccccc2c1] Ph-CH=CH- | 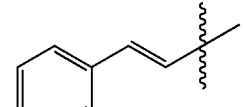 4-F-C₆H₄-CH₂- | ↑ | 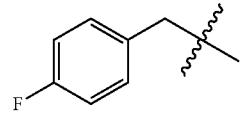 [SMILES: *Cc1ccc(F)cc1] N(Et)(4-F-C₆H₄)- |
| 309 | ↑ | ↑ | ↑ | 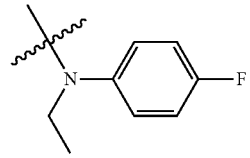 [SMILES: *N(CC)c1ccc(F)cc1] N(iPr)(4-F-C₆H₄)- |
| 310 | ↑ | 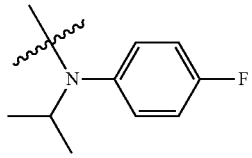 [SMILES: *N(c1ccc(F)cc1)C(C)C] 3-F-C₆H₄-CH₂- | ↑ | ↑ |
| 311 | 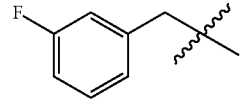 [SMILES: *Cc1cccc(F)c1] 2-naphthyl | ↑ | ↑ | ↑ |

TABLE 4-continued
| Example | R¹ | R² | R³ | R⁴ |
|---|---|---|---|---|
| 312 | 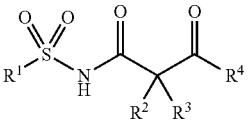 | 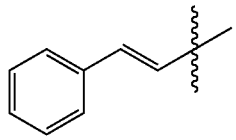 [SMILES: */C=C/c1ccccc1] | ↑ | ↑ |
| 313 | 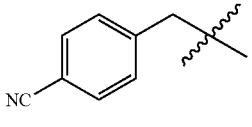 [SMILES: *Cc1ccc(C#N)cc1] | ↑ | ↑ | ↑ |
| 314 | 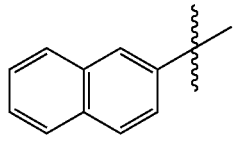 [SMILES: *c1ccc2ccccc2c1] | 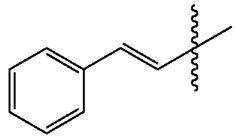 [SMILES: */C=C/c1ccccc1] | ↑ | ↑ |
| 315 | 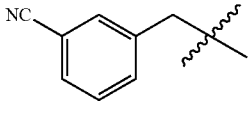 [SMILES: *Cc1cccc(C#N)c1] | ↑ | ↑ | ↑ |
| 316 | ↑ | 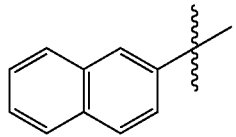 [SMILES: *c1ccc2ccccc2c1] | ↑ | ↑ |
| 317 | ↑ | ↑ | ↑ | 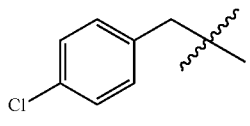 [SMILES: *Cc1ccc(Cl)cc1] HCl |
| 318 | 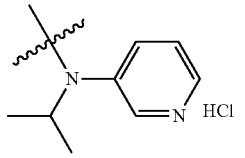 [SMILES: *N(c1cccnc1)C(C)C ; Cl] | 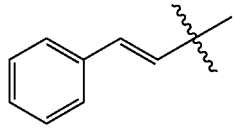 [SMILES: */C=C/c1ccccc1] | ↑ | 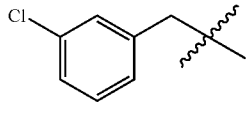 [SMILES: *Cc1cccc(Cl)c1] |
| 319 | 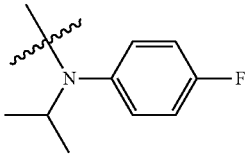 [SMILES: *N(c1ccc(F)cc1)C(C)C] | ↑ | ↑ | ↑ |
| 320 | 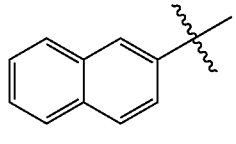 [SMILES: *c1ccc2ccccc2c1] | 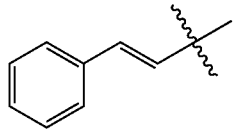 [SMILES: */C=C/c1ccccc1] | ↑ | ↑ |

TABLE 4-continued
| Example | R¹ | R² | R³ | R⁴ |
|---|---|---|---|---|
| 321 | 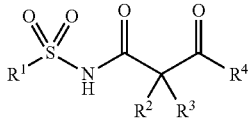 | ↑ | ↑ | ↑ |
| 322 | 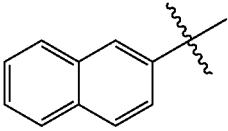 [SMILES: *c1ccc2ccccc2c1] | 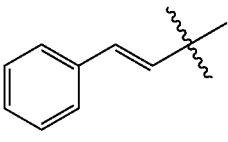 [SMILES: */C=C/c1ccccc1] | ↑ | 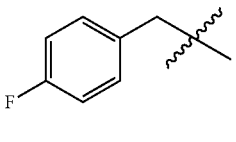 [SMILES: *Cc1ccc(F)cc1] |
| 323 | ↑ | ↑ | ↑ | 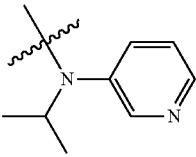 [SMILES: *N(c1cccnc1)C(C)C] |
| 324 | ↑ | ↑ | ↑ | 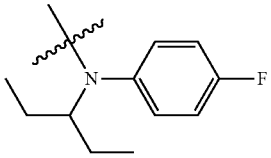 [SMILES: *N(c1ccc(F)cc1)C(CC)CC] |
| 325 | ↑ | ↑ | ↑ | 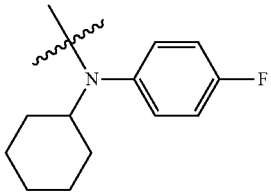 [SMILES: *N(c1ccc(F)cc1)C1CCCCC1] |
| 326 | ↑ | ↑ | ↑ | 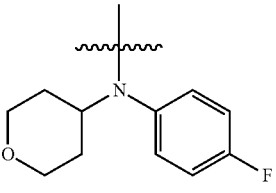 [SMILES: *N(c1ccc(F)cc1)C1CCOCC1] |
| 327 | ↑ | ↑ | ↑ | 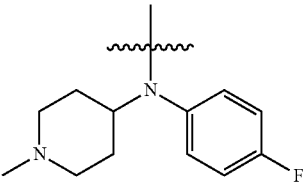 [SMILES: *N(c1ccc(F)cc1)C1CCN(C)CC1] |

TABLE 4-continued
| Example | R¹ | R² | R³ | R⁴ |
|---|---|---|---|---|
| 328 | ↑ | ↑ | ↑ | 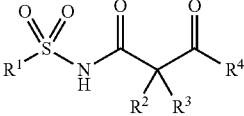 |
| 329 | ↑ | ↑ | ↑ | 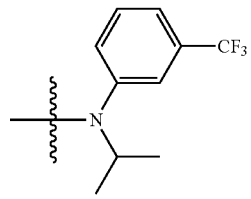 [SMILES: *N(c1cccc(C(F)(F)F)c1)C(C)C] |
| 330 | ↑ | ↑ | ↑ | 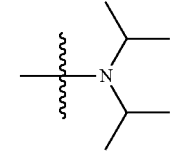 [SMILES: *N(C(C)C)C(C)C] |
| 331 | 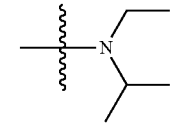 | 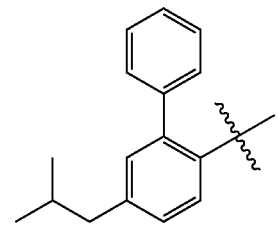 [SMILES: *c1ccc(CC(C)C)cc1-c1ccccc1] | ↑ | 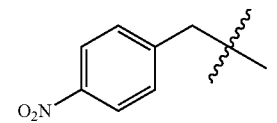 |
| 332 | ↑ | 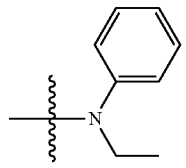 [SMILES: *N(CC)c1ccccc1] | ↑ | ↑ |
| 333 | 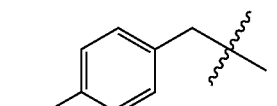 | 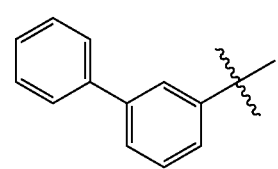 [SMILES: *c1cccc(-c2ccccc2)c1] | ↑ | ↑ |
| 334 | ↑ | 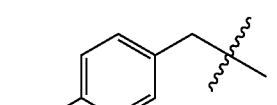 | ↑ | ↑ |
| 335 | 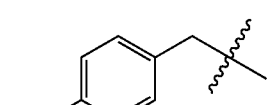 | 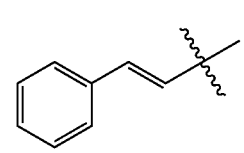 [SMILES: */C=C/c1ccccc1] | ↑ | ↑ |

TABLE 4-continued

| Example | R¹ | R² | R³ | R⁴ |
|---|---|---|---|---|
| 336 | ↑ | 4-aminobenzyl | ↑ | ↑ |
| 337 | ↑ | 4-(benzoylamino)benzyl | ↑ | ↑ |
| 338 | phenethyl | 4-aminobenzyl | ↑ | ↑ |
| 339 | benzyl | 4-nitrobenzyl | ↑ | ↑ |
| 340 | ↑ | 4-aminobenzyl | ↑ | ↑ |
| 341 | n-propyl | 4-nitrobenzyl | ↑ | ↑ |
| 342 | ↑ | 4-aminobenzyl | ↑ | ↑ |
| 343 | 2-naphthyl | 3-bromobenzyl | ↑ | ↑ |
| 344 | styryl | ↑ | ↑ | ↑ |
| 345 | ↑ | 4-bromobenzyl | ↑ | ↑ |

US 10,071,099 B2
TABLE 4-continued
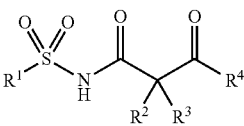
| Example | R¹ | R² | R³ | R⁴ |
|---|---|---|---|---|
| 346 | 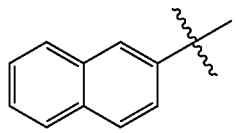 [SMILES: *c1ccc2ccccc2c1] | ↑ | ↑ | ↑ |
| 347 | 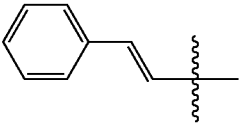 [SMILES: */C=C/c1ccccc1] | 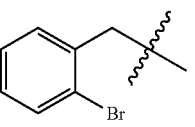 [SMILES: *Cc1ccccc1Br] | ↑ | ↑ |
| 348 | 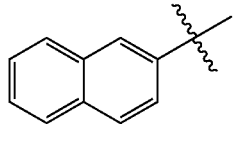 [SMILES: *c1ccc2ccccc2c1] | ↑ | ↑ | ↑ |
| 349 | 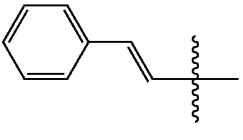 [SMILES: */C=C/c1ccccc1] | 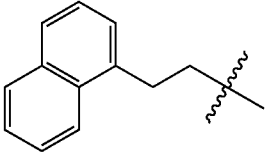 [SMILES: *CCc1cccc2ccccc12] | ↑ | ↑ |
| 350 | 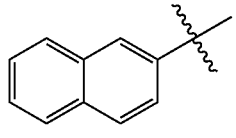 [SMILES: *c1ccc2ccccc2c1] | ↑ | ↑ | ↑ |
| 351 | 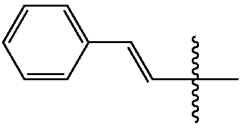 | 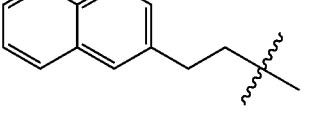 | ↑ | ↑ |
| 352 | 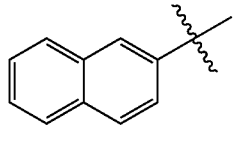 [SMILES: *c1ccc2ccccc2c1] | ↑ | ↑ | ↑ |
| 353 | 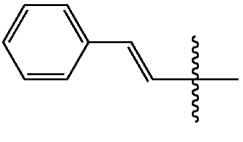 [SMILES: */C=C/c1ccccc1] | 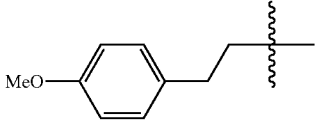 [SMILES: *CCc1ccc(OC)cc1] | ↑ | ↑ |
| 354 | 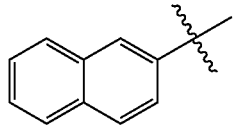 [SMILES: *c1ccc2ccccc2c1] | ↑ | ↑ | ↑ |
| 355 | 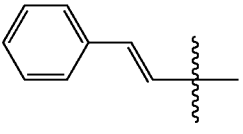 | 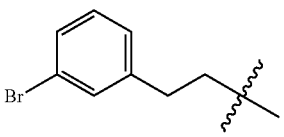 [SMILES: *CCc1cccc(Br)c1] | ↑ | ↑ |

TABLE 4-continued

| Example | R¹ | R² | R³ | R⁴ |
|---|---|---|---|---|
| 356 | 2-naphthyl | ↑ | ↑ | ↑ |
| 357 | styryl | 4-bromophenethyl | ↑ | ↑ |
| 358 | 2-naphthyl | ↑ | ↑ | ↑ |
| 359 | styryl | (3-biphenyl)methyl | ↑ | ↑ |
| 360 | 2-naphthyl | ↑ | ↑ | ↑ |
| 361 | styryl | (4'-methoxy-4-biphenyl)methyl | ↑ | ↑ |
| 362 | 2-naphthyl | ↑ | ↑ | ↑ |
| 363 | phenethyl | ↑ | ↑ | ↑ |
| 364 | styryl | (2-biphenyl)methyl | ↑ | ↑ |

TABLE 4-continued
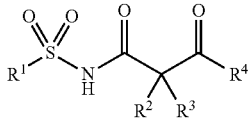
| Example | R¹ | R² | R³ | R⁴ |
| --- | --- | --- | --- | --- |
| 365 | 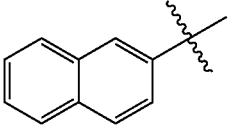 [SMILES: *c1ccc2ccccc2c1] | ↑ | ↑ | ↑ |
| 366 | 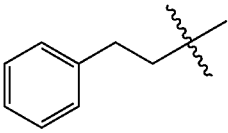 [SMILES: *CCc1ccccc1] | ↑ | ↑ | ↑ |
| 367 | 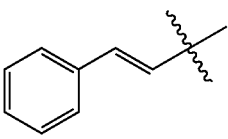 [SMILES: */C=C/c1ccccc1] | 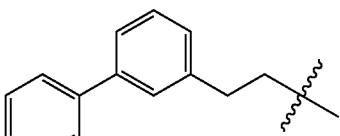 | ↑ | ↑ |
| 368 | ↑ | 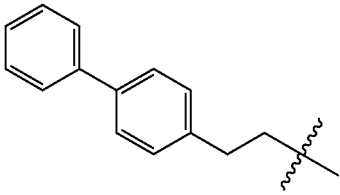 [SMILES: *CCc1ccc(-c2ccccc2)cc1] | ↑ | ↑ |
| 369 | 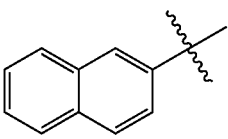 [SMILES: *c1ccc2ccccc2c1] | ↑ | ↑ | ↑ |
| 370 | ↑ | 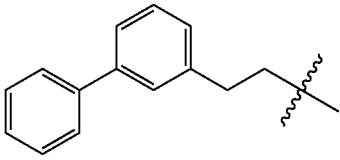 [SMILES: *CCc1cccc(-c2ccccc2)c1] | ↑ | ↑ |
| 371 | 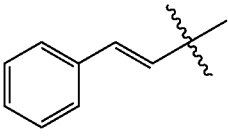 [SMILES: */C=C/c1ccccc1] | 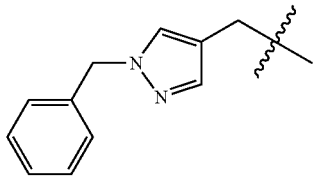 [SMILES: *Cc1cnn(Cc2ccccc2)c1] | ↑ | ↑ |
| 372 | ↑ | 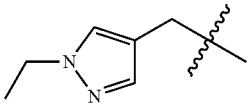 [SMILES: *Cc1cnn(CC)c1] | ↑ | ↑ |
| 373 | ↑ | 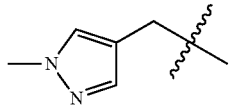 [SMILES: *Cc1cnn(C)c1] | ↑ | ↑ |

TABLE 4-continued
| Example | R¹ | R² | R³ | R⁴ |
|---|---|---|---|---|
| 374 | ↑ | 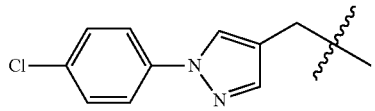 [SMILES: *Cc1cnn(-c2ccc(Cl)cc2)c1] | ↑ | ↑ |
| 375 | ↑ |  | ↑ | ↑ |
| 376 | ↑ |  | ↑ | ↑ |
| 377 | ↑ |  | ↑ | ↑ |
| 378 | ↑ |  | ↑ | ↑ |
| 379 | ↑ |  HCl | ↑ | ↑ |
| 380 | ↑ |  HCl | ↑ | ↑ |
| 381 | ↑ |  | ↑ |  |

TABLE 4-continued

| Example | R¹ | R² | R³ | R⁴ |
|---|---|---|---|---|
| 382 | ↑ | (3-pyridylmethyl-pyrazolyl-CH₂-)·HCl | ↑ | ↑ |
| 383 | ↑ | (2-aminobenzyl-pyrazolyl-CH₂-) | ↑ | N-ethyl-N-phenylamino- |
| 384 | ↑ | (3-aminobenzyl-pyrazolyl-CH₂-) | ↑ | ↑ |
| 385 | ↑ | (benzyl-pyrazolyl-CH₂-) | ↑ | N,N-diethylamino- |
| 386 | ↑ | (4-fluorobenzyl-pyrazolyl-CH₂-) | ↑ | ↑ |
| 387 | ↑ | (4-chlorobenzyl-pyrazolyl-CH₂-) | ↑ | ↑ |
| 388 | ↑ | (6-chloro-3-pyridylmethyl-pyrazolyl-CH₂-) | ↑ | ↑ |
| 389 | 2-naphthyl | (benzyl-pyrazolyl-CH₂-) | ↑ | ↑ |

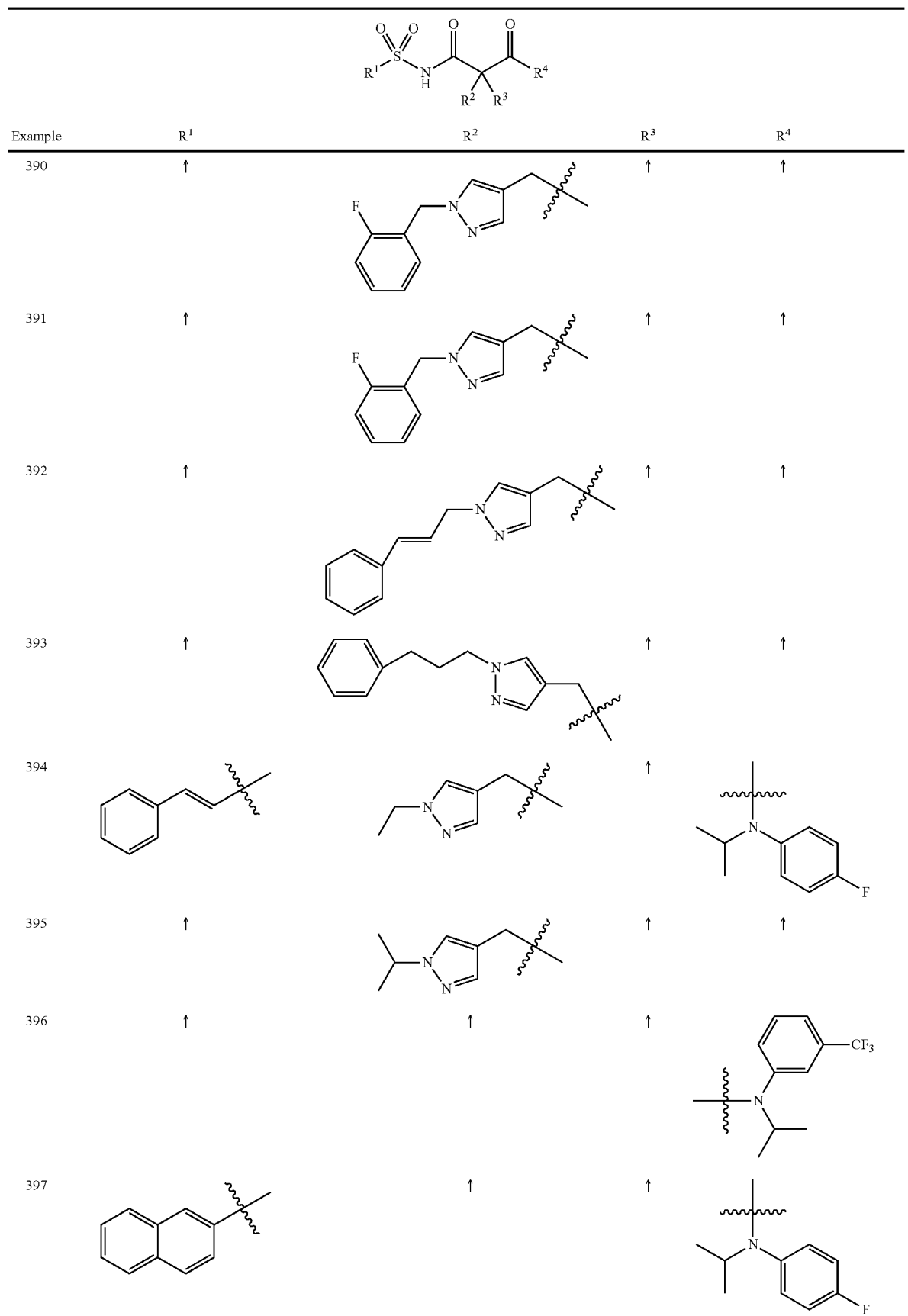

TABLE 4-continued

| Example | R¹ | R² | R³ | R⁴ |
|---|---|---|---|---|
| 398 | thiazol-2-yl-CH=CH-CH(Me)- | 1-benzyl-1H-pyrazol-4-yl-CH₂-C(Me)- | ↑ | N-ethyl-N-phenyl- |
| 399 | pyridin-3-yl-CH=CH-CH(Me)- | ↑ | ↑ | ↑ |
| 400 | 4-fluorophenyl-CH=CH-CH(Me)- | ↑ | ↑ | ↑ |
| 401 | phenyl-CH=CH-CH(Me)- | 4-methylphenyl- | ↑ | ↑ |
| 402 | 4-methylphenyl- | 1-benzyl-1H-pyrazol-4-yl-CH₂-C(Me)- | ↑ | ↑ |
| 403 | 4-chlorophenyl- | ↑ | ↑ | ↑ |
| 404 | phenyl-CH=CH-CH(Me)- | 1-(3-methylbut-2-enyl)-1H-pyrazol-4-yl-CH₂-C(Me)- | ↑ | N-ethyl-N-(4-fluorophenyl)- |
| 405 | phenyl-CH=CH-CH(Me)- | 1-benzyl-1H-pyrazol-4-yl-CH₂-C(Me)- | ↑ | N-ethyl-N-(naphthalen-1-yl)- |

TABLE 4-continued
| Example | R¹ | R² | R³ | R⁴ |
|---|---|---|---|---|
| 406 | ↑ | ↑ | ↑ | 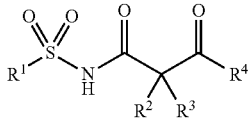 |
| 407 | ↑ | ↑ | ↑ | 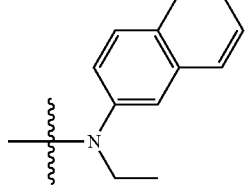 |
| 408 | ↑ | ↑ | ↑ | 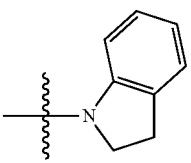 [SMILES: *N1CCc2ccccc21] |
| 409 | ↑ | ↑ | ↑ | 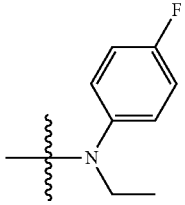 [SMILES: *N(CC)c1ccc(F)cc1] |
| 410 | ↑ | ↑ | ↑ | 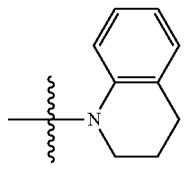 [SMILES: *N1CCCc2ccccc21] HCl |
| 411 | ↑ | ↑ | ↑ | 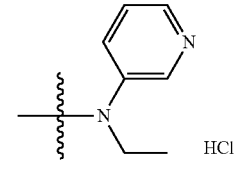 |
| 412 | ↑ | ↑ | ↑ | 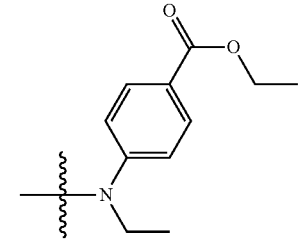 [SMILES: *N(CC)c1ccc(C(=O)OCC)cc1] |

TABLE 4-continued
| Example | R¹ | R² | R³ | R⁴ |
|---|---|---|---|---|
| 413 | ↑ | ↑ | ↑ | 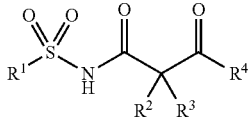 |
| 414 | ↑ | ↑ | ↑ | 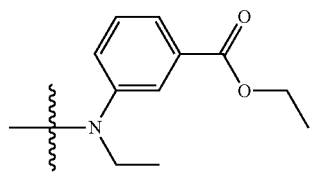 [SMILES: *N(CC)c1cccc(C(=O)OCC)c1] |
| 415 | ↑ | ↑ | ↑ | 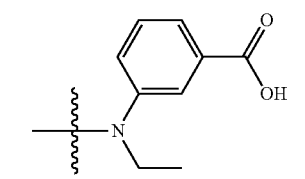 [SMILES: *N(CC)c1cccc(C(=O)O)c1] |
| 416 | ↑ | ↑ | ↑ | 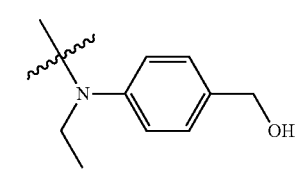 [SMILES: *N(CC)c1ccc(CO)cc1] |
| 417 | ↑ | ↑ | ↑ | 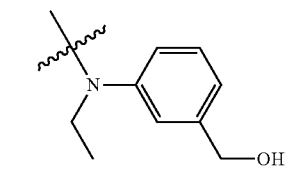 [SMILES: *N(CC)c1cccc(CO)c1] |
| 418 | ↑ | ↑ | ↑ | 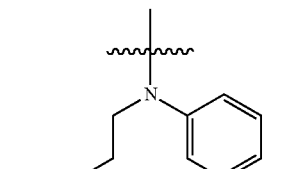 |
| 419 | ↑ | ↑ | ↑ | 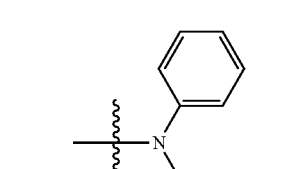 |
| 420 | 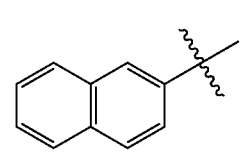 [SMILES: *c1ccc2ccccc2c1] | ↑ | ↑ | 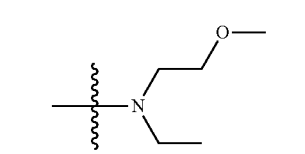 |

TABLE 4-continued
| Example | R¹ | R² | R³ | R⁴ |
|---|---|---|---|---|
| 421 | ↑ | ↑ | ↑ | 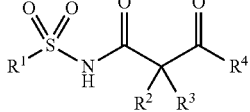 TFA |
| 422 | ↑ | ↑ | ↑ | 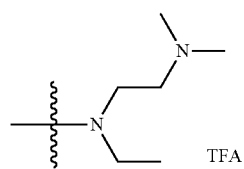 [SMILES: *N(CC)CCN(C)C] |
| 423 | ↑ | ↑ | ↑ | 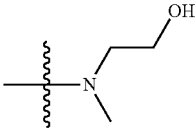 |
| 424 | ↑ | ↑ | ↑ | 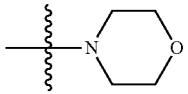 |
| 425 | 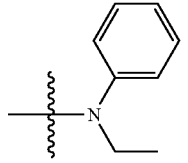 [SMILES: *N(CC)c1ccccc1] | 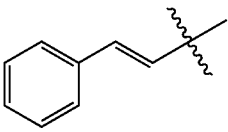 [SMILES: */C=C/c1ccccc1] | ↑ | ↑ |
| 426 | ↑ | 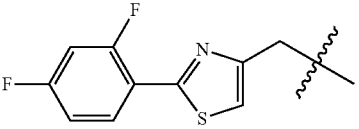 [SMILES: *Cc1csc(-c2ccc(F)cc2F)n1] | ↑ | ↑ |
| 427 | ↑ | 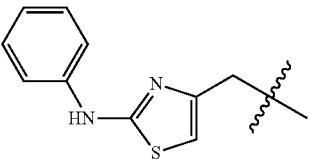 [SMILES: *Cc1csc(Nc2ccccc2)n1] | ↑ | 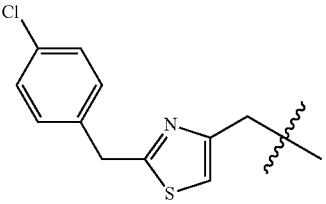 [SMILES: *Cc1csc(Cc2ccc(Cl)cc2)n1] |
| 428 | ↑ | 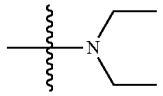 | ↑ | 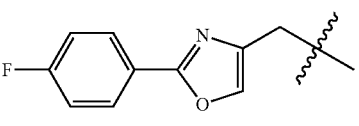 |

TABLE 4-continued
| Example | R¹ | R² | R³ | R⁴ |
|---|---|---|---|---|
| 429 | ↑ | 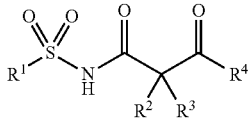 | ↑ | ↑ |
| 430 | ↑ | ↑ | ↑ | 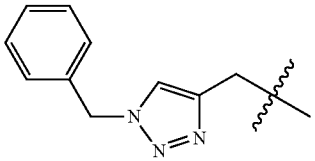 [SMILES: *Cc1cn(Cc2ccccc2)nn1] |
| 431 | ↑ | 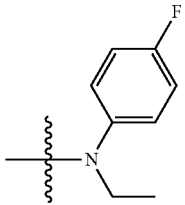 [SMILES: *N(CC)c1ccc(F)cc1] | ↑ | 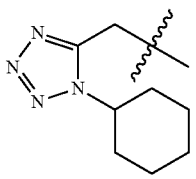 [SMILES: *Cc1nnnn1C1CCCCC1] |
| 432 | ↑ | 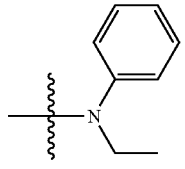 | ↑ | ↑ |
| 433 | ↑ | 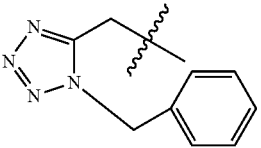 [SMILES: *Cc1nnnn1Cc1ccccc1] | ↑ | 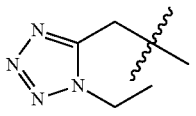 [SMILES: *Cc1nnnn1CC] |
| 434 | ↑ | 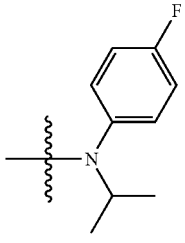 [SMILES: *N(c1ccc(F)cc1)C(C)C] | ↑ | ↑ |
| 435 | ↑ | 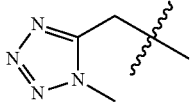 [SMILES: *Cc1nnnn1C] | ↑ | ↑ |
| 436 | 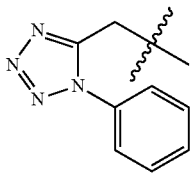 [SMILES: *Cc1nnnn1-c1ccccc1] | ↑ | ↑ | 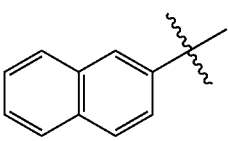 [SMILES: *c1ccc2ccccc2c1] |

TABLE 4-continued
| Example | R¹ | R² | R³ | R⁴ |
|---|---|---|---|---|
| 437 | ↑ | 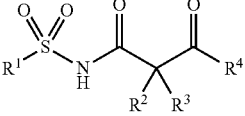 | ↑ | 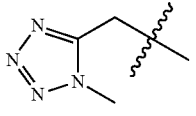 [SMILES: *Cc1nnnn1C] |
| 438 | 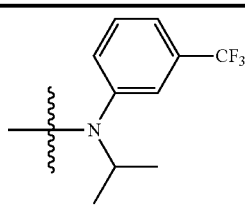 | 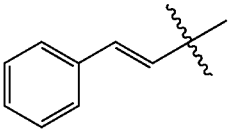 [SMILES: */C=C/c1ccccc1] | ↑ | 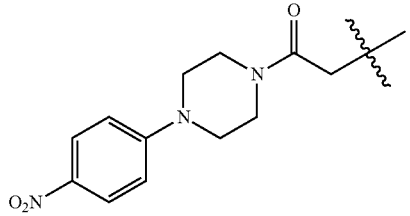 |
| 439 | ↑ | 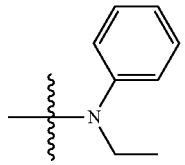 | ↑ | ↑ |
| 440 | ↑ | 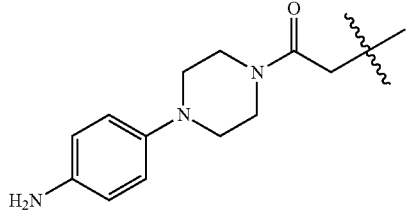 [SMILES: *CC(=O)N1CCN(c2ccc([N+](=O)[O-])cc2)CC1] | ↑ | ↑ |
| 441 | ↑ | 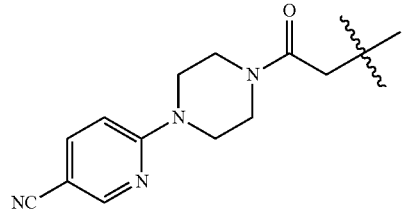 [SMILES: *CC(=O)N1CCN(c2ccc(C#N)cn2)CC1] | ↑ | ↑ |
| 442 | ↑ | 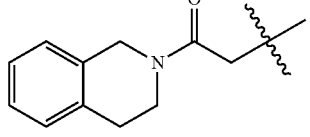 | ↑ | 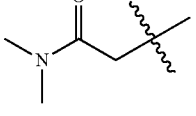 |
| 443 | ↑ | 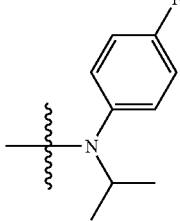 | ↑ | ↑ |

TABLE 4-continued
| Example | R¹ | R² | R³ | R⁴ |
|---|---|---|---|---|
| 444 | ↑ | 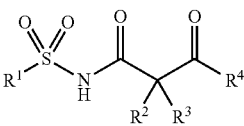 | ↑ | ↑ |
| 445 | 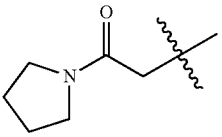 [SMILES: *CC(=O)N1CCCC1] | ↑ | ↑ | 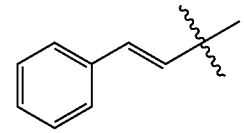 [SMILES: */C=C/c1ccccc1] |
| 446 | ↑ | ↑ | ↑ | 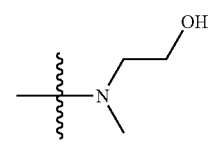 [SMILES: *N(C)CCO] |
| 447 | ↑ | ↑ | ↑ | 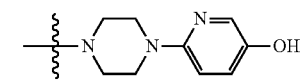 |
| 448 | ↑ | ↑ | ↑ | 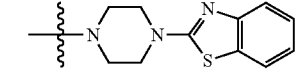 [SMILES: *N1CCN(c2nc3ccccc3s2)CC1] |
| 449 | ↑ | ↑ | ↑ | 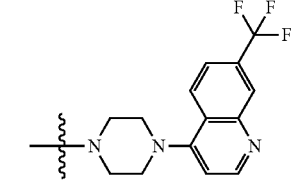 [SMILES: *N1CCN(c2ccnc3cc(C(F)(F)F)ccc23)CC1] |
| 450 | ↑ | ↑ | ↑ | 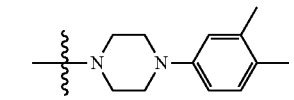 |
| 451 | ↑ | ↑ | ↑ | 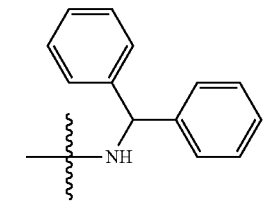 [SMILES: *NC(c1ccccc1)c1ccccc1] |
| 452 | ↑ | ↑ | ↑ | 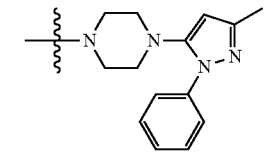 [SMILES: *N1CCN(c2cc(C)nn2-c2ccccc2)CC1] |
| 453 | ↑ | ↑ | ↑ | 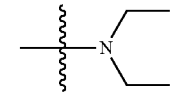 |

TABLE 4-continued
| Example | R¹ | R² | R³ | R⁴ |
|---|---|---|---|---|
| 454 | ↑ | ↑ | ↑ | 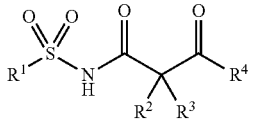 |
| 455 | 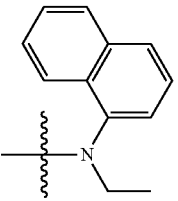 [SMILES: *N(CC)c1cccc2ccccc12] | ↑ | ↑ | ↑ |
| 456 | 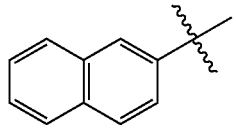 [SMILES: *c1ccc2ccccc2c1] | ↑ | ↑ | 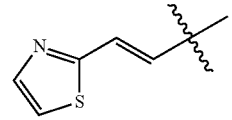 [SMILES: */C=C/c1nccs1] |
| 457 | ↑ | ↑ | ↑ | 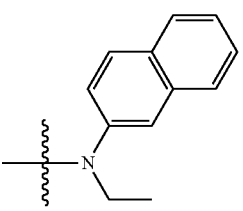 [SMILES: *N(CC)c1ccc2ccccc2c1] |
| 458 | 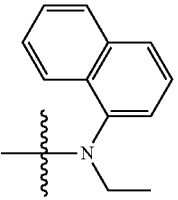 | ↑ | ↑ | 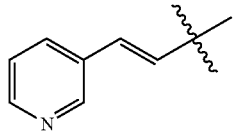 [SMILES: */C=C/c1cccnc1] |
| 459 | 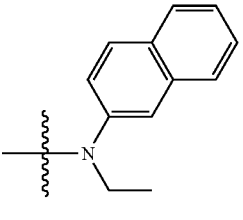 | ↑ | ↑ | 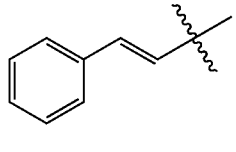 [SMILES: */C=C/c1ccccc1] |
| 460 | ↑ | ↑ | ↑ | 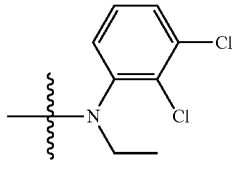 [SMILES: *N(CC)c1cccc(Cl)c1Cl] |

TABLE 4-continued
₂-NH-C(O)-C(R²)(R³)-C(O)-R⁴)
| Example | R¹ | R² | R³ | R⁴ |
|---|---|---|---|---|
| 461 | ↑ | ↑ | ↑ | 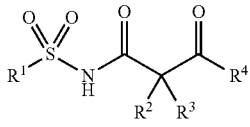 4-F-C₆H₄-N(Et)- |
| 462 | ↑ | ↑ | ↑ | 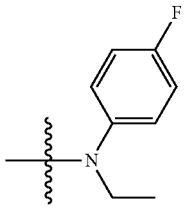 [SMILES: *N(CC)c1ccc(F)cc1] 8-(N-Me)-naphthyl |
| 463 | ↑ | ↑ | ↑ | 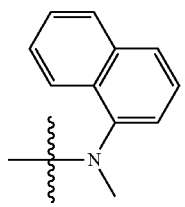 [SMILES: *N(C)c1cccc2ccccc12] 4-Cl-C₆H₄-N(Et)- |
| 464 | ↑ | ↑ | ↑ | 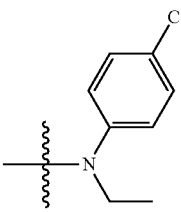 2,5-diF-C₆H₃-N(Et)- |
| 465 | ↑ | ↑ | ↑ | 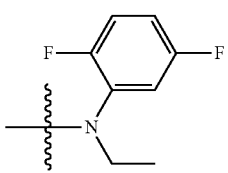 [SMILES: *N(CC)c1cc(F)ccc1F] 4-Cl-C₆H₄-N(Me)- |
| 466 | ↑ | ↑ | ↑ | 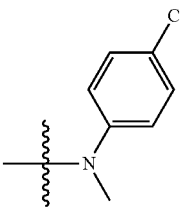 2-F-C₆H₄-N(Et)- |
| 467 | ↑ | ↑ | ↑ | 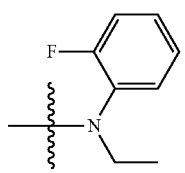 2,4,6-triF-C₆H₂-N(Et)- |

TABLE 4-continued

R¹–S(O)₂–NH–C(R²)(R³)–C(O)–R⁴

| Example | R¹ | R² | R³ | R⁴ |
|---------|----|----|----|----|
| 468 | ↑ | ↑ | ↑ | N-ethyl-N-(2,4-difluorophenyl)amino |
| 469 | ↑ | ↑ | ↑ | N-ethyl-N-(benzo[d][1,3]dioxol-5-yl)amino |
| 470 | ↑ | ↑ | ↑ | 5-bromoindolin-1-yl |
| 471 | ↑ | ↑ | ↑ | 6-fluoro-2-methyl-3,4-dihydroquinolin-1(2H)-yl |
| 472 | ↑ | ↑ | ↑ | N-benzyl-N-phenylamino |
| 473 | ↑ | ↑ | ↑ | 3,4-dihydroisoquinolin-2(1H)-yl |
| 474 | ↑ | ↑ | ↑ | N-ethyl-N-(4-(methylthio)phenyl)amino |

TABLE 4-continued
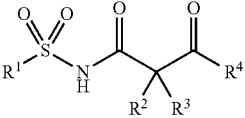
| Example | R¹ | R² | R³ | R⁴ |
|---|---|---|---|---|
| 475 | ↑ | ↑ | ↑ | 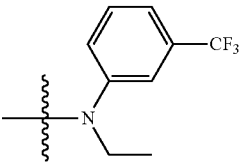 [SMILES: *N(CC)c1cccc(C(F)(F)F)c1] |
| 476 | ↑ | ↑ | ↑ | 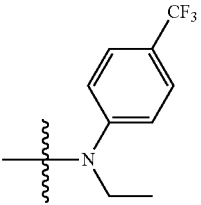 [SMILES: *N(CC)c1ccc(C(F)(F)F)cc1] |
| 477 | ↑ | ↑ | ↑ | 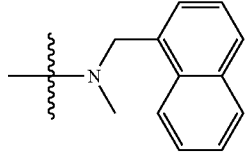 [SMILES: *N(C)Cc1cccc2ccccc12] |
| 478 | ↑ | ↑ | ↑ | 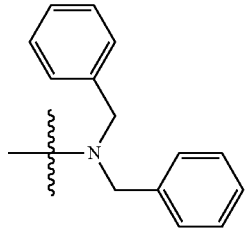 [SMILES: *N(Cc1ccccc1)Cc1ccccc1] |
| 479 | ↑ | ↑ | ↑ | 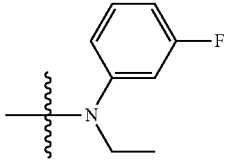 [SMILES: *N(CC)c1cccc(F)c1] |
| 480 | ↑ | ↑ | ↑ | 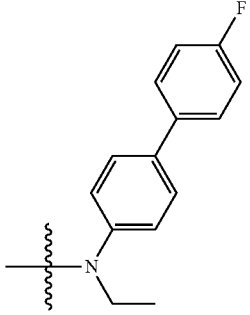 [SMILES: *N(CC)c1ccc(-c2ccc(F)cc2)cc1] |

TABLE 4-continued
| Example | R¹ | R² | R³ | R⁴ |
|---|---|---|---|---|
| 481 | ↑ | ↑ | ↑ | 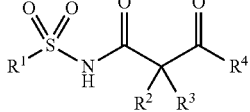 |
| 482 | ↑ | ↑ | ↑ | 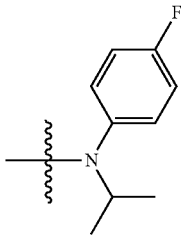 [SMILES: *N(c1ccc(F)cc1)C(C)C] |
| 483 | ↑ | ↑ | ↑ | 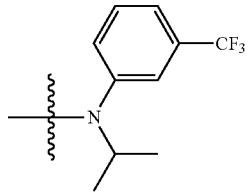 [SMILES: *N(c1cccc(C(F)(F)F)c1)C(C)C] |
| 484 | ↑ | ↑ | ↑ | 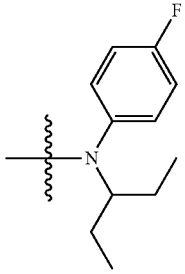 [SMILES: *N(c1ccc(F)cc1)C(CC)CC] |
| 485 | ↑ | ↑ | ↑ | 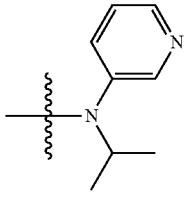 [SMILES: *N(c1cccnc1)C(C)C] |
| 486 | ↑ | 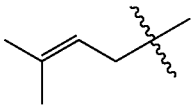 [SMILES: *CC=C(C)C] | ↑ | 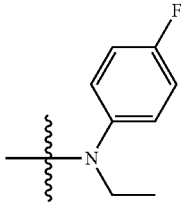 [SMILES: *N(CC)c1ccc(F)cc1] |

TABLE 4-continued
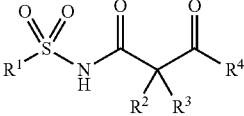
| Example | R¹ | R² | R³ | R⁴ |
|---|---|---|---|---|
| 487 | ↑ | 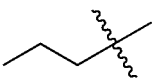 [SMILES: *CCC] | ↑ | 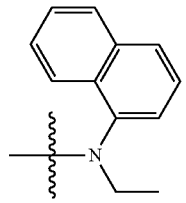 [SMILES: *N(CC)c1cccc2ccccc12] |
| 488 | ↑ | ↑ | ↑ | 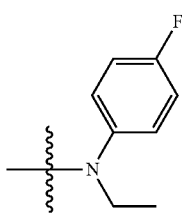 [SMILES: *N(CC)c1ccc(F)cc1] |
| 489 | ↑ | ↑ | ↑ | 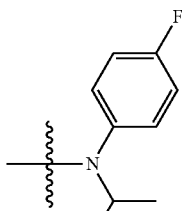 |
| 490 | ↑ | 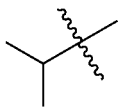 | ↑ | ↑ |
| 491 | ↑ | 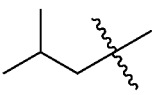 [SMILES: *CC(C)C] | ↑ | ↑ |
| 492 | 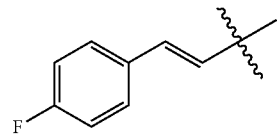 [SMILES: */C=C/c1ccc(F)cc1] | ↑ | ↑ | ↑ |
| 493 | 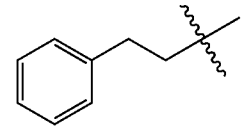 [SMILES: *CCc1ccccc1] | ↑ | ↑ | ↑ |
| 494 | 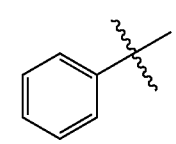 | ↑ | ↑ | ↑ |

TABLE 4-continued
| Example | R¹ | R² | R³ | R⁴ |
|---|---|---|---|---|
| 495 | 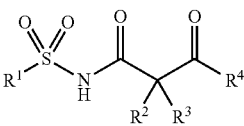 | ↑ | ↑ | ↑ |
| 496 | 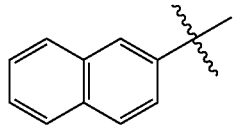 [SMILES: *c1ccc2ccccc2c1] | ↑ | ↑ | ↑ |
| 497 | 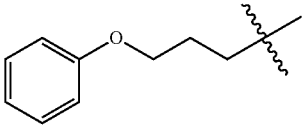 [SMILES: *CCCOc1ccccc1] | ↑ | ↑ | ↑ |
| 498 | 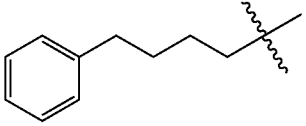 [SMILES: *CCCCc1ccccc1] | ↑ | ↑ | ↑ |
| 499 | 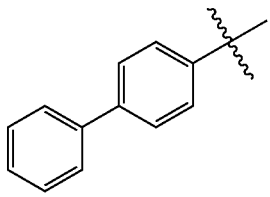 [SMILES: *c1ccc(-c2ccccc2)cc1] | ↑ | ↑ | 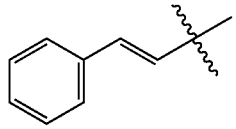 [SMILES: */C=C/c1ccccc1] |
| 500 | ↑ | ↑ | ↑ | 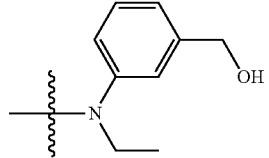 [SMILES: *N(CC)c1cccc(CO)c1] |
| 501 | ↑ | ↑ | ↑ | 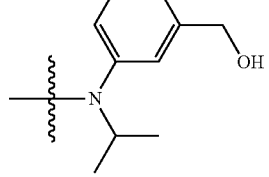 |
| 502 | ↑ | ↑ | ↑ | 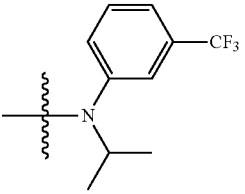 [SMILES: *N(c1cccc(C(F)(F)F)c1)C(C)C] HCl |

US 10,071,099 B2
TABLE 4-continued
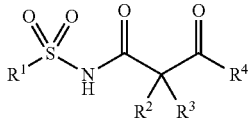
| Example | R¹ | R² | R³ | R⁴ |
|---|---|---|---|---|
| 503 | ↑ | ↑ | ↑ | 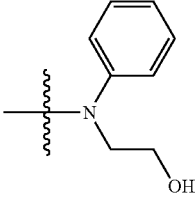 [SMILES: *N(CCO)c1ccccc1] |
| 504 | ↑ | ↑ | ↑ | 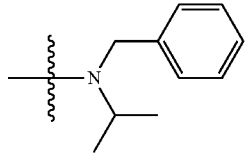 [SMILES: *N(Cc1ccccc1)C(C)C] |
| 505 | ↑ | ↑ | ↑ | 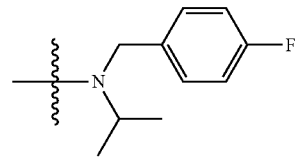 [SMILES: *N(Cc1ccc(F)cc1)C(C)C] |
| 506 | ↑ | ↑ | ↑ | 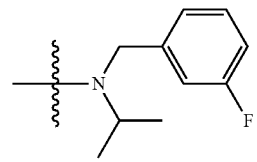 [SMILES: *N(Cc1cccc(F)c1)C(C)C] |
| 507 | ↑ | ↑ | ↑ | 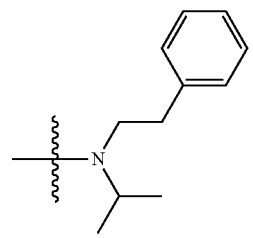 [SMILES: *N(CCc1ccccc1)C(C)C] |
| 508 | ↑ | ↑ | ↑ | 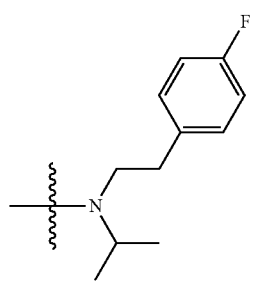 [SMILES: *N(CCc1ccc(F)cc1)C(C)C] |

TABLE 4-continued
| Example | R¹ | R² | R³ | R⁴ |
|---|---|---|---|---|
| 509 | 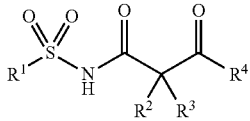 | ↑ | ↑ | 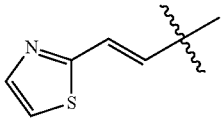 [SMILES: */C=C/c1nccs1] |
| 510 | 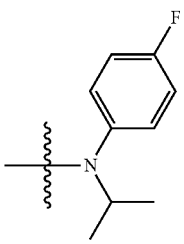 [SMILES: *N(c1ccc(F)cc1)C(C)C] | ↑ | ↑ | ↑ |
| 511 | 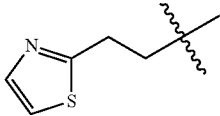 [SMILES: *CCc1nccs1] | ↑ | ↑ | ↑ |
| 512 | 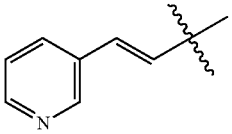 [SMILES: */C=C/c1cccnc1] | 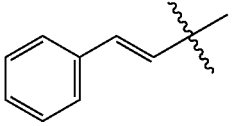 [SMILES: */C=C/c1ccccc1] | ↑ | ↑ |
| 513 | ↑ | 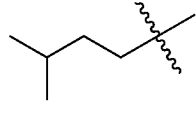 [SMILES: *CCC(C)C] | ↑ | |
| 514 | ↑ | 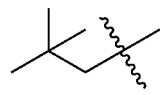 [SMILES: *CC(C)(C)C] | ↑ | 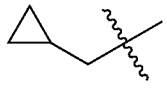 [SMILES: *CC1CC1] |
| 515 | ↑ | ↑ | ↑ | 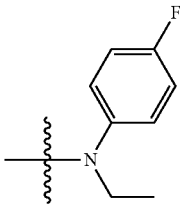 [SMILES: *N(CC)c1ccc(F)cc1] |
| 516 | ↑ | ↑ | ↑ | ↑ |

TABLE 4-continued
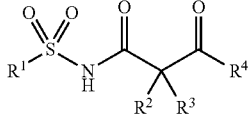
| Example | R¹ | R² | R³ | R⁴ |
|---|---|---|---|---|
| 517 | 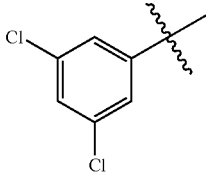 [SMILES: *c1cc(Cl)cc(Cl)c1] |  | ↑ | ↑ |
| 518 | 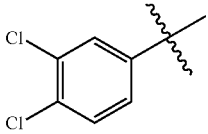 [SMILES: *c1ccc(Cl)c(Cl)c1] | ↑ | ↑ | ↑ |
| 519 | 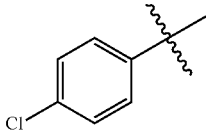 [SMILES: *c1ccc(Cl)cc1] | ↑ | ↑ | ↑ |
| 520 | 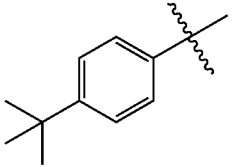 [SMILES: *c1ccc(C(C)(C)C)cc1] | ↑ | ↑ | ↑ |
| 521 | 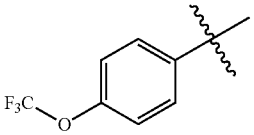 [SMILES: *c1ccc(OC(F)(F)F)cc1] | ↑ | ↑ | ↑ |
| 522 | 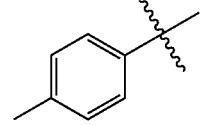 [SMILES: *c1ccc(C)cc1] | ↑ | ↑ | ↑ |
| 523 | 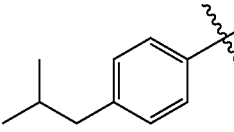 | ↑ | ↑ | ↑ |
| 524 | 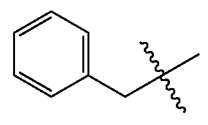 [SMILES: *Cc1ccccc1] | ↑ | ↑ | ↑ |
| 525 | 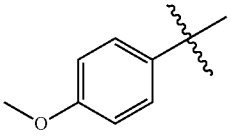 [SMILES: *c1ccc(OC)cc1] | ↑ | ↑ | ↑ |

TABLE 4-continued
| Example | R¹ | R² | R³ | R⁴ |
|---|---|---|---|---|
| 526 | 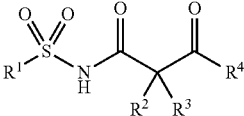 | ↑ | ↑ | ↑ |
| 527 | 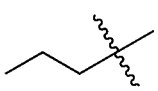 | ↑ | ↑ | ↑ |
| 528 | 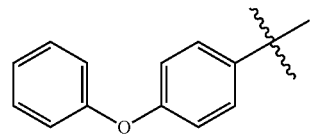 [SMILES: *c1ccc(Oc2ccccc2)cc1] | ↑ | ↑ | ↑ |
| 529 | 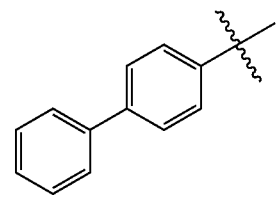 [SMILES: *c1ccc(-c2ccccc2)cc1] | ↑ | ↑ | ↑ |
| 530 | 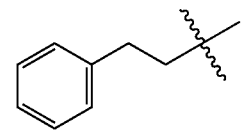 [SMILES: *CCc1ccccc1] | ↑ | ↑ | ↑ |
| 531 | 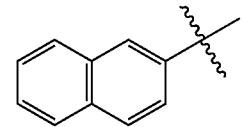 [SMILES: *c1ccc2ccccc2c1] | ↑ | ↑ | ↑ |
| 532 | 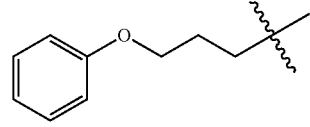 | ↑ | ↑ | 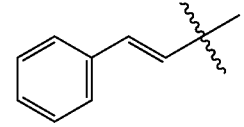 |
| 533 | ↑ | ↑ | ↑ | 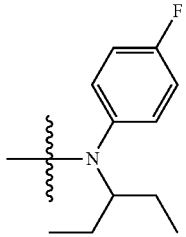 [SMILES: *N(c1ccc(F)cc1)C(CC)CC] |

TABLE 4-continued
| Example | R¹ | R² | R³ | R⁴ |
|---|---|---|---|---|
| 534 | ↑ | ↑ | ↑ | 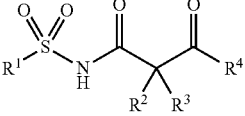 |
| 535 | 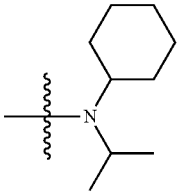 [SMILES: *N(C(C)C)C1CCCCC1] | ↑ | ↑ | 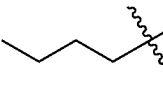 |
| 536 | 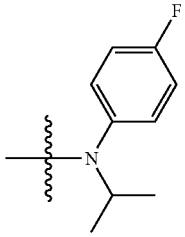 [SMILES: *N(c1ccc(F)cc1)C(C)C] | ↑ | ↑ | ↑ |
| 537 | 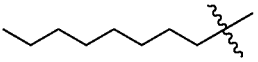 | ↑ | ↑ | ↑ |
| 538 | 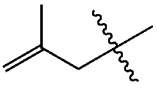 [SMILES: *CC(=C)C] | 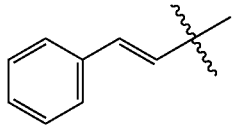 | ↑ | ↑ |
| 539 | ↑ | 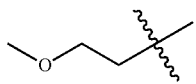 | ↑ | ↑ |
| 540 | ↑ | 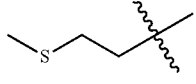 [SMILES: *CCSC] | ↑ | ↑ |
| 541 | ↑ | 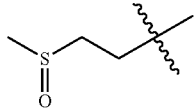 [SMILES: *CCS(C)=O] | ↑ | ↑ |
| 542 | ↑ | 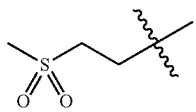 [SMILES: *CCS(C)(=O)=O] | ↑ | 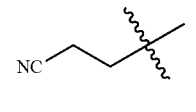 [SMILES: *CCC#N] |
| 543 | 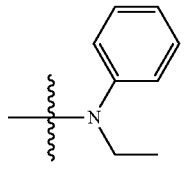 [SMILES: *N(CC)c1ccccc1] | ↑ | ↑ | ↑ |

TABLE 4-continued
| Example | R¹ | R² | R³ | R⁴ |
|---|---|---|---|---|
| 544 | 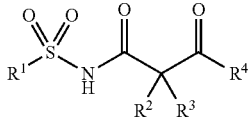 | ↑ | ↑ | 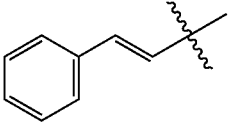 [SMILES: */C=C/c1ccccc1] |
| 545 | 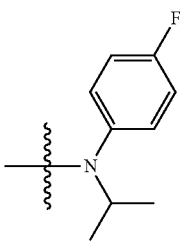 [SMILES: *N(c1ccc(F)cc1)C(C)C] | 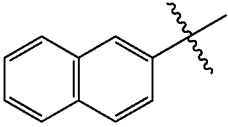 [SMILES: *c1ccc2ccccc2c1] | ↑ | 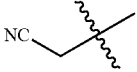 |
| 546 | 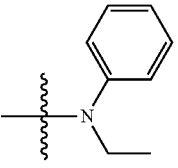 [SMILES: *N(CC)c1ccccc1] | ↑ | ↑ | ↑ |
| 547 | ↑ | 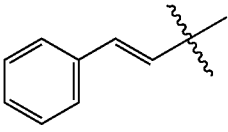 [SMILES: */C=C/c1ccccc1] | ↑ | 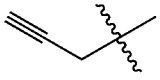 [SMILES: *CC#C] |
| 548 | ↑ | 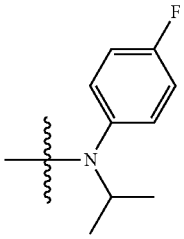 [SMILES: *N(c1ccc(F)cc1)C(C)C] | ↑ | ↑ |
| 549 | 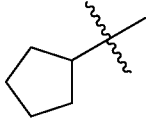 [SMILES: *C1CCCC1] | 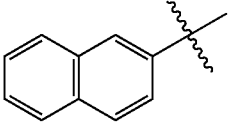 [SMILES: *c1ccc2ccccc2c1] | ↑ | 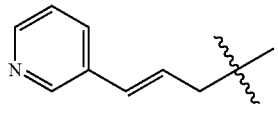 [SMILES: *C/C=C/c1cccnc1] |
| 550 | ↑ | 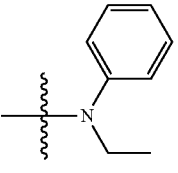 [SMILES: *N(CC)c1ccccc1] | ↑ | ↑ |
| 551 | ↑ | 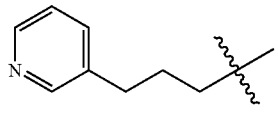 [SMILES: *CCCc1cccnc1] | ↑ | ↑ |

TABLE 4-continued
| Example | R¹ | R² | R³ | R⁴ |
|---|---|---|---|---|
| 552 | ↑ | 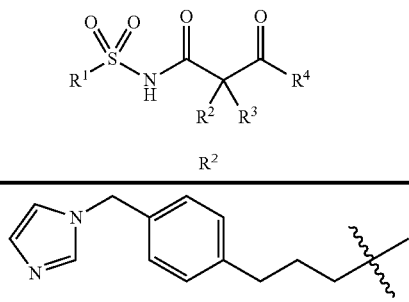 | ↑ | ↑ |
| 553 | ↑ | 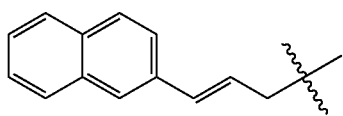 [SMILES: *C/C=C/c1ccc2ccccc2c1] | ↑ | ↑ |
| 554 | ↑ | 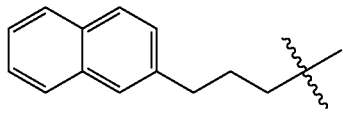 [SMILES: *CCCc1ccc2ccccc2c1] | ↑ | ↑ |
| 555 | ↑ | 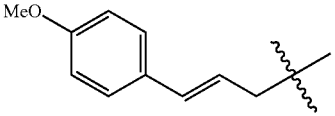 [SMILES: *C/C=C/c1ccc(OC)cc1] | ↑ | ↑ |
| 556 | ↑ | 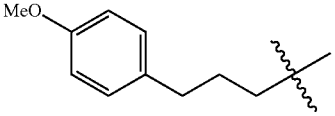 [SMILES: *CCCc1ccc(OC)cc1] | ↑ | ↑ |
| 557 | ↑ | 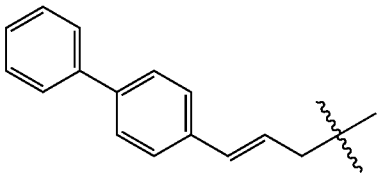 [SMILES: *C/C=C/c1ccc(-c2ccccc2)cc1] | ↑ | ↑ |
| 558 | ↑ | 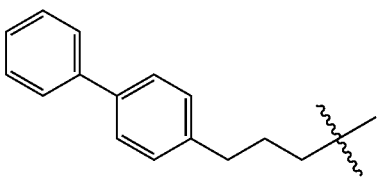 [SMILES: *CCCc1ccc(-c2ccccc2)cc1] | ↑ | ↑ |
| 559 | ↑ | 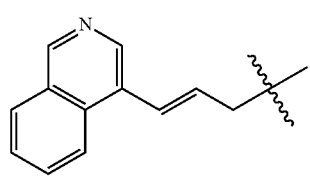 [SMILES: *C/C=C/c1cncc2ccccc12] | ↑ | ↑ |
| 560 | ↑ | 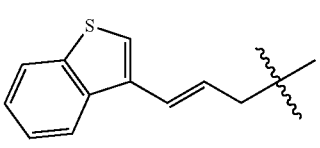 [SMILES: *C/C=C/c1csc2ccccc12] | ↑ | ↑ |
| 561 | ↑ | 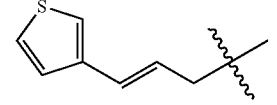 [SMILES: *C/C=C/c1ccsc1] | ↑ | ↑ |

TABLE 4-continued

[Structure: R¹-S(O)₂-NH-C(O)-C(R²)(R³)-C(O)-R⁴]

| Example | R¹ | R² | R³ | R⁴ |
|---------|----|----|----|----|
| 562 | ↑ | EtO₂C-C₆H₄-CH=CH-CH(Me)- | ↑ | ↑ |
| 563 | ↑ | EtO₂C-C₆H₄-CH₂CH₂-CH(Me)- | ↑ | ↑ |
| 564 | ↑ | F-C₆H₄-CH=CH-CH(Me)- | ↑ | ↑ |
| 565 | ↑ | F-C₆H₄-CH₂CH₂-CH(Me)- | ↑ | ↑ |
| 566 | ↑ | O₂N-C₆H₄-N(piperazine)N-CH₂CH₂- | ↑ | ↑ |
| 567 | ↑ | H₂N-C₆H₄-N(piperazine)N-CH₂CH₂- | ↑ | ↑ |
| 568 | Ph-CH=CH-CH(Me)- | F, F | | N-ethyl-N-(1-naphthyl)amino- |
| 569 | ↑ | Me, Me | | N-isopropyl-N-(4-fluorophenyl)amino- |
| 570 | ↑ | cyclobutylidene | | N-benzyl-N-phenylamino- |
| 571 | ↑ | ↑ | | -CH(Et)(Et) |

TABLE 4-continued
| Example | R¹ | R² | R³ | R⁴ |
|---|---|---|---|---|
| 572 | ↑ | ↑ | | 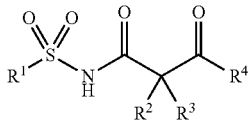 |
| 573 | ↑ | 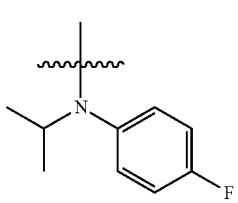 [SMILES: *N(c1ccc(F)cc1)C(C)C] | | ↑ |
| 574 | 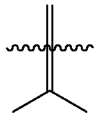 [SMILES: *=C(C)C] | 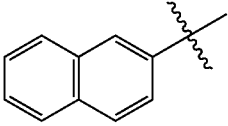 [SMILES: *c1ccc2ccccc2c1] | | 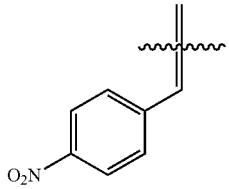 [SMILES: *=Cc1ccc([N+](=O)[O-])cc1] |
| 575 | ↑ | 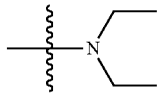 [SMILES: *N(CC)CC] | | ↑ |
| 576 | ↑ | 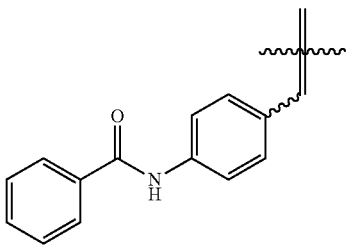 [SMILES: *=Cc1ccc(NC(=O)c2ccccc2)cc1] | H | ↑ |
| 577 | ↑ | 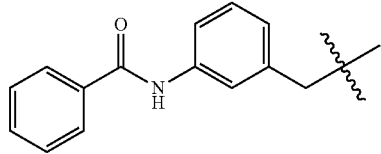 [SMILES: *Cc1cccc(NC(=O)c2ccccc2)c1] | ↑ | ↑ |
| 578 | ↑ | 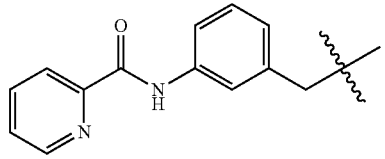 [SMILES: *Cc1cccc(NC(=O)c2ccccn2)c1] | ↑ | ↑ |

TABLE 4-continued
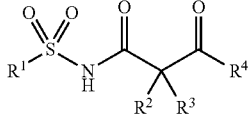
| Example | R¹ | R² | R³ | R⁴ |
|---|---|---|---|---|
| 579 | ↑ |  | ↑ | ↑ |
| 580 | ↑ |  | ↑ | ↑ |
| 581 | ↑ |  | ↑ | ↑ |
| 582 | ↑ |  | ↑ | ↑ |
| 583 | ↑ | 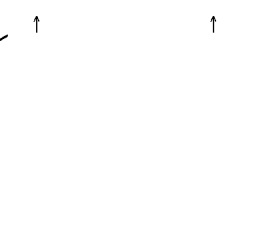 | ↑ | ↑ |
| 584 | ↑ |  | ↑ | ↑ |
| 585 | ↑ |  | ↑ | ↑ |

TABLE 4-continued

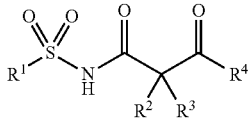

| Example | R¹ | R² | R³ | R⁴ |
|---|---|---|---|---|
| 586 | ↑ | 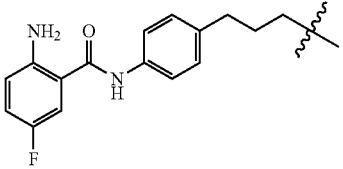 [SMILES: *CCCc1ccc(NC(=O)c2cc(F)ccc2N)cc1] | ↑ | ↑ |
| 587 | ↑ | 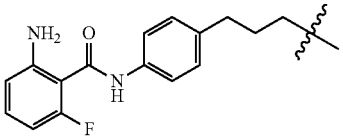 [SMILES: *CCCc1ccc(NC(=O)c2c(N)cccc2F)cc1] | ↑ | ↑ |
| 588 | 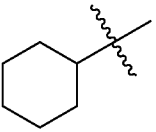 [SMILES: *C1CCCCC1] | 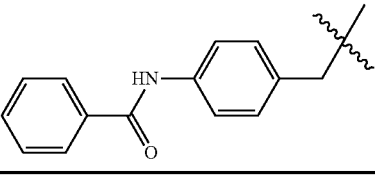 | ↑ | ↑ |

↑: same substituent as above

Particularly preferred non-peptidic angiotensin type 2 receptor agonists in the present invention are the following compounds and pharmacologically acceptable salts thereof.

N,N-diethyl-2-{4-[(2,6-difluorobenzoyl)amino]benzyl}-N'-(2-naphthylsulfonyl)malonamide, (2S)-2-[4-(benzoylamino)benzyl]-N,N-diethyl-N'-(2-naphthylsulfonyl) malonamide, (2S)—N,N-diethyl-2-{4-[(2-fluorobenzoyl)amino]benzyl}-N'-(2-naphthylsulfonyl)malonamide, (2S)—N,N-diethyl-2-{4-[(3-fluorobenzoyl)amino]benzyl}-N'-(2-naphthylsulfonyl)malonamide, (2S)—N,N-diethyl-2-{4-[(2,4-difluorobenzoyl)amino]benzyl}-N-(2-naphthylsulfonyl)malonamide, (2S)—N,N-diethyl-2-{4-[(4-methylbenzoyl)amino]benzyl}-N'-(2-naphthylsulfonyl) malonamide, (2S)—N,N-diethyl-N'-(2-naphthylsulfonyl)-2-{4-[(2-thienoyl)amino]benzyl}malonamide, (2S)—N,N-diethyl-2-{4-[(2-furoyl)amino]benzyl}-N'-(2-naphthylsulfonyl) malonamide, (2S)-2-{4-[(2-amino-5-fluorobenzoyl)amino]benzyl}-N,N-diethyl-N'-(2-naphthylsulfonyl)malonamide, (2S)-2-{4-[(2-amino-6-fluorobenzoyl)amino]benzyl}-N,N-diethyl-N'-(2-naphthylsulfonyl)malonamide, (2S)—N,N-diethyl-N'-(2-naphthylsulfonyl)-2-{4-[(2-pyridylcarbonyl)amino]benzyl}malonamide, (2S)-2-{4-[(2-amino-4-chlorobenzoyl)amino]benzyl}-N,N-diethyl-N'-(2-naphthylsulfonyl)malonamide, (2S)-2-{4-[(2-aminobenzoyl)amino]benzyl}-N,N-diethyl-N'-(2-naphthylsulfonyl) malonamide, (2S)-2-{4-[(2-amino-5-chlorobenzoyl)amino]benzyl}-N,N-diethyl-N'-(2-naphthylsulfonyl)malonamide, (2S)-2-{4-[(2-amino-4,5-difluorobenzoyl)amino]benzyl}-N,N-diethyl-N'-(2-naphthylsulfonyl)malonamide, (2S)-2-{4-[(2-amino-4-fluorobenzoyl)amino]benzyl}-N,N-diethyl-N'-(2-naphthylsulfonyl)malonamide, (2S)-2-{4-[(2-amino-5-methylbenzoyl)amino]benzyl}-N,N-diethyl-N'-(2-naphthylsulfonyl)malonamide, 2-(4-fluorobenzyl)-N-isopropyl-N-(3-pyridyl)-N'-((E)-styrylsulfonyl)malonamide, 2-allyl-N-(4-fluorophenyl)-N-isopropyl-N'-((E)-styrylsulfonyl)malonamide, N-(4-fluorophenyl)-2-isobutyl-N-isopropyl-N'-((E)-styrylsulfonyl)malonamide, N-(4-fluorophenyl)-2-isobutyl-N-isopropyl-N'-phenethylsulfonylmalonamide, N-(4-fluorophenyl)-2-isobutyl-N-isopropyl-N'-(2-naphthylsulfonyl)malonamide, (2S or 2R)-2-cyclopropylmethyl-N-(4-fluorophenyl)-N-isopropyl-N'-((E)-2-styrylsulfonyl)malonamide, 2-cyclopropylmethyl-N-(4-fluorophenyl)-N-isopropyl-N'-phenethylsulfonylmalonamide, and 2-cyclopropylmethyl-N-(4-fluorophenyl)-N-isopropyl-N'-(2-naphthylsulfonyl)malonamide.

Among them, as the non-peptidic angiotensin type 2 receptor agonist in the present invention, the following compounds and pharmacologically acceptable salts thereof are preferred.

(2S)-2-[4-(benzoylamino)benzyl]-N,N-diethyl-N'-(2-naphthylsulfonyl)malonamide, (2S)-2-{4-[(2-amino-6-fluorobenzoyl)amino]benzyl}-N,N-diethyl-N'-(2-naphthylsulfonyl)malonamide, (2S)-2-{4-[(2-amino-4-chlorobenzoyl)amino]benzyl}-N,N-diethyl-N'-(2-naphthylsulfonyl)malonamide, 2-allyl-N-(4-fluorophenyl)-N-isopropyl-N'-((E)-styrylsulfonyl)malonamide, and N-(4-fluorophenyl)-2-isobutyl-N-isopropyl-N'-((E)-styrylsulfonyl)malonamide.

The AT2 receptor agonist may be in the form of a pharmacologically acceptable salt thereof. Examples of the pharmacologically acceptable salt include inorganic acid addition salts (for example, salts with hydrochloric acid, hydrobromic acid, hydroiodic acid, sulfuric acid, phosphoric acid, etc.), organic acid addition salts (for example, salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid, etc.), inorganic base addition salts (for example, salts with sodium, potassium, calcium, magnesium, etc.), salts with amino acid (for example, salts with glutamic acid, aspartic acid, arginine, lysine etc.), etc.

The AT2 receptor agonist may show polymorphism, and in cases where the molecule comprises one or more chiral carbons, optical isomers and stereoisomers can exist. The AT2 receptor agonist may be in the form of a hydrate or a solvate. In addition, depending on the existence of an unsaturated bond, the type of substituent(s), pH, etc., the AT2 receptor agonist can exist as one or more tautomers. Therefore, the AT2 receptor agonist includes any of the above-mentioned stereoisomers, optical isomers, polymorphs, tautomers, and any mixtures thereof.

One kind of the AT2 receptor agonist or a combination of two or more kinds thereof may be used.

The AT2 receptor agonist can be synthesized by a known method (for example, the method described in WO 2008/156142).

The medicament of the present invention is not particularly limited as long as it comprises the above-mentioned AT2 receptor agonist (or the vasoprotective agent) as an active ingredient. The medicament may further comprise a publicly known pharmacologically acceptable inert carrier, excipient, diluent, etc. In the treatment or prevention method for suppressing or preventing the metastasis of a malignant tumor, it is preferred that the above medicament is administered to a patient.

Utilizing the medicament (or the AT2 receptor agonist), the vasoprotective agent, the method for suppressing or preventing the metastasis of a malignant tumor, and the treatment or prevention method of the present invention, the metastasis of a malignant tumor can be appropriately suppressed or prevented. Further, the present invention exerts an excellent metastasis suppressing effect even on a malignant tumor of which the metastasis has been exacerbated or augmented by an anticancer and/or antitumor agent (for example, a platinum-based antitumor agent, such as cisplatin). Similarly, the present invention exerts an excellent effect even on the metastasis of a malignant tumor of a patient who has undergone resection of a tumor, radiotherapy, or laser ablation treatment. Therefore, according to the present invention, it is also possible to suppress or prevent the metastasis of a malignant tumor.

Usually, the metastasis suppressing effect according to the present invention is exerted in a manner other than cell-killing or cytostatic action on a malignant tumor itself. The effect is different from that of common anticancer/antitumor agents which acts on the malignant tumor itself, and is an effect brought by a protecting action on the blood vessels or other vessels of the host (for example, a malignant tumor patient).

Since the effect of the present invention is exerted on the host, the present invention exerts an excellent metastasis suppressing effect on any and all kinds of malignant tumors (for example, carcinomas) regardless of their kind.

The AT2 receptor agonist (or the medicament or the vasoprotective agent, hereinafter the same holds true in similar descriptions) of the present invention for suppressing or preventing the metastasis of a malignant tumor is suitable also as a AT2 receptor agonist for suppressing or preventing malignant tumor cells from colonizing or invading vascular endothelium.

The method for suppressing or preventing the metastasis of a malignant tumor, and the treatment or prevention method of the present invention are suitable also as a method for suppressing or preventing malignant tumor cells from colonizing or invading vascular endothelium.

The medicament (or the AT2 receptor agonist), the method for suppressing or preventing the metastasis of a malignant tumor, and the treatment or prevention method of the present invention is suitable for suppressing or preventing the metastasis of any and all kinds of malignant tumors. In particular, they are suitable for suppressing or preventing colonization (adhesion) and invasion of malignant tumor cells to vascular endothelium during the process of blood-borne metastasis.

Because of these excellent effects, the present invention is useful not only for suppression and prevention of the metastasis of a malignant tumor and for prevention etc. of the metastasis after therapeutic resection of a tumor but also for effective suppression or prevention of the metastasis of a malignant tumor that is hard to resect.

An objective of the present invention is to suppress or prevent the metastasis of a malignant tumor, and the intended patients are usually those with a malignant tumor. The kind of the malignant tumor is not particularly limited, and examples thereof include various types, for example, epithelial malignant tumor, such as carcinoma; non-epithelial malignant tumor, such as sarcoma; and melanoma.

Examples of the malignant tumor include lung cancer (non-small cell lung cancer, small cell lung cancer, malignant mesothelioma, etc.), gastric cancer, colon cancer, liver cancer, kidney cancer, bladder cancer, pancreatic cancer, thyroid cancer, breast cancer, uterine cancer, ovarian cancer, prostatic cancer, bone tumor, brain tumor, etc.

An objective of the present invention is to suppress or prevent the metastasis of a malignant tumor, and the site of metastasis can be any and all organs and tissues throughout the body because metastasis occurs in such a manner that malignant tumor cells released from a primary tumor (primary lesion) enter the blood circulatory system or the lymph system and are diffused to other parts of the body. Malignant tumor cells tend to metastasize to, in particular, organs and tissues where thin blood vessels such as capillaries are dense and the blood flow is high. In the case of a solid tumor, examples of the most common metastasis site include the lung, the bone, the liver, and the brain. In particular, the lung and the liver are significant as sites of metastasis. According to the present invention, the metastasis to, for example, tissues or organs, such as the lung, the bone, the liver, and the brain, more preferably to the lung or the liver is suppressed or prevented effectively.

The malignant tumor may be a primary tumor or a metastatic tumor, and the medicament (or the AT2 receptor agonist or the vasoprotective agent, hereinafter the same holds true in similar descriptions) of the present invention may be administered at any time after the detection of a malignant tumor, such as carcinoma, in a patient. In view of the general practice for metastasis suppression, continuous administration or regular administration at certain intervals is preferred.

The medicament of the present invention is preferably administered to a patient who is to undergo or who has undergone resection of a malignant tumor. A patient who is receiving or who has received administration of an anticancer agent and/or an antitumor agent is also preferable as a subject of administration of the medicament of the present invention. The anticancer agent and/or the antitumor agent is, for example, one or more kinds of anticancer and/or antitumor agents that are other than the medicament of the present invention and can be used together with the medicament of the present invention. Such other anticancer and/or antitumor agents will be described later.

In cases where resection of a malignant tumor, such as carcinoma, is conducted, efficient suppression of the metastasis of the malignant tumor can be achieved as follows. The medicament is administered to the patient for protection of blood vessels before the resection, and then the resection is performed. The blood vessel protection is continued until the influence of inflammatory cytokines produced after the resection disappears. Usually, the administration is started about 1 week or more, preferably about 10 days or more before the resection, and continued until about 1 week or more, preferably about 10 days or more after the resection.

The dosage form and the administration route of the medicament of the present invention are not particularly limited, and one or more kinds of oral or parenteral dosage forms can be selected depending on the conditions of the patient. One or more of oral dosage forms and one or more of parenteral dosage forms can be used in combination. Since the medicament of the present invention can be used, in particular, as an oral medicament (oral agent), it can be easily administered.

The medicament of the present invention can be used in combination with at least one of other metastasis-suppressing agents. As such a metastasis-suppressing agent, for example, a GC-A agonist, a GC-B agonist, a NEP inhibitor, a PDE5 inhibitor, a NO donor, an eNOS activator, a GC-C agonist, a cGMP analog, etc. as described in WO 2012/118042 can preferably be used.

In cases where one or more of said other metastasis-suppressing agents are parenterally, for example intravenously administered, continuous administration with the use of an infusion pump, a catheter, etc. is preferably performed. The duration of the continuous administration is several hours to several days (for example, about 3 to 14 days, preferably about 3 to 7 days).

As such a metastasis-suppressing agent, for example, at least one kind of vasoprotective agent selected from (i) an angiotensin II receptor antagonist, (ii) a HMG-CoA reductase inhibitor, (iii) ghrelin or its derivatives, and (iv) adrenomedullin or its derivatives; or a pharmacologically acceptable salt thereof as described in, for example, PCT/JP 2013/077140 are also preferred.

(i) Angiotensin II Receptor Antagonist:

An angiotensin II receptor antagonist has an effect of hindering angiotensin II from binding to an angiotensin II receptor (AT1 receptor). The angiotensin II receptor antagonist used as an active ingredient of said another metastasis-suppressing agent may be any agent as long as it has the effect.

Examples of the angiotensin II receptor antagonist used as an active ingredient of said another metastasis-suppressing agent include losartan, eprosartan, candesartan, candesartan cilexetil, valsartan, telmisartan, irbesartan, tasosartan, olmesartan, olmesartanmedoxomil, and azilsartan. Among them, preferred as the angiotensin II receptor antagonist are, for example, one or more kinds of eprosartan, valsartan, telmisartan, irbesartan, tasosartan, olmesartan, olmesartan medoxomil, and azilsartan; and more preferred are one or more kinds of valsartan, telmisartan, irbesartan, azilsartan, and olmesartan medoxomil. In cases where the angiotensin II receptor antagonist is administered (in combination) with an anticancer agent and/or an antitumor agent, as described later, preferred are one or more kinds of losartan, candesartan cilexetil, valsartan, telmisartan, irbesartan, azilsartan, and olmesartan medoxomil. The angiotensin II receptor antagonist as said another metastasis-suppressing agent is particularly preferably telmisartan.

(ii) HMG-CoA Reductase Inhibitor:

A HMG-CoA reductase inhibitor has an effect of specifically inhibiting HMG-CoA reductase. The HMG-CoA reductase inhibitor used as an active ingredient of said another metastasis-suppressing agent may be any agent as long as it has the effect.

Examples of the HMG-CoA reductase inhibitor used as an active ingredient of said another metastasis-suppressing agent include natural substances derived from microorganisms, semisynthetic substances derived from such natural substances, and completely synthetic compounds, and specific examples thereof include pravastatin, lovastatin, simvastatin, fluvastatin, rivastatin, atorvastatin, pitavastatin, and rosuvastatin. Among them, preferred are pravastatin, simvastatin, fluvastatin, rivastatin, atorvastatin, pitavastatin, and rosuvastatin, and particularly preferred is pitavastatin.

As the above angiotensin II receptor antagonist and the above HMG-CoA reductase inhibitor, commercially available agents or compounds may be used, for example.

(iii) Ghrelin and its Derivatives:

Ghrelin acts on the growth hormone secretagogue receptor 1a (GHS-R1a) and thereby promotes secretion of a growth hormone (GH) from the pituitary.

Also, ghrelin has an amino acid sequence usually composed of 28 amino acid residues (or 27 amino acid residues) and having a structure in which the 3rd amino acid residue from the amino terminus is acylated with a fatty acid.

In more detail, regarding human or nonhuman mammalian (rat, mouse, porcine, bovine, equine, ovine, canine, etc., for example) ghrelin, the following amino acid sequences and acylated structures are known (WO 01/07475).

```
Human:
                                      (SEQ ID NO: 1)
GSS(n-octanoyl)FLSPEHQRVQQRKESKKPPAKLQPR (SEQ ID NO: 2)
GSS(n-octanoyl)FLSPEHQRVQRKESKKPPAKLQPR Rat:
                                      (SEQ ID NO: 3)
GSS(n-octanoyl)FLSPEHQKAQQRKESKKPPAKLQPR (SEQ ID NO: 4)
GSS(n-octanoyl)FLSPEHQKAQRKESKKPPAKLQPR Mouse:
                                      (SEQ ID NO: 5)
GSS(n-octanoyl)FLSPEHQKAQQRKESKKPPAKLQPR Porcine:
                                      (SEQ ID NO: 6)
GSS(n-octanoyl)FLSPEHQKVQQRKESKKPAAKLKPR Bovine:
                                      (SEQ ID NO: 7)
GSS(n-octanoyl)FLSPEHQKLQRKEAKKPSGRLKPR Ovine:
                                      (SEQ ID NO: 8)
GSS(n-octanoyl)FLSPEHQKLQRKEPKKPSGRLKPR
```

```
Canine:
                                       (SEQ ID NO: 9)
GSS(n-octanoyl)FLSPEHQKLQQRKESKKPPAKLQPR Equine:
                                       (SEQ ID NO: 10)
GSS(n-butanoyl)FLSPEHHKVQHRKESKKPPAKLKPR
```

(In the above sequences, each amino acid residue is represented by the single character expression).

As shown above, ghrelin has a structure in which the side chain hydroxyl group of the amino acid residue (serine (S) residue etc.) at the 3rd position from the amino terminus is acylated with a fatty acid, such as octanoic acid and decanoic acid.

For example, human ghrelin is a peptide having an amino acid sequence represented by SEQ ID NO: 1 or 2, in which the amino acid residue (serine residue) at the 3rd position from the amino terminus is a modified amino acid residue having a side chain (hydroxyl group) acylated with a fatty acid (n-octanoic acid).

As the ghrelin used herein, preferred is mammalian ghrelin. For example, human or nonhuman mammalian (rat, mouse, porcine, bovine, equine, ovine, canine, etc.) ghrelin can be used. It is preferred for each individual to use ghrelin of the same species. For example, it is preferred for a human to use human ghrelin.

Examples of a ghrelin derivative include those having a structure similar to that of ghrelin and having effects similar to those of ghrelin, i.e., an agonistic effect on the growth hormone secretagogue receptor 1a (GHS-R1a) to promote secretion of a growth hormone (GH) from the pituitary.

Specific examples of the ghrelin and a derivative thereof include a peptide having a structure selected from the following (1) to (3) and having an agonistic effect on the growth hormone secretagogue receptor 1a.

(1) A peptide having an amino acid sequence represented by any one of SEQ ID NOs: 1 to 10 in which the amino acid residue at the 3rd position from the amino terminus is a modified amino acid residue having a side chain acylated with a fatty acid;

(2) A peptide having an amino acid sequence represented by any one of SEQ ID NOs: 1 to 10 in which one to several amino acids are deleted, substituted, and/or added and the amino acid residue at the 3rd position from the amino terminus is a modified amino acid residue having a side chain acylated with a fatty acid; and (3) A peptide having an amino acid sequence represented by any one of SEQ ID NOs: 1 to 10 in which the sequence from the amino terminus to at least the 4th position is conserved, one to several amino acids are deleted, substituted, and/or added in a position other than the conserved sequence, and the amino acid residue at the 3rd position from the amino terminus is a modified amino acid residue having a side chain acylated with a fatty acid.

The "amino acid sequence represented by any one of SEQ ID NOs: 1 to 10" in the above (1) to (3) is, for example in cases where the medicament of the present invention is applied to a human, preferably "an amino acid sequence represented by SEQ ID NO: 1 or 2".

Examples of the fatty acid introduced into the side chain in the above (1) to (3) include fatty acids having 2, 4, 6, 8, 10, 12, 14, 16, or 18 carbon atoms, preferably octanoic acid, decanoic acid, or a monoenoic or polyenoic acid thereof, and more preferably octanoic acid (having 8 carbon atoms, n-octanoic acid, etc.).

In the above (2) and (3), the number of amino acids intended by the "one to several amino acids are deleted, substituted, and/or added" (hereinafter the "deleted, substituted, and/or added" is sometimes referred to as "substituted or the like") is not particularly limited as long as the peptide consisting of the amino acid sequence or a derivative thereof has the desired effect (i.e., an agonistic effect on the growth hormone secretagogue receptor 1a). The number is, for example, about 1 to 9, preferably about 1 to 4, more preferably about 1 to 3, still more preferably about 1 or 2, and particularly preferably about 1. As used herein, the addition includes insertion. In cases of substitution or the like with amino acids having similar properties (charge and/or polarity), the desired functions are generally retained even if not a few amino acids have been substituted or the like. In cases where substitution or the like occurs at two or more positions, the substitution or the like in all the positions may be deletion only, substitution only, or addition only, or a combination of two or more of deletion, substitution, and addition.

In the amino acid sequence of the ghrelin derivatives used herein (for example, the above (2) and (3)), it is preferred that the sequence corresponding to from the amino terminus to at least the 4th position, preferably to the 5th position, more preferably to the 10th position of the amino acid sequence of natural ghrelin (for example, an amino acid sequence represented by any one of SEQ ID NOs: 1 to 10) is conserved.

Preferably, the amino acid sequence of the ghrelin derivatives used herein (for example, the above (2) and (3)) usually has a sequence identity of about 70% or more, preferably about 80% or more, more preferably about 90% or more, particularly preferably about 95% or more, and most preferably about 97% or more with the amino acid sequence of natural ghrelin.

Examples of other ghrelin derivatives include those in which the carboxyl terminus of the above-exemplified structure is not ended as a carboxylic acid but amidated so as to mimic a peptide bond. Such a modification makes it possible to find out the minimum unit of activity in a shorter amino acid sequence. Another example of other ghrelin derivatives may be the one in which a basic amino acid is added to or an amino acid in the form of an amide, such as -Lys-NH$_2$, is introduced to the carboxyl terminus as desired.

Other ghrelin derivatives can be designed appropriately referring to, for example, literature by Matsumoto et al. (Structural similarity of ghrelin derivatives to peptidyl growth hormone secretagogues. Matsumoto, M, Kitajima Y, Iwanami T, Hayashi Y, Tanaka S, Minamitake Y, Hosoda H, Kojima M, Matsuo H, Kangawa K. Biochem Biophys Res Commun. 2001 Jun. 15; 284(3): 655-9).

Whether the ghrelin used herein or a derivative thereof has an agonistic effect on the growth hormone secretagogue receptor 1a can be determined by the method described in literature by Matsumoto et al. (Structure-activity relationship of ghrelin: pharmacological study of ghrelin peptides. Matsumoto M, Hosoda H, Kitajima Y, Morozumi N, Minamitake Y, Tanaka, S, Matsuo H, Kojima M, Hayashi Y, Kangawa K. Biochem Biophys Res Commun. 2001 Sep. 14; 287(1): 142-6.) using, as an indicator, physiological effect via the growth hormone secretagogue receptor 1a, such as increase in an intracellular calcium ion concentration.

In more detail, for example, the ghrelin or a derivative thereof is brought into contact with growth hormone secretagogue receptor 1a, and whether the ghrelin or a derivative thereof increases an intracellular calcium ion concentration by binding to the receptor is examined. When the increase in the intracellular calcium ion concentration is observed, the compound is regarded as having the agonistic effect.

Examples of other forms of the ghrelin derivative used herein include a nucleic acid which encodes ghrelin or a ghrelin derivative having the peptide structure as described above. The nucleic acid should be designed to express, when administered in vivo, the ghrelin or its derivatives having the peptide structure as described above.

Ghrelin and a derivative thereof can be synthesized by a conventional method, for example, a chemical synthesis. For example, amino acids with protecting groups are condensed by a liquid phase method and/or a solid phase method for peptide chain elongation, and then the protecting groups are all removed with use of an acid. The resulting crude product is purified by, for example, separation and refinement methods, such as gel filtration, ultrafiltration, dialysis, sodium dodecyl sulfate polyacrylamide gel electrophoresis (SDS-PAGE), and various chromatographic technologies. It is also possible to selectively acylate the side chain of the amino acid in a targeted position with use of an acylating enzyme or an acryltransferase.

Also, a production method as a combination of a conventional recombinant DNA technology and a chemical synthesis may be employed. In this case, for example, a fragment having a modified amino acid residue is produced by chemical synthesis, another fragment not having a modified amino acid residue is separately produced by recombinant DNA technology, and then the fragments are fused together to give ghrelin or a derivative thereof (see aforementioned Patent Literature 1).

Ghrelin and a derivative thereof can be isolated from a natural material.

As used herein, "amino acid" include any and all amino acids, such as L-amino acids, D-amino acids, α-amino acids, β-amino acids, γ-amino acids, natural amino acids, and synthetic amino acids. Preferred are natural amino acids.

Adrenomedullin and its Derivatives:

Adrenomedullin is a polypeptide having a vasodilatory effect and an antihypertensive effect (blood pressure lowering effect). In the living body, from a precursor of adrenomedullin, a bioactive form of adrenomedullin (activated adrenomedullin) and PAMP (proadrenomedullin N-terminal 20 peptide) are biosynthesized (hereinafter, PAMP will be included in adrenomedullin derivatives). Adrenomedullin exerts an effect of increasing intracellular cAMP in platelets, vascular endothelial cells, and smooth muscle cells, a platelet aggregation suppressing effect, and a strong vasodilatory and antihypertensive effect.

As used herein, adrenomedullin means activated adrenomedullin unless otherwise stated.

Regarding human adrenomedullin and its precursor, the amino acid sequences and the cDNA sequences are known.

SEQ ID NO: 11 shows the cDNA base sequence of an adrenomedullin precursor. SEQ ID NO: 12 shows the amino acid sequence of the adrenomedullin precursor. The amino acid sequence of SEQ ID NO: 12 is an amino acid sequence encoded by the base sequence of SEQ ID NO: 11. SEQ ID NO: 13 shows the amino acid sequence of adrenomedullin (activated form). SEQ ID NO: 14 shows the amino acid sequence of PAMP.

As the adrenomedullin used herein, in addition to human adrenomedullin, adrenomedullin of other animals, such as rat, mouse, porcine, bovine, etc. can be used. Preferred is adrenomedullin of a mammal. It is preferred for each individual to use adrenomedullin of the same species. For example, it is preferred for a human to use human adrenomedullin.

Examples of the adrenomedullin derivative used herein include those having a structure similar to that of adrenomedullin and having effects similar to those of adrenomedullin (an effect of increasing cAMP in platelets or a vasodilatory and/or antihypertensive effect). The adrenomedullin derivative used herein is preferably a polypeptide having an effect of increasing cAMP in platelets, a vasodilatory effect, and an antihypertensive effect.

Adrenomedullin derivatives include precursors of adrenomedullin. Also, adrenomedullin derivatives include PAMP.

Specific examples of the adrenomedullin and a derivative thereof used in the present invention include a polypeptide having a structure selected from the following (1) to (3):

(1) a polypeptide having an amino acid sequence represented by SEQ ID NO: 12, 13, or 14, (2) a polypeptide having an amino acid sequence represented by SEQ ID NO: 12, 13, or 14 in which one to several amino acids are deleted, substituted, and/or added, and (3) a polypeptide encoded by a nucleic acid capable of hybridizing to a nucleic acid consisting of a base sequence represented by SEQ ID NO: 11 under stringent conditions; and having an effect of increasing cAMP in platelets or a vasodilatory and/or antihypertensive effect.

In the above (3), the nucleic acid may be either RNA or DNA, but DNA is preferred.

The adrenomedullin or a derivative thereof used in the present invention is preferably adrenomedullin (activated form), and more preferably adrenomedullin of a mammal. The above (1) is preferably a polypeptide having an amino acid sequence represented by SEQ ID NO: 13.

In the above (2) of the adrenomedullin or a derivative thereof, the number of amino acids intended by the "one to several amino acids are deleted, substituted, and/or added" is not particularly limited as long as the peptide consisting of the amino acid sequence has the desired function. The number is usually about 30 or less (about 1 to 30), preferably about 15 or less (about 1 to 15), more preferably about 5 or less (about 1 to 5) (for example, preferably about 3 or less (about 1 to 3)), still more preferably about 1 or 2, and particularly preferably about 1. In cases of substitution or the like with amino acids having similar properties (charge and/or polarity), the desired functions are generally retained even if not a few amino acids have been substituted or the like. In cases where substitution or the like occurs at two or more positions, the substitution or the like in all the positions may be deletion only, substitution only, or addition only, or a combination of two or more of deletion, substitution, and addition.

Preferably, the amino acid sequence of the adrenomedullin derivative used herein usually has a sequence identity of about 70% or more, preferably about 80% or more, more preferably about 90% or more, particularly preferably about 95% or more, and most preferably about 97% or more with the amino acid sequence of natural adrenomedullin (for example, SEQ ID NO: 12, 13, or 14).

As used herein, the stringent conditions usually means conditions containing 6 M urea, 0.4% SDS, and 0.5×SSC, or hybridization conditions having similar stringency. Using conditions of higher stringency, for example, conditions containing 6 M urea, 0.4% SDS, and 0.1×SSC, isolation of a DNA with higher homology can be expected. The DNA isolated in the conditions has a high homology or identity at the amino acid level with the amino acid sequence of the targeted protein.

In the present invention, for example, a nucleic acid capable of hybridizing to a nucleic acid consisting of the base sequence of SEQ ID NO: 11 under stringent conditions is preferably a DNA which usually has a sequence identity of about 90% or more, preferably about 95% or more, and more preferably about 98% or more with a DNA consisting of a base sequence complementary to SEQ ID NO: 11 and which encodes a polypeptide having an effect of increasing cAMP in platelets or a vasodilatory and/or antihypertensive effect.

The identity of amino acid sequences or base sequences can usually be determined using the algorithm BLAST by Karlin and Altschul. Based on the algorithm of BLAST, programs called BLASTN or BLASTX have been developed. In cases where analysis of a base sequence is performed using BLASTN, the parameters are set as "score=100" and "wordlength=12", for example. In cases where analysis of an amino acid sequence is performed using BLASTX, the parameters are set as "score=50" and "wordlength=3", for example. In cases where the BLAST and Gapped BLAST programs are used, the default parameters of each program are used. Detailed procedures of these analyzing methods are publicly known.

Whether the adrenomedullin or a derivative thereof has an effect of increasing cAMP in platelets or a vasodilatory and/or antihypertensive effect can be determined by conducting the tests described in literature by Kitamura et al. (Adrenomedullin (11-26): a novel endogenous hypertensive peptide isolated from bovine adrenal medulla. Kitamura K, Matsui E, Kato J, Katoh F, Kita T, Tsuji T, Kangawa K, Eto T. Peptides. 2001 November; 22(11): 1713-8.) and literature by Champion et al. (Structure-activity relationships of adrenomedullin in the circulation and adrenal gland. Champion H C, Nussdorfer G G, Kadowitz P J. Regul Pept. 1999 Nov. 30; 85(1): 1-8).

Examples of other forms of the adrenomedullin derivative used herein include a nucleic acid which encodes adrenomedullin or an adrenomedullin derivative having the polypeptide structure as described above. The nucleic acid should be designed to express, when administered in vivo, the adrenomedullin or its derivatives having the peptide structure as described above.

Adrenomedullin and its derivatives can be produced by a conventional recombinant DNA technology or a chemical synthesis, or a combination thereof, etc. Alternatively, they can be isolated from a natural material.

In cases where chemical synthesis is employed, for example, amino acids with protecting groups are condensed by a liquid phase method and/or a solid phase method for peptide chain elongation, and then the protecting groups are all removed with use of an acid. The resulting crude product is purified by, for example, separation and refinement methods, such as gel filtration, ultrafiltration, dialysis, sodium dodecyl sulfate polyacrylamide gel electrophoresis (SDS-PAGE), and various chromatographic technologies, to give adrenomedullin or its derivatives.

The active ingredient in the medicinal composition described in PCT/JP 2013/077140 may be in a free form or in the form of a pharmacologically acceptable salt thereof. Examples of the salt include a salt with an inorganic base, a salt with an organic base, a salt with an inorganic acid, a salt with an organic acid, a salt with a basic or acidic amino acid, etc.

Preferred examples of the salt with an inorganic base include alkali metal salts, such as a sodium salt and a potassium salt; alkaline earth metal salts, such as a calcium salt and a magnesium salt; an aluminum salt; an ammonium salt; and the like.

Preferred examples of the salt with an organic base include salts with trimethylamine, triethylamine, pyridine, picoline, ethanolamine, diethanolamine, triethanolamine, dicyclohexylamine, N,N'-dibenzylethylenediamine, and the like.

Preferred examples of the salt with an inorganic acid include salts with hydrochloric acid, hydrobromic acid, nitric acid, sulfuric acid, phosphoric acid, and the like.

Preferred examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferred examples of the salt with a basic amino acid include salts with arginine, lysine, ornithine, and the like; and preferred examples of the salt with an acidic amino acid include salts with aspartic acid, glutamic acid, and the like.

In cases where an angiotensin II receptor antagonist or a HMG-CoA reductase inhibitor as an active ingredient of said another metastasis-suppressing agent is orally administered, the agent is preferably administered about once to 3 times daily. For example, in cases where an angiotensin II receptor antagonist or a HMG-CoA reductase inhibitor is used, the agent is preferably orally administered in a daily amount of about 1 to 100 mg/kg bodyweight as an active ingredient, and the dosage is comparable to or less than that used for hypertension or hypercholesterolemia.

In cases where the active ingredient of said another metastasis-suppressing agent is ghrelin or a derivative thereof, the administration rate is, for example, continuous administration of about 0.1 µg/kg·min or less, preferably about 0.08 µg/kg·min or less, or the like.

In cases where the active ingredient of said another metastasis-suppressing agent is adrenomedullin or a derivative thereof, the administration rate is usually, for example, continuous administration of about 0.1 µg/kg·min or less, preferably about 0.05 µg/kg·min or less, or the like.

The duration of the continuous administration of ghrelin, adrenomedullin, or a derivative thereof is usually about one day or longer, and preferably about 1 day to about 2 weeks. In the continuous administration, a preferred administration method is intravenous administration, or the like.

For example, in cases where ghrelin, adrenomedullin, or a derivative thereof is orally administered, a preferable frequency of the administration is, for example, about 4 times or less daily. In cases of parenteral administration, for example, intravenous administration, continuous administration with the use of an infusion pump, a catheter, etc. is preferred.

In cases where the medicament of the present invention and another metastasis-suppressing agent are used in combination, each can be administered over the above-mentioned administration duration appropriate for the administration method.

In said another metastasis-suppressing agent, usually, the active ingredient may be mixed with a publicly known pharmacologically acceptable inert carrier, excipient, diluent, etc. to be formed into a medicinal composition, and administered to an individual by an administration method conventionally used in the pharmaceutical field, i.e., oral administration or parenteral administration, such as permucosal administration, intravenous administration, intramuscular administration, and subcutaneous administration.

For example, in cases where the active ingredient in said another metastasis-suppressing agent is a peptide substance, it may be orally administered as a formulation resistant to degradation in the digestive tract, for example, a microcapsule formulation based on liposomes encapsulating the peptide as the active ingredient. The administration can be performed not through the mucosa of the digestive tract but through, for example, the rectal, nasal, or sublingual mucosa. In this case, the active ingredient can be administered to an individual in the form of, for example, a suppository, a nasal spray, an inhalant, a sublingual tablet, etc. In the present invention, such formulations may be used that the peptide retention in the blood is improved by adopting various controlled-release formulations or long-acting formulations which comprise a biodegradable polymer represented by polysaccharide such as dextran, polyamine, PEG, etc. as a carrier.

When the active ingredient in said another metastasis-suppressing agent is in the form of a nucleic acid encoding a peptide substance, the nucleic acid (such as a gene encoding a peptide substance) may be introduced into a patient via intravenous injection, intramuscular injection, local injection, or the like using a viral vector such as a retrovirus, an adenovirus, and an adeno-associated virus, or using a plasmid etc.

The dosage of the medicament of the present invention varies with the route of administration, the target disease, and the symptoms, the body weight, or the age of the patient, and can be appropriately set depending on the purpose of administration. Generally, the dosage (for example, for oral administration to an adult) is 0.01 to 1000 mg/kg body weight per day, more preferably 0.05 to 500 mg/kg body weight per day as the AT2 receptor agonist, and the appropriately set dosage is preferably administered once a day or several times a day in divided doses.

The administration frequency of the active ingredient in the medicament, the treatment or prevention method, or the like of the present invention is not particularly limited and varies with the active ingredient to be used, the route of administration, and the specific disease to be treated.

The medicament, the treatment or prevention method, or the like of the present invention, when combined with at least one of other usually used anticancer and/or antitumor agents, can achieve more effective treatment of a malignant tumor. The present invention encompasses such a combination treatment with another anticancer agent and/or another antitumor agent. An example of such a combination treatment is an embodiment in which the medicament of the present invention is administered to a patient who is receiving or who has received administration of an anticancer agent and/or an antitumor agent. Since the medicament of the present invention can control the metastasis and invasion of tumor cells, appropriate administration of the medicament during a treatment using another anticancer agent and/or another antitumor agent can increase the efficiency of the treatment and can improve the prognosis of the treatment.

By using the medicament of the present invention with at least one of other usually used anticancer agents and/or antitumor agents, an effect of effectively suppressing or preventing exacerbation and/or augmentation of the metastasis of a malignant tumor caused by the anticancer agent(s) and/or the antitumor agent(s) can also be obtained.

The medicament of the present invention is preferably used for suppressing or preventing exacerbation and/or augmentation of the metastasis of a malignant tumor caused by an anticancer agent and/or an antitumor agent.

The present invention encompasses a method for suppressing or preventing exacerbation and/or augmentation of the metastasis of a malignant tumor caused by an anticancer agent and/or an antitumor agent, the method comprising administering the medicament (or an effective amount thereof) to a patient.

In cases where the medicament of the present invention is administered (in combination or together) with an anticancer agent and/or an antitumor agent, the dosage of the anticancer agent and/or the antitumor agent is not particularly limited and is set as appropriate depending on the type of the agent, the type of disease (malignant tumor); the age, body weight, and degree of the symptoms of the individual (patient); and the route of administration, and may be a usually used amount.

In cases where the medicament of the present invention is administered (in combination or together) with an anticancer agent and/or an antitumor agent, the dosage of the medicament of the present invention varies with the type of disease (malignant tumor); the age, body weight, and degree of the symptoms of the individual (patient); and the route of administration, and can be appropriately selected. The AT2 receptor agonist is administered in an amount of, for example, about 0.01 to 1000 mg/kg body weight per day, preferably 0.05 to 500 mg/kg body weight per day, and the appropriately set dosage is preferably administered (for example, orally administered) once a day or several times a day in divided doses.

In cases where the medicament of the present invention is used with an anticancer agent and/or an antitumor agent, the medicament is preferably administered before (or prior to) the administration of the anticancer agent and/or the antitumor agent. The medicament of the present invention is administered at least before the administration of the anticancer agent and/or the antitumor agent, and after that, can be continuously administered for a period necessary for the treatment.

In cases where an anticancer agent and/or an antitumor agent (for example, a platinum-based antitumor agent, such as cisplatin) is administered, efficient suppression of the metastasis (distant metastasis and recurrence) of a malignant tumor can be achieved as follows. The medicament of the present invention is administered to the patient for preliminary protection of blood vessels, and then the anticancer agent and/or the antitumor agent is administered. The blood vessel protection is continued until the anticancer agent and/or the antitumor agent is eliminated from the body.

Usually, the administration of the medicament of the present invention may be started about 1 or more days (for example, 3 or more days), preferably 1 week or more, and more preferably about 10 days or more before the start of the administration of the anticancer agent and/or the antitumor agent. In addition, the administration of the medicament of the present invention is preferably continued for about 1 or more days (for example, 3 or more days), preferably for 1 week or more, and more preferably for about 10 days or more after the end of the administration of the anticancer agent and/or the antitumor agent.

In cases where an anticancer agent and/or an antitumor agent (for example, a platinum-based antitumor agent, such as cisplatin) is administered, one or more kinds of oral or parenteral agents can be selected as the medicament for the present invention depending on the conditions of the patient. One or more of oral agents and one or more of parenteral agents can be used in combination.

The medicament of the present invention can be used in combination with at least one of said other metastasis-suppressing agents.

In cases where an anticancer agent and/or the antitumor agent (for example, a platinum-based antitumor agent, such as cisplatin) is administered, the medicament of the present invention and at least one of said other metastasis-suppressing agents used in combination can be administered at the same time or at different times.

In such a combined administration, the administration of the medicament of the present invention is usually started about 1 week or more, preferably about 10 days or more before the start of the administration of the anticancer agent and/or the antitumor agent, and preferably continued until about 1 week or more, preferably about 10 days or more after the end of the administration of the anticancer agent and/or the antitumor agent.

In such a combined administration, the dosage form and the administration route of the medicament of the present invention are not particularly limited, and one or more kinds of oral or parenteral dosage forms can be selected depending on the conditions of the patient. One or more of oral dosage forms and one or more of parenteral dosage forms can be used in combination.

In such a combined administration, in cases where one or more of other metastasis-suppressing agents are parenterally, for example intravenously administered, continuous administration with the use of an infusion pump, a catheter, etc. is preferably performed. The duration of the continuous administration is about several hours to several days (for example, about 3 to 14 days, preferably about 3 to 7 days).

In cases where the medicament of the present invention and another metastasis-suppressing agent are used in combination, each can be administered over the above-mentioned administration duration appropriate for the administration method.

In cases where the medicament of the present invention or another metastasis-suppressing agent is administered, the administration is performed depending on the conditions of the patient preferably as follows. For example, before resection or administration of an anticancer agent and/or an antitumor agent, the medicament of the present invention or said another metastasis-suppressing agent is orally administered. After the resection or the administration of the anticancer agent and/or the antitumor agent, i.e., during a period in which oral administration of a medicament etc. cannot be performed, the medicament of the present invention or said another metastasis-suppressing agent is parenterally administered, and after recovery, the medicament of the present invention or said another metastasis-suppressing agent is orally administered.

Examples of the anticancer agent and/or the antitumor agent used in combination with the medicament of the present invention include an alkylating agent, an antimetabolite, an antitumor antibiotic, a plant-derived antitumor substance, a BRM (biological response modifier), a hormone, a vitamin, an anticancer antibody, a molecular targeted agent, a platinum-based antitumor agent, another anticancer agent, another antitumor agent, etc. Among them, preferred as an anticancer agent or an antitumor agent used in combination with the medicament of the present invention is a platinum-based antitumor agent.

More specifically, examples of the alkylating agent include alkylating agents, such as nitrogen mustard, nitrogen mustard N-oxide and chlorambucil; aziridine alkylating agents, such as carboquone and thiotepa; epoxide alkylating agents, such as dibromomannitol and dibromodulcitol; nitrosourea alkylating agents, such as carmustine, lomustine, semustine, nimustine hydrochloride, streptozocin, chlorozotocin, and ranimustine; busulfan, improsulfan tosilate, dacarbazine, etc.

Examples of various antimetabolites include purine antimetabolites, such as 6-mercaptopurine, 6-thioguanine, and thioinosine; pyrimidine antimetabolites, such as fluorouracil, tegafur, tegafur-uracil, carmofur, doxifluridine, broxuridine, cytarabine, and enocitabine; folate antimetabolites, such as methotrexate and trimetrexate; etc.

Examples of the antitumor antibiotic include anthracycline antibiotic antitumor agents, such as mitomycin-C, bleomycin, peplomycin, daunorubicin, aclarubicin, doxorubicin, pirarubicin, THP-adriamycin, 4'-epidoxorubicin, and epirubicin; chromomycin A3; actinomycin-D; etc.

Examples of the plant-derived antitumor substance include vinca alkaloids, such as vindesine, vincristine, and vinblastine; taxanes, such as paclitaxel and docetaxel; epipodophyllotoxins, such as etoposide and teniposide; etc.

Examples of the BRM include a tumor necrosis factor, indomethacin, etc.

Examples of the hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone, medroxyprogesterone, etc.

Examples of the vitamin include vitamin C and vitamin A.

Examples of the antitumor antibody and the molecular targeted agent include trastuzumab, rituximab, cetuximab, nimotuzumab, denosumab, bevacizumab, infliximab, imatinib mesylate, gefitinib, erlotinib, sunitinib, lapatinib, sorafenib, etc.

Examples of the platinum-based antitumor agent include cisplatin, carboplatin, oxaliplatin, etc. Among them, cisplatin is preferred.

Examples of said another anticancer agent and/or said another antitumor agent include tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, krestin, etc.

When the medicament of the present invention is administered in combination with an anticancer/antitumor agent (and/or a metastasis-suppressing agent), the medicament and the anticancer/antitumor agent (and/or the metastasis-suppressing agent) may be contained as active ingredients in a single formulation or in separate formulations.

In cases where the medicament of the present invention is used with an anticancer agent and/or an antitumor agent, the combination of the medicament and the anticancer agent and/or the antitumor agent is not particularly limited. The platinum-based antitumor agent to be used in combination with the medicament of the present invention is preferably cisplatin.

In the present invention, "combined administration" of multiple active ingredients or drugs means that a subject to receive the administration takes all the combined active ingredients or drugs into the body in a certain period of time. The active ingredients may be administered as a single formulation containing all the ingredients (so-called compounding agent). Alternatively, the active ingredients may be separately formulated into separate formulations and then separately administered (so-called administration based on combined use). In cases where the active ingredients are separately formulated, the timing of the administration is not particularly limited. The formulations may be administered simultaneously, on the same day at certain time intervals, or on different days. In cases where two or more active ingredients are administered at different timings of the same day or on different days, the order of administration of the active ingredients is not particularly limited. Normally, each formulation is administered according to each administration method, and therefore the frequency of the administration method may be the same or different among the formulations. In cases where each active ingredient is separately formulated, the administration method (route of administration) may be the same or different among the formulations. It is not necessary that all the active ingredients are present in the body at the same time. As long as all the active ingredients are taken into the body during a certain period of time (for example, one month, preferably one week, more preferably several days, still more preferably one day), it is allowable that one active ingredient has already disappeared from the body when another active ingredient is administered.

EXAMPLES

Hereinafter, the invention will be specifically described by referring to the Examples below. The Examples are merely illustrative examples of the embodiments of the present invention, and the present invention is not limited thereto.

The experimental materials used in the Examples below were obtained and prepared as follows.

The cisplatin (CDDP) used was CISPLATIN inj. "Maruko" (Nichi-Iko Pharmaceutical).

As an angiotensin type 2 receptor agonist, the following compounds were used.

Compound A: (2S)-2-[4-(benzoylamino)benzyl]-N,N-diethyl-N'-(2-naphthylsulfonyl)malonamide Compound B: (2S)-2-{4-[(2-amino-6-fluorobenzoyl)amino]benzyl}-N,N-diethyl-N'-(2-naphthylsulfonyl)malonamide Compound C: 2-allyl-N-(4-fluorophenyl)-N-isopropyl-N'-((E)-styrylsulfonyl)malonamide Compound D: N-(4-fluorophenyl)-2-isobutyl-N-isopropyl-N'-((E)-styrylsulfonyl)malonamide, Compound E: (2S)-2-{4-[(2-amino-4-chlorobenzoyl)amino]benzyl}-N,N-diethyl-N'-(2-naphthylsulfonyl)malonamide Example 1

Lung Metastasis Suppressing Effect of Medicament in Blood-Borne Metastasis Model Established by Injection of Mouse Melanoma to Mouse Tail Vein (CDDP)

Eight-week-old male C57BL6 mice (purchased from Japan SLC, Inc.) were used. Mouse melanoma B16-F10 was purchased from ATCC, and cultured in Dulbecco's Modified Eagle Medium (DMEM) (Life Technologies Corp.) containing 10% fetal calf serum (FCS) under 5% $CO_2$ at 37° C. The cells in a semiconfluent state were treated with EDTA-trypsin (a 0.01 to 0.125% solution), centrifuged, and then suspended in serum free DMEM so as to be $3 \times 10^6$ cells/mL. The melanoma cell suspension (100 μL/mouse, $3 \times 10^5$ cells) was injected to the tail vein of the mice.

As pretreatment, 2.5 mg/kg of cisplatin (CDDP) was injected to the tail vein of the mice 2 days before the injection of the melanoma cells into the tail vein.

As an angiotensin type 2 receptor agonist, Compound A was used.

To the angiotensin type 2 receptor agonist group, a 0.5% carboxymethylcellulose aqueous solution prepared so as to contain 30 mg/kg of Compound A was orally given from 4 days before the start of the CDDP administration to the end of the experiment (14 days after the injection of melanoma cells) in a continuous manner.

To the control group, CDDP was not injected, and only a 0.5% carboxymethylcellulose aqueous solution not containing the agent was orally given for the experiment.

In addition, for the purpose of comparison, an experiment in which CDDP was not injected and Compound A was orally administered and an experiment in which CDDP was injected and the 0.5% carboxymethylcellulose aqueous solution not containing the agent (Compound A) was orally given were performed.

The number of animals in each group was n=5.

Figure 2:
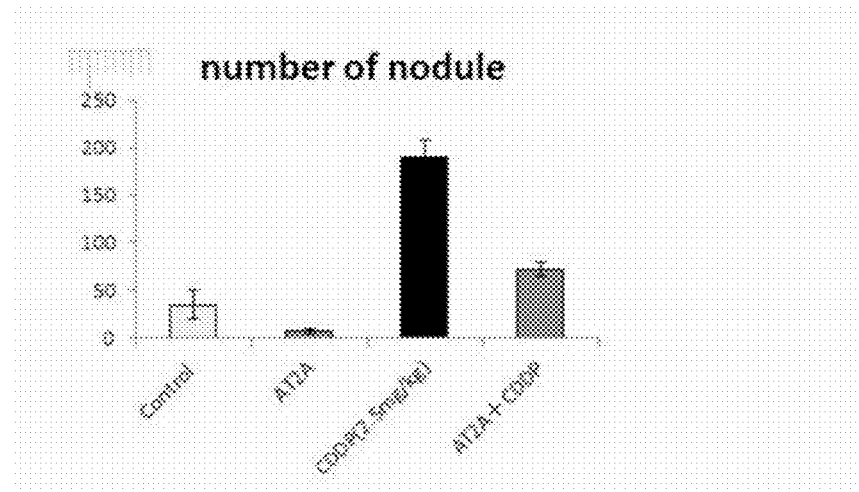
FIG. 2 shows a graph showing the number of nodules formed due to lung metastasis at 2 weeks after the injection of mouse melanoma B16-F10 tumor cells into the tail vein of mice in a tail vein injection metastasis test where injection of CDDP and/or oral administration of Compound A were performed.

The lung metastasis of the tumor cells 14 days after the tumor cell injection was observed. The results are shown in FIG. 1. FIG. 2 shows the number of the observed nodules per animal formed due to lung metastasis (average and standard error of n=5).

In FIG. 1 and FIG. 2, "Control" indicates the lung and the number of nodules of control mice (neither CDDP injection nor oral administration of Compound A was performed), "AT2A" indicates the lung and the number of nodules of mice for which only oral administration of Compound A was performed, "CDDP" indicates the lung and the number of nodules of mice for which only CDDP injection was performed, and "AT2A+CDDP" indicates the lung and the number of nodules of mice for which CDDP injection and oral administration of Compound A were performed. In FIG. 1, black parts are nodules (metastatic foci) formed by metastasized melanoma.

FIG. 1 and FIG. 2 show that administration of cisplatin (CDDP) augmented the lung metastasis of tumor cells but Compound A significantly suppressed the CDDP-induced exacerbation of the lung metastasis. It was also revealed that, even without CDDP administration, Compound A is capable of suppressing the lung metastasis of tumor cells.

Example 2

Lung Metastasis Suppressing Effect of Medicament in Blood-Borne Metastasis Model Established by Injection of Mouse Melanoma to Mouse Tail Vein (LPS)

Eight-week-old male C57BL6 mice (purchased from Japan SLC, Inc.) were used. Lipopolysaccharide (LPS) in an amount of 1 mg/kg was injected to the tail vein of each mouse, and mouse melanoma B16-F10 was injected to the tail vein 4 to 5 hours later. At this time, mouse melanoma was injected into the tail vein on the different side from the tail vein to which LPS was injected. Mouse melanoma B16-F10 was purchased from ATCC, and cultured in DMEM (Life Technologies Corp.) containing 10% FCS under 5% $CO_2$ at 37° C. The cells in a semiconfluent state were treated with EDTA-trypsin (a 0.01 to 0.125% solution) and then centrifuged. As an angiotensin type 2 receptor agonist, Compounds A to E were used. The cells were suspended in serum free DMEM so as to be $3 \times 10^6$ cells/mL for Compound A administration group, and $2 \times 10^6$ cells/mL for Compound B to E administration groups. The melanoma cell suspension (100 L/mouse) at a density of $3 \times 10^5$ cells for Compound A administration group or at a density of $2 \times 10^5$ cells/mL for Compound B to E administration groups was injected to the tail vein of the mice.

To the angiotensin type 2 receptor agonist group, a 0.5% carboxymethylcellulose aqueous solution (0.2 mg/mL) prepared so as to contain 30 mg/kg-day of the agent (each of Compounds A to E) was orally given from 4 days before the start of the LPS administration to the end of the experiment (14 days after the injection of melanoma cells) in a continuous manner. To the control group, LPS was not injected, and only a 0.5% carboxymethylcellulose aqueous solution not containing the agent (any of Compounds A to E) was orally given for the experiment.

In addition, for the purpose of comparison, an experiment in which LPS was not injected and Compound A was orally administered and an experiment in which LPS was injected and the 0.5% carboxymethylcellulose aqueous solution not containing the agent (any of Compounds A to E) was orally given were performed.

The number of animals in each group was n=5.

Figure 3:
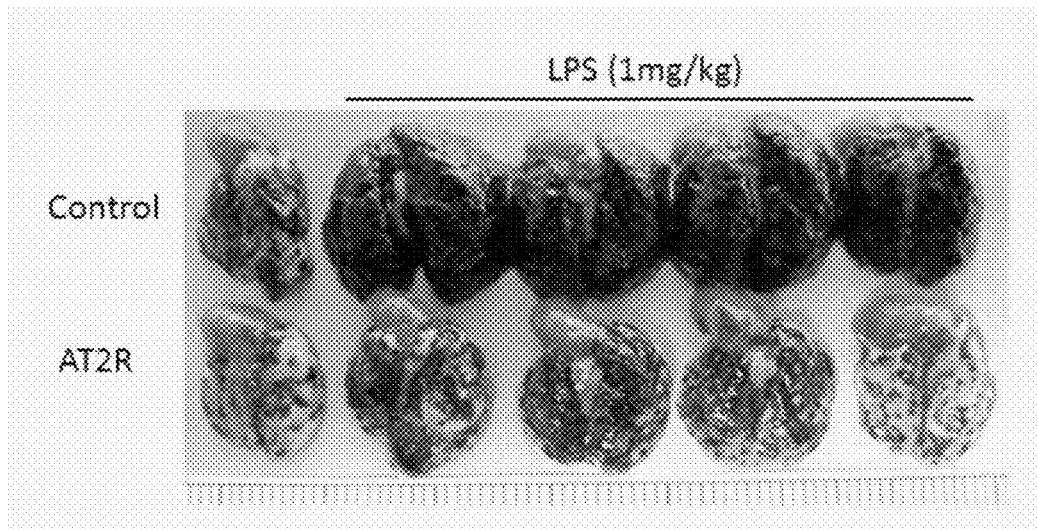
FIG. 3 shows micrographs of lungs at 2 weeks after the injection of mouse melanoma B16-F10 tumor cells into the tail vein of mice in a tail vein injection metastasis test where injection of LPS and/or oral administration of Compound A were performed.
Figure 4:
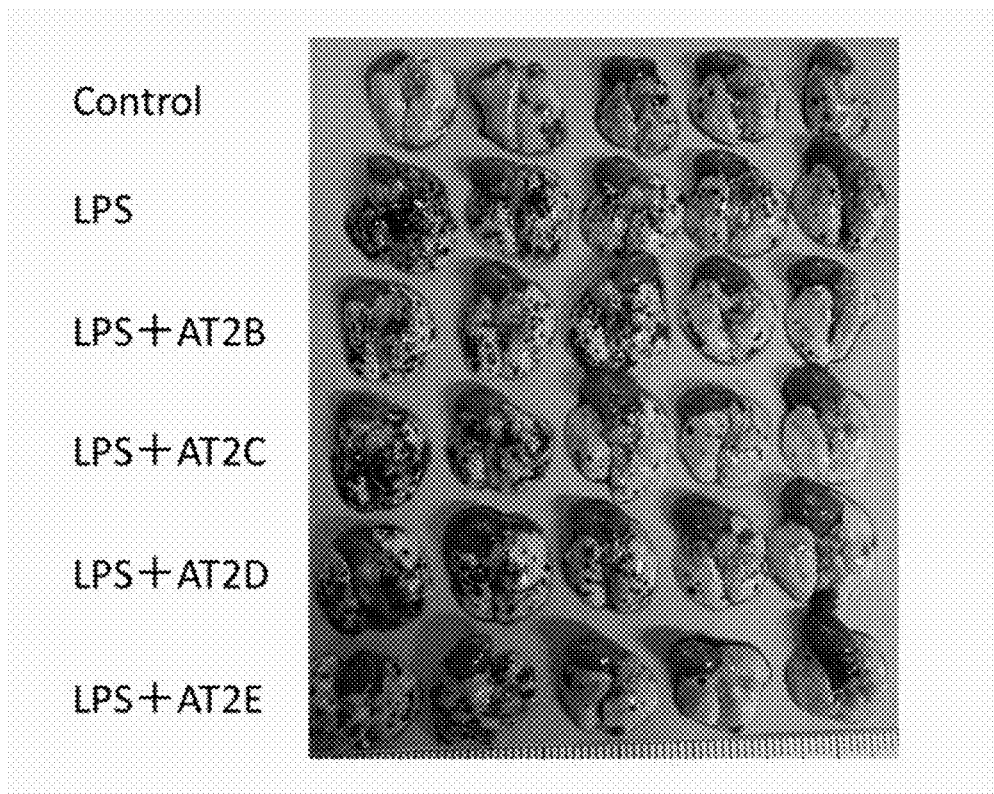
FIG. 4 shows micrographs of lungs at 2 weeks after the injection of mouse melanoma B16-F10 tumor cells into the tail vein of mice in a tail vein injection metastasis test where injection of LPS and/or oral administration of Compounds B to E were performed.

The lung metastasis of the tumor cells 14 days after the tumor cell injection was observed. The results are shown in FIG. 3 and FIG. 4. FIGS. 5 to 9 show the number of the observed nodules per animal formed due to lung metastasis (average and standard error of n=5).

In FIG. 3, the leftmost in the upper row is the lungs of a control mouse (neither LPS injection nor oral administration of Compound A was performed), the 2nd to the 5th from the left in the upper row are the lungs of mice for which only LPS injection was performed, the leftmost in the lower row is the lungs of a mouse for which only oral administration of Compound A was performed, and the 2nd to the 5th from the left in the lower row are the lungs of mice for which LPS injection and oral administration of Compound A were performed. In FIG. 3, black parts are nodules (metastatic foci) formed by metastasized melanoma.

In FIG. 4, "Control" indicates the lungs of control mice (neither LPS injection nor oral administration of the agent (any of Compounds B to E) was performed), "LPS" indicates the lungs of mice for which only LPS injection was performed, "LPS+AT2B" indicates the lungs of mice for which LPS injection and oral administration of Compound B were performed, "LPS+AT2C" indicates the lungs of mice for which LPS injection and oral administration of Compound C were performed, "LPS+AT2D" indicates the lungs of mice for which LPS injection and oral administration of Compound D were performed, and "LPS+AT2E" indicates the lungs of mice for which LPS injection and oral administration of Compound E were performed. In FIG. 4, black parts are nodules (metastatic foci) formed by metastasized melanoma.

Figure 5:
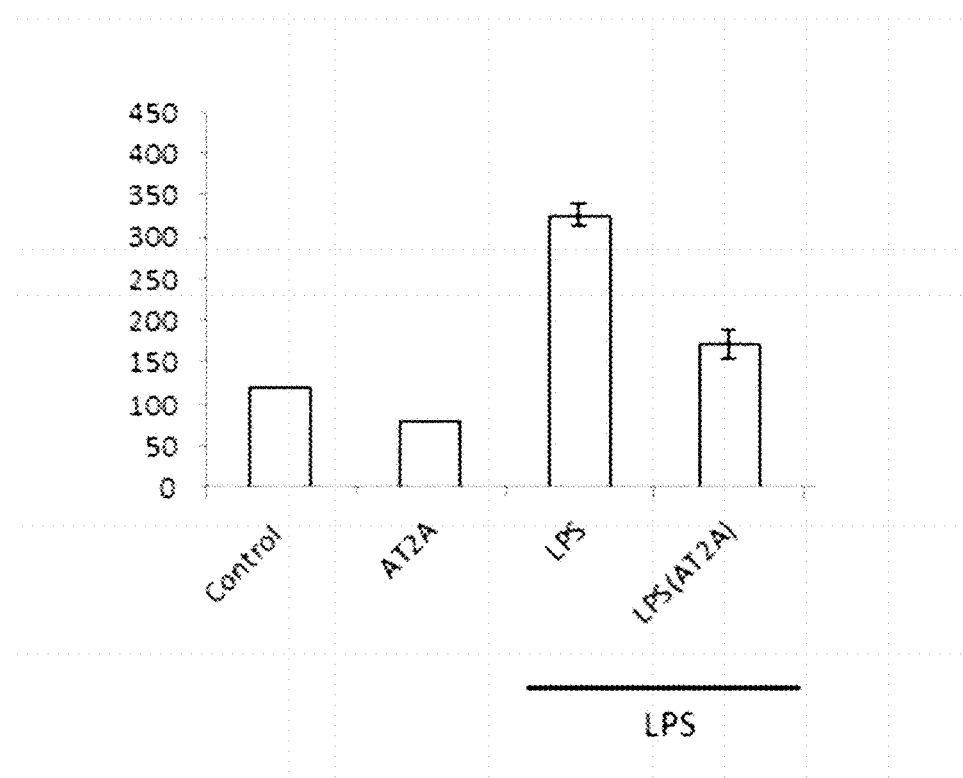
FIG. 5 shows a graph showing the number of nodules formed due to lung metastasis at 2 weeks after the injection of mouse melanoma B16-F10 tumor cells into the tail vein of mice in a tail vein injection metastasis test where injection of LPS and/or oral administration of Compound A were performed.
Figure 6:
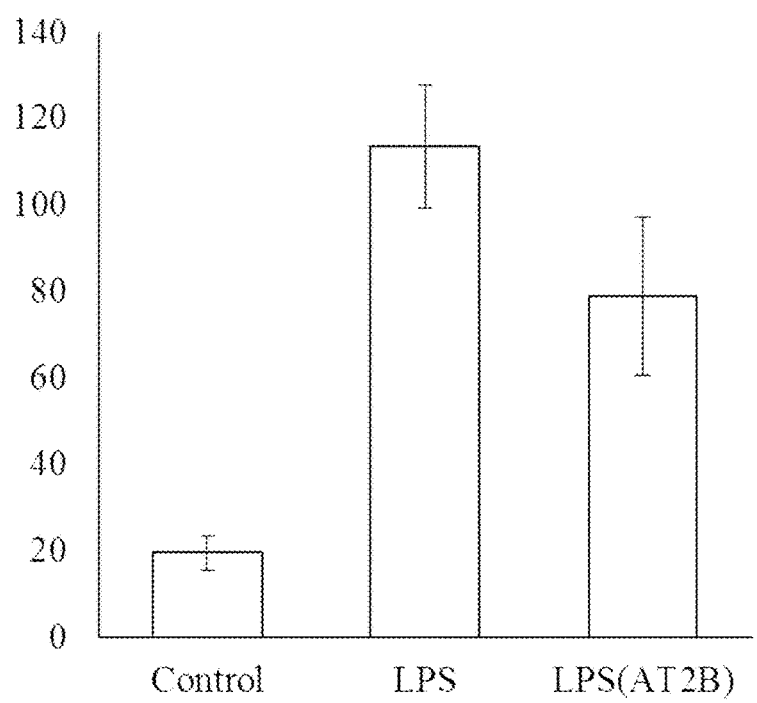
FIG. 6 shows a graph showing the number of nodules formed due to lung metastasis at 2 weeks after the injection of mouse melanoma B16-F10 tumor cells into the tail vein of mice in a tail vein injection metastasis test where injection of LPS and/or oral administration of Compound B were performed.

In FIG. 5, "Control" indicates the number of nodules of control mice (neither LPS injection nor oral administration of the agent was performed), "AT2A" indicates the number of nodules of mice for which only oral administration of Compound A was performed, "LPS" indicates the number of nodules of mice for which only LPS injection was performed, and "LPS (AT2A)" indicates the number of nodules of mice for which LPS injection and oral administration of Compound A were performed, In FIG. 6, "Control" indicates the number of nodules of control mice (neither LPS injection nor oral administration of the agent was performed), "LPS" indicates the number of nodules of mice for which only LPS injection was performed, and "LPS (AT2B)" indicates the number of nodules of mice for which LPS injection and oral administration of Compound B were performed.

Figure 7:
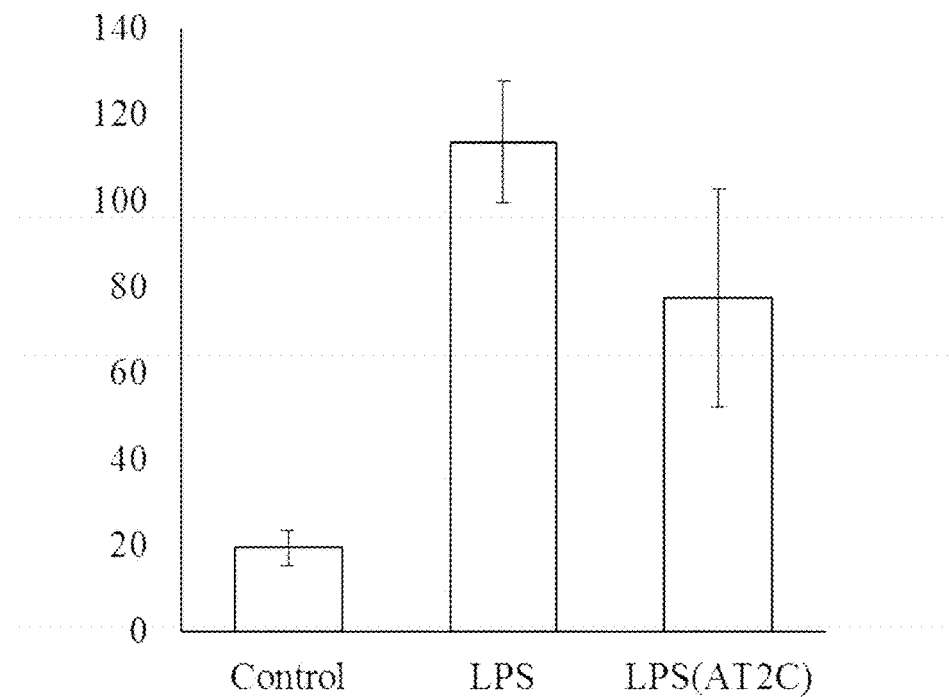
FIG. 7 shows a graph showing the number of nodules formed due to lung metastasis at 2 weeks after the injection of mouse melanoma B16-F10 tumor cells into the tail vein of mice in a tail vein injection metastasis test where injection of LPS and/or oral administration of Compound C were performed.

In FIG. 7, "Control" indicates the number of nodules of control mice (neither LPS injection nor oral administration of the agent was performed), "LPS" indicates the number of nodules of mice for which only LPS injection was performed, and "LPS (AT2C)" indicates the number of nodules of mice for which LPS injection and oral administration of Compound C were performed.

Figure 8:
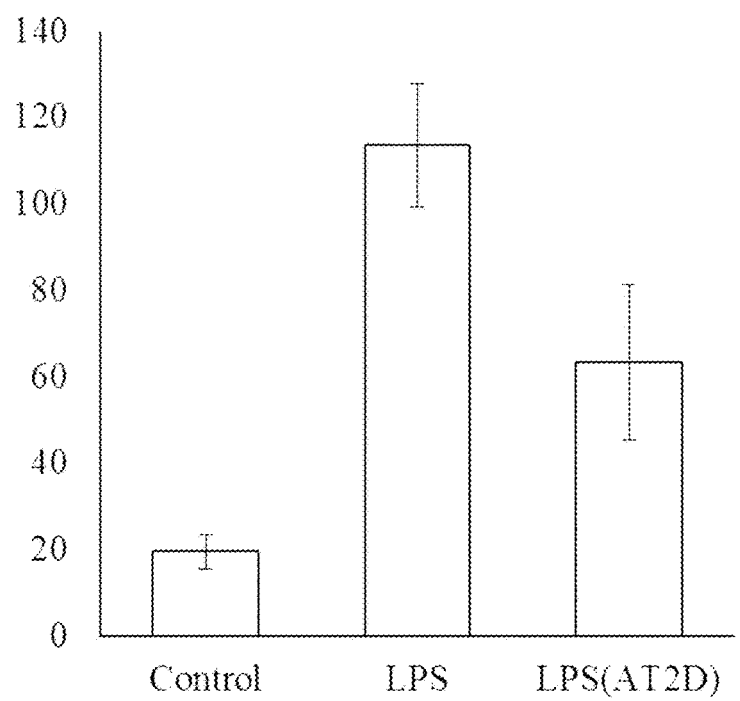
FIG. 8 shows a graph showing the number of nodules formed due to lung metastasis at 2 weeks after the injection of mouse melanoma B16-F10 tumor cells into the tail vein of mice in a tail vein injection metastasis test where injection of LPS and/or oral administration of Compound D were performed.

In FIG. 8, "Control" indicates the number of nodules of control mice (neither LPS injection nor oral administration of the agent was performed), "LPS" indicates the number of nodules of mice for which only LPS injection was performed, and "LPS (AT2D)" indicates the number of nodules of mice for which LPS injection and oral administration of Compound D were performed.

Figure 9:
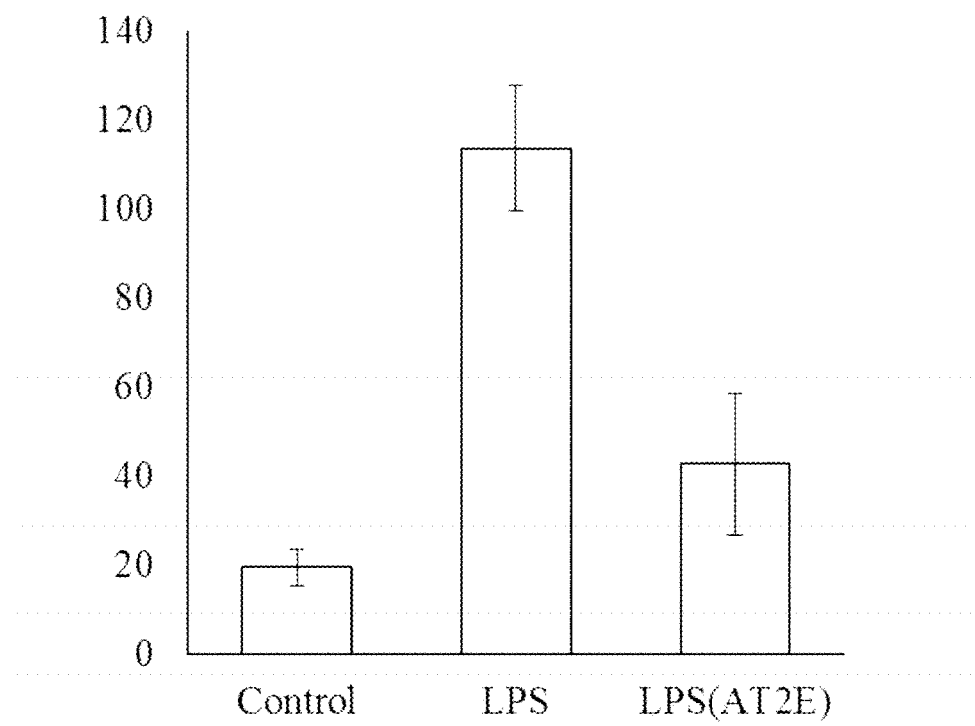
FIG. 9 shows a graph showing the number of nodules formed due to lung metastasis at 2 weeks after the injection of mouse melanoma B16-F10 tumor cells into the tail vein of mice in a tail vein injection metastasis test where injection of LPS and/or oral administration of Compound E were performed.

In FIG. 9, "Control" indicates the number of nodules of control mice (neither LPS injection nor oral administration of the agent was performed), "LPS" indicates the number of nodules of mice for which only LPS injection was performed, and "LPS (AT2E)" indicates the number of nodules of mice for which LPS injection and oral administration of Compound E were performed.

FIGS. 3 to 9 show that administration of any of Compounds A to E suppressed the LPS-induced lung metastasis of tumor cells, and in particular, Compounds A and E significantly suppressed the lung metastasis of tumor cells. It was also revealed that, even without LPS administration, Compound A suppresses the lung metastasis of tumor cells. The results suggest the potential efficacy of the medicament of the present invention in suppressing the exacerbation and/or augmentation of the metastasis of a malignant tumor associated with vascular inflammation (for example, vascular inflammation caused by surgery).

Example 3

Lung Metastasis Suppressing Effects of Medicament in Angiotensin Type 2 Receptor Knockout Mice that Received Injection of Mouse Melanoma to Mouse Tail Vein (LPS)

Wild-type and angiotensin type 2 receptor knockout C57BL6 mice (both types were 4-week old, male, and purchased from Charles River Japan) were used. Lipopolysaccharide (LPS) in an amount of 1 mg/kg was injected to the tail vein of each mouse, and mouse melanoma B16-F10 was injected to the tail vein 4 to 5 hours later. At this time, mouse melanoma was injected into the tail vein on the different side from the tail vein to which LPS was injected. Mouse melanoma B16-F10 was purchased from ATCC, and cultured in DMEM (Life Technologies Corp.) containing 10% FCS under 5% $CO_2$ at 37° C. The cells in a semiconfluent state were treated with EDTA-trypsin (a 0.01 to 0.125% solution), centrifuged, and then suspended in serum free DMEM so as to be $2.5 \times 10^6$ cells/mL. The melanoma cell suspension (100 μL/mouse, $2.5 \times 10^5$ cells) was injected to the tail vein of the mice.

As an angiotensin type 2 receptor agonist, Compound A was used.

To the angiotensin type 2 receptor agonist group, a 0.5% carboxymethylcellulose aqueous solution (0.2 mg/mL) prepared so as to contain 30 mg/kg·day of Compound A was orally given from 4 days before the start of the LPS administration to the end of the experiment (14 days after the injection of melanoma cells) in a continuous manner.

To the control group, LPS was not injected, and only a 0.5% carboxymethylcellulose aqueous solution not containing the agent was orally given for the experiment.

In addition, for the purpose of comparison, an experiment in which LPS was injected and the 0.5% carboxymethylcellulose aqueous solution not containing the agent (Compound A) was orally given was performed.

The number of animals in each group was n=4.

Figure 10:
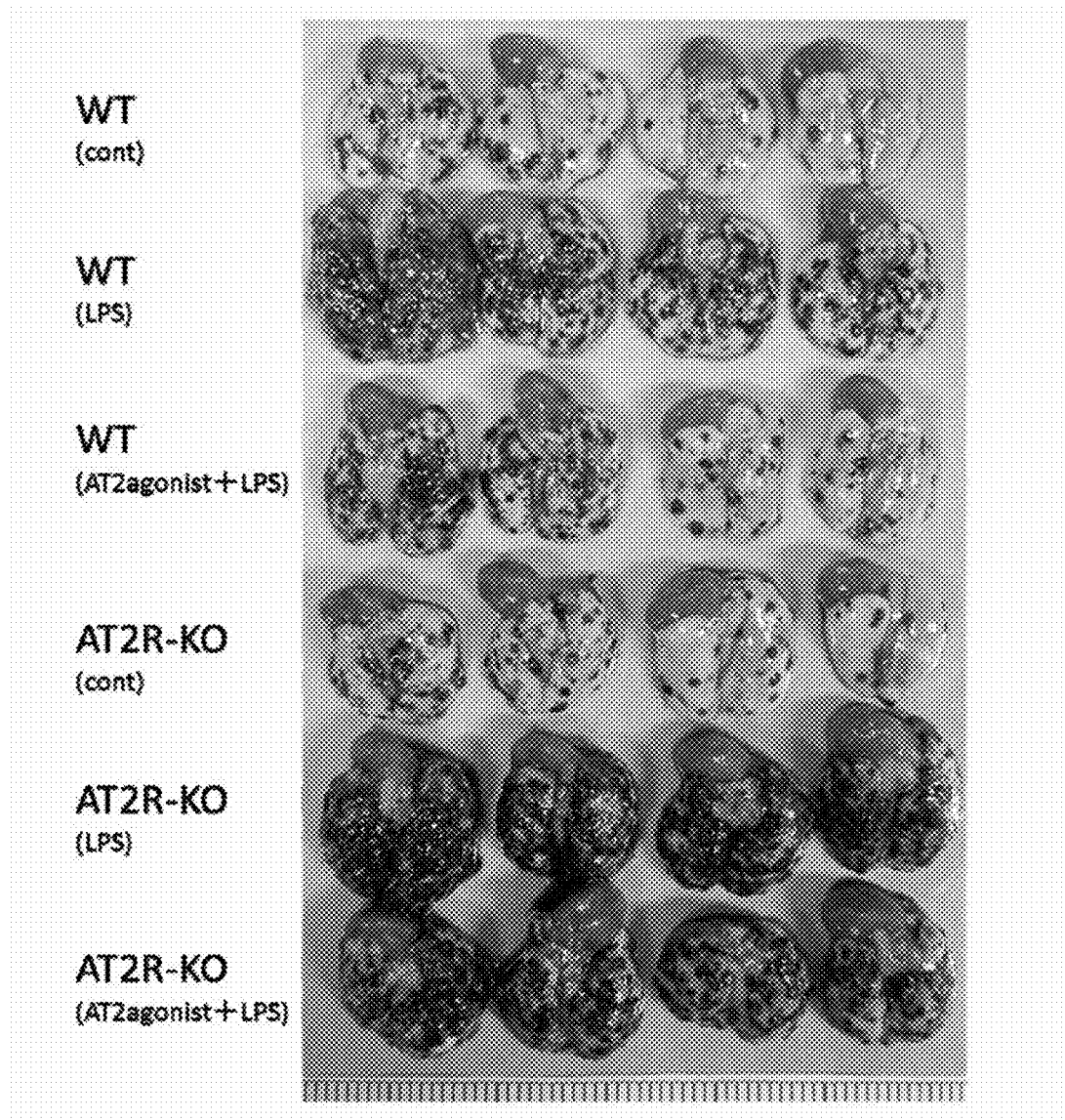
FIG. 10 shows micrographs of lungs at 2 weeks after the injection of mouse melanoma B16-F10 tumor cells into the tail vein of angiotensin type 2 receptor knockout mice in a tail vein injection metastasis test where injection of LPS and/or oral administration of Compound A were performed.
Figure 11:
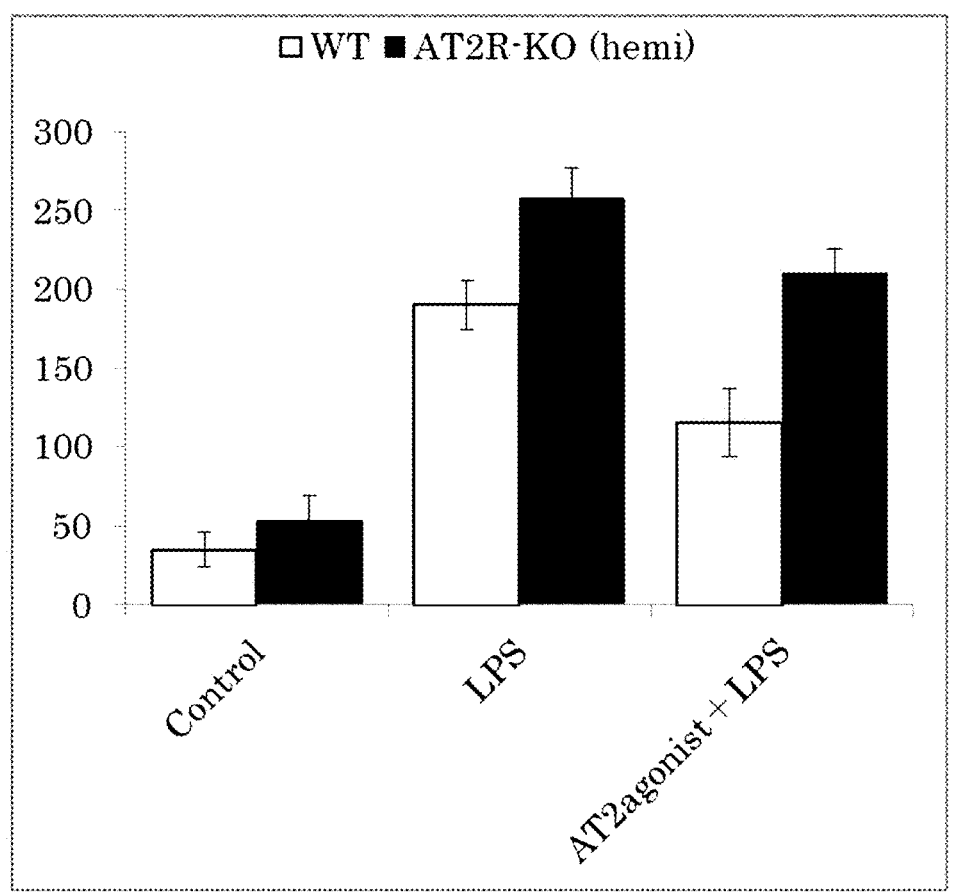
FIG. 11 shows a graph showing the number of nodules formed due to lung metastasis at 2 weeks after the injection of mouse melanoma B16-F10 tumor cells into the tail vein of angiotensin type 2 receptor knockout mice in a tail vein injection metastasis test where injection of LPS and/or oral administration of Compound A were performed.

The lung metastasis of the tumor cells 14 days after the tumor cell injection was observed. The results are shown in FIG. 10. FIG. 11 shows the number of the observed nodules per animal formed due to lung metastasis (average and standard error of n=4).

In FIG. 10, "WT" indicates the lungs of control wild-type mice (neither LPS injection nor oral administration of the agent was performed), "WT (LPS)" indicates the lungs of wild-type mice for which only LPS injection was performed, "WT (AT2 agonist+LPS)" indicates the lungs of wild-type mice for which LPS injection and oral administration of the agent (Compound A) were performed, "AT2R-KO (cont)" indicates the lungs of control angiotensin type 2 receptor knockout mice (neither LPS injection nor oral administration of the agent was performed), "AT2R-KO (LPS)" indicates the lungs of angiotensin receptor type 2 knockout mice for which only LPS injection was performed, "AT2R-KO (AT2 agonist+LPS)" indicates the lungs of angiotensin type 2 receptor knockout mice for which LPS injection and oral administration of the agent (Compound A) were performed. In FIG. 10, black parts are nodules (metastatic foci) formed by metastasized melanoma.

In FIG. 11, "Control" indicates the number of nodules of control mice (neither LPS injection nor oral administration of the agent was performed), "LPS" indicates the number of nodules of mice for which only LPS injection was performed, and "AT2 agonist+LPS" indicates the number of nodules of mice for which LPS injection and oral administration of the agent (Compound A) were performed.

FIG. 10 and FIG. 11 show that administration of LPS augmented the lung metastasis of a malignant tumor in both the wild-type mice and angiotensin type 2 receptor knockout mice. In wild-type mice, administration of the angiotensin type 2 receptor agonist suppressed the lung metastasis of the malignant tumor, but in angiotensin type 2 receptor knockout mice, administration of the angiotensin type 2 receptor agonist did not suppress the lung metastasis of the malignant tumor.

The results suggest that angiotensin type 2 receptors are involved in the suppression of the lung metastasis of a malignant tumor, and therefore, it is expected that angiotensin type 2 receptor agonists suppress the exacerbation and/or augmentation of the metastasis of a malignant tumor.

INDUSTRIAL APPLICABILITY

The present invention provides an excellent medicament capable of suppressing the metastasis of a malignant tumor, a method for suppressing or preventing the metastasis, and a method for treating or preventing the metastasis of a malignant tumor. Further, the present invention exerts an excellent metastasis suppressing effect even on a malignant tumor of which the metastasis has been exacerbated by an anticancer agent and/or an antitumor agent. Therefore, the present invention is useful in the fields of medicine etc.

The invention claimed is:

1. A method for suppressing or preventing one or more of (1) the metastasis of a malignant tumor, (2) the exacerbation and/or augmentation of the metastasis of a malignant tumor caused by an anticancer agent and/or an antitumor agent, or (3) the exacerbation and/or augmentation of the metastasis of a malignant tumor associated with vascular inflammation, said method comprising:

administering an effective amount of a non-peptidic angiotensin type 2 receptor agonist to a subject in need thereof, wherein the subject is a patient who is receiving or who has received administration of an anticancer agent and/or an antitumor agent.

2. The method according to claim 1, wherein the vascular inflammation is caused by surgery.

3. The method according to claim 1, wherein the non-peptidic angiotensin type 2 receptor agonist is a compound represented by the following general formula (I):

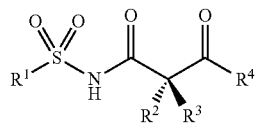

wherein $R^1$ represents 2-naphthyl, trans-β-styryl, phenethyl, 3-phenoxypropyl, or 4-phenylbutyl;

one of $R^2$ and $R^3$ represents a hydrogen atom, and the other represents isopropyl, isobutyl, neopentyl, allyl, —$CH_2$—$R^5$, —$(CH_2)_2$—$R^{5'}$, or —$(CH_2)_n$—Ar, wherein $R^5$ represents optionally substituted $C_{3-10}$ cycloalkyl, optionally substituted heterocycle, or —CO—$NR^6R^7$, wherein R⁶ and R⁷ may be the same or different, and each represent a hydrogen atom, $C_{1-6}$ alkyl, optionally substituted aryl, or optionally substituted heteroaryl, or R⁵ and R⁶ together with the nitrogen atom to which they are bonded may form optionally substituted cyclic amino)}, R⁵' represents cyano or $C_{1-6}$ alkoxy, n represents an integer of 1 to 3, and Ar represents optionally substituted phenyl or optionally substituted heteroaryl, or R² and R³ together with the carbon atom to which they are bonded may form the moiety of the following formula:

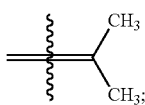 [SMILES: *=C(C)C]

and

R⁴ represents di($C_{1-6}$ alkyl)amino or a moiety of the following formula:

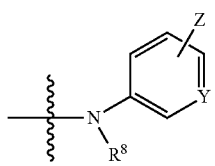

wherein

Z represents a hydrogen atom, a halogen atom, or trifluoromethyl,

Y represents a nitrogen atom or CH, and

R⁸ represents ethyl, isopropyl, or 3-pentyl with the proviso that when Y is a nitrogen atom, Z represents a hydrogen atom;

or a pharmacologically acceptable salt thereof.

4. The method according to claim 1, wherein the non-peptidic angiotensin type 2 receptor agonist is at least one compound selected from the group consisting of:

N,N-diethyl-2-{4-[(2,6-difluorobenzoyl)amino]benzyl}-N'-(2-naphthylsulfonyl)malonamide, (2S)-2-[4-(benzoylamino)benzyl]-N,N-diethyl-N'-(2-naphthylsulfonyl)malonamide, (2S)—N,N-diethyl-2-{4-[(2-fluorobenzoyl)amino]benzyl}-N'-(2-naphthylsulfonyl)malonamide, (2S)—N,N-diethyl-2-{4-[(3-fluorobenzoyl)amino]benzyl}-N'-(2-naphthylsulfonyl)malonamide, (2S)—N,N-diethyl-2-{4-[(2,4-difluorobenzoyl)amino]benzyl}-N'-(2-naphthylsulfonyl)malonamide, (2S)—N,N-diethyl-2-{4-[(4-methylbenzoyl)amino]benzyl}-N'-(2-naphthylsulfonyl)malonamide, (2 S)—N,N-diethyl-N'-(2-naphthylsulfonyl)-2-{4-[(2-thienoyl)amino]benzyl}malonamide, (2 S)—N,N-diethyl-2-{4-[(2-furoyl)amino]benzyl}-N'-(2-naphthylsulfonyl)malonamide, (2S)-2-{4-[(2-amino-5-fluorobenzoyl)amino]benzyl}-N,N-diethyl-N'-(2-naphthylsulfonyl)malonamide, (2S)-2-{4-[(2-amino-6-fluorobenzoyl)amino]benzyl}-N,N-diethyl-N'-(2-naphthylsulfonyl)malonamide, (2S)—N,N-diethyl-N'-(2-naphthylsulfonyl)-2-{4-[(2-pyridylcarbonyl)amino]benzyl}malonamide, (2S)-2-{4-[(2-amino-4-chlorobenzoyl)amino]benzyl}-N,N-diethyl-N'-(2-naphthylsulfonyl)malonamide, (2S)-2-{4-[(2-aminobenzoyl)amino]benzyl}-N,N-diethyl-N'-(2-naphthylsulfonyl)malonamide, (2S)-2-{4-[(2-amino-5-chlorobenzoyl)amino]benzyl}-N,N-diethyl-N'-(2-naphthylsulfonyl)malonamide, (2S)-2-{4-[(2-amino-4,5-difluorobenzoyl)amino]benzyl}-N,N-diethyl-N'-(2-naphthylsulfonyl)malonamide, (2S)-2-{4-[(2-amino-4-fluorobenzoyl)amino]benzyl}-N,N-diethyl-N'-(2-naphthylsulfonyl)malonamide, (2 S)-2-{4-[(2-amino-5-methylbenzoyl)amino]benzyl}-N,N-diethyl-N'-(2-naphthylsulfonyl)malonamide, 2-(4-fluorobenzyl)-N-isopropyl-N-(3-pyridyl)-N'-((E)-styrylsulfonyl)malonamide, 2-allyl-N-(4-fluorophenyl)-N-isopropyl-N'-((E)-styrylsulfonyl)malonamide, N-(4-fluorophenyl)-2-isobutyl-N-isopropyl-N'-((E)-styrylsulfonyl)malonamide, N-(4-fluorophenyl)-2-isobutyl-N-isopropyl-N'-phenethylsulfonylmalonamide, N-(4-fluorophenyl)-2-isobutyl-N-isopropyl-N'-(2-naphthylsulfonyl)malonamide, (2S or 2R)-2-cyclopropylmethyl-N-(4-fluorophenyl)-N-isopropyl-N'-((E)-2-styrylsulfonyl)malonamide, 2-cyclopropylmethyl-N-(4-fluorophenyl)-N-isopropyl-N'-phenethylsulfonylmalonamide, and 2-cyclopropylmethyl-N-(4-fluorophenyl)-N-isopropyl-N'-(2-naphthylsulfonyl)malonamide, or a pharmacologically acceptable salt thereof.

5. The method according to claim 1, wherein the metastasis of a malignant tumor is metastasis to at least one of the lung, the bone, the liver, or the brain.

6. The method according to claim 1, wherein the metastasis of a malignant tumor is metastasis to at least one of the lung or the liver.

7. The method according to claim 1, wherein the malignant tumor is at least one of an epithelial malignant tumor, a non-epithelial malignant tumor, or a melanoma.

8. The method according to claim 1, wherein the malignant tumor is a melanoma.

9. The method according to claim 1, wherein the subject is a patient who is to undergo or who has undergone resection of a malignant tumor.

10. The method according to claim 1, further comprising administering an anticancer agent and/or an antitumor agent to the subject.

11. The method according to claim 10, wherein the anticancer agent and/or the antitumor agent is a platinum-based antitumor agent.

12. The method according to claim 10, wherein the non-peptidic angiotensin type 2 receptor agonist is administered before the administration of the anticancer agent and/or the antitumor agent.

13. The method according to claim 12, wherein the non-peptidic angiotensin type 2 receptor agonist is administered one or more days before the start of the administration of the anticancer agent and/or the antitumor agent.

14. The method according to claim 1, wherein administration is oral administration.

15. The method according to claim 1, wherein said method is a method for suppressing or preventing (1) the metastasis of a malignant tumor.

16. The method according to claim 1, wherein said method is a method for suppressing or preventing (2) the exacerbation and/or augmentation of the metastasis of a malignant tumor caused by an anticancer agent and/or an antitumor agent.

17. The method according to claim 1, wherein said method is a method for suppressing or preventing (3) the exacerbation and/or augmentation of the metastasis of a malignant tumor associated with vascular inflammation.

18. The method according to claim 15, which includes suppressing or preventing malignant tumor cells from colonizing or invading vascular tissue.

19. The method according to claim 1, wherein the non peptidic angiotensin type 2 receptor agonist is (2S)-2-[4-(benzoylamino)benzyl]-N,N-diethyl-N'-(2-naphthylsulfonyl)malonamide.

20. The method according to claim 1, wherein the non peptidic angiotensin type 2 receptor agonist is (2S)-2-{4-[(2-amino-6-fluorobenzoyl)amino]benzyl}-N,N-diethyl-N'-(2-naphthylsulfonyl)malonamide.

21. The method according to claim 1, wherein the non peptidic angiotensin type 2 receptor agonist is 2-allyl-N-(4-fluorophenyl)-N-isopropyl-N'-((E)-styrylsulfonyl)malonamide.

22. The method according to claim 1, wherein the non peptidic angiotensin type 2 receptor agonist is N-(4-fluorophenyl)-2-isobutyl-N-isopropyl-N'-((E)-styrylsulfonyl)malonamide.

23. The method according to claim 1, wherein the non peptidic angiotensin type 2 receptor agonist is (2S)-2-{4-[(2-amino-4-chlorobenzoyl)amino]benzyl}-N,N-diethyl-N'-(2-naphthylsulfonyl)malonamide.

\* \* \* \* \*